US011076983B2

(12) United States Patent
Biser et al.

(10) Patent No.: US 11,076,983 B2
(45) Date of Patent: *Aug. 3, 2021

(54) THERMAL EYE COMPRESS SYSTEMS AND METHODS OF USE

(71) Applicant: Seth A. Biser, Fleetwood, NY (US)

(72) Inventors: Seth A. Biser, Fleetwood, NY (US); Lawrence Thad Levine, Easton, CT (US); Harvey Levine, Fairfield, CT (US); William Finneran, New York, NY (US)

(73) Assignee: Seth A. Biser, Fleetwood, NY (US)

( * ) Notice: Subject to any disclaimer, the term of this patent is extended or adjusted under 35 U.S.C. 154(b) by 97 days.

This patent is subject to a terminal disclaimer.

(21) Appl. No.: 15/982,553

(22) Filed: May 17, 2018

(65) Prior Publication Data
US 2019/0053940 A1    Feb. 21, 2019

Related U.S. Application Data

(63) Continuation-in-part of application No. 14/179,290, filed on Feb. 12, 2014, now abandoned, and a
(Continued)

(51) Int. Cl.
*A61F 7/02* (2006.01)
*A61F 7/00* (2006.01)

(52) U.S. Cl.
CPC ............. *A61F 7/02* (2013.01); *A61F 7/0241* (2013.01); *A61F 2007/0004* (2013.01);
(Continued)

(58) Field of Classification Search
CPC .. A61F 7/02; A61F 7/0241; A61F 2007/0228; A61F 2007/0242; A61F 2007/0004; A61F 2007/0219
See application file for complete search history.

(56) References Cited

U.S. PATENT DOCUMENTS 702,759 A    6/1902    Allegretti
1,161,321 A    11/1915    Lush
(Continued)

FOREIGN PATENT DOCUMENTS

CN           101172183          11/2006
DE    10 2010 033 343 A1     2/2012
(Continued)

OTHER PUBLICATIONS

U.S. Appl. No. 14/179,290, Office Action dated May 3, 2016, 14 pages.
(Continued)

*Primary Examiner* — Linda C Dvorak
*Assistant Examiner* — Yasamin Ekrami
(74) *Attorney, Agent, or Firm* — The Law Office of Patrick F. O'Reilly III, LLC

(57) ABSTRACT

An apparatus includes a flexible frame, a coupling portion, and an insulating portion. The flexible frame is configured to support a thermal therapeutic member and is transitioned between a first configuration and a second configuration to place the therapeutic member in substantially continuous contact with a target portion of the body. The coupling portion is coupled to the flexible frame and is transitioned from a first configuration to a second configuration to retain the flexible frame in its second configuration. The insulating portion is transitioned from a first configuration to a second configuration to be coupled to the flexible frame. The insulating portion at least partially controls a transfer of thermal energy between the thermal therapeutic member and the target portion of the body.

20 Claims, 59 Drawing Sheets

Related U.S. Application Data continuation-in-part of application No. 14/163,598, filed on Jan. 24, 2014, now abandoned, which is a continuation of application No. 12/947,189, filed on Nov. 16, 2010, now Pat. No. 8,636,786, which is a continuation of application No. PCT/US2009/044327, filed on May 18, 2009, which is a continuation-in-part of application No. 12/153,321, filed on May 16, 2008, now abandoned, and a continuation-in-part of application No. 12/153,322, filed on May 16, 2008, now abandoned, application No. 15/982,553, which is a continuation-in-part of application No. 15/494,574, filed on Apr. 24, 2017, now abandoned, which is a continuation of application No. 14/327,463, filed on Jul. 9, 2014, now Pat. No. 9,629,746, which is a continuation of application No. 13/298,445, filed on Nov. 17, 2011, now Pat. No. 8,784,391.

(60) Provisional application No. 61/415,153, filed on Nov. 18, 2010, provisional application No. 61/852,263, filed on Mar. 15, 2013, provisional application No. 61/962,067, filed on Oct. 30, 2013.

(52) U.S. Cl.
CPC ............... *A61F 2007/0219* (2013.01); *A61F 2007/0228* (2013.01); *A61F 2007/0242* (2013.01)

(56) References Cited

U.S. PATENT DOCUMENTS

| | | | |
|---|---|---|---|
| 1,275,127 | A | 8/1918 | Campbell |
| 1,567,931 | A | 12/1925 | Epler |
| 1,743,244 | A | 1/1930 | Shulman |
| 1,799,064 | A | 3/1931 | Rickerd |
| 1,886,725 | A | 11/1932 | Pederson |
| 2,101,628 | A | 12/1937 | Padelford |
| 2,237,971 | A | 4/1941 | Padelford |
| 2,342,840 | A | 2/1944 | Cadous |
| 2,343,157 | A | 2/1944 | Quering |
| 2,526,582 | A | 10/1950 | Rowan |
| 2,586,851 | A | 2/1952 | Monro et al. |
| 2,728,078 | A | 12/1955 | Taylor |
| 2,755,803 | A | 7/1956 | Dorsey |
| 2,796,903 | A * | 6/1957 | Gazelle ............... A61F 7/103 607/109 |
| 3,173,419 | A | 3/1965 | Dubilier et al. |
| 3,195,539 | A | 7/1965 | Hyman |
| 3,333,586 | A | 8/1967 | Bellis et al. |
| 3,762,419 | A | 10/1973 | Walters |
| 3,768,485 | A | 10/1973 | Linick |
| 3,804,077 | A | 4/1974 | Williams |
| 3,834,396 | A | 9/1974 | Foster et al. |
| 3,836,044 | A | 9/1974 | Tilp et al. |
| 3,885,403 | A | 5/1975 | Spencer |
| 4,019,516 | A | 4/1977 | D'Auria |
| 4,190,054 | A | 2/1980 | Brennan |
| 4,243,041 | A | 1/1981 | Paul |
| 4,252,119 | A | 2/1981 | Coates |
| 4,261,364 | A | 4/1981 | Haddad et al. |
| 4,372,318 | A | 2/1983 | Viesturs et al. |
| 4,473,370 | A | 9/1984 | Weiss |
| 4,517,972 | A | 5/1985 | Finch, Jr. |
| 4,527,565 | A | 7/1985 | Ellis |
| 4,603,442 | A | 8/1986 | Barfield |
| 4,614,189 | A | 9/1986 | MacKenzie |
| 4,671,267 | A | 6/1987 | Stout |
| 4,676,247 | A | 6/1987 | Van Cleve |
| 4,688,566 | A | 8/1987 | Boyce |
| 4,756,311 | A | 7/1988 | Francis, Jr. |
| 4,783,866 | A | 11/1988 | Simmons et al. |
| 4,856,651 | A | 8/1989 | Francis, Jr. |
| 4,910,978 | A | 3/1990 | Gordon et al. |
| 4,953,544 | A | 9/1990 | Hansen et al. |
| 5,016,629 | A | 5/1991 | Kanare |
| 5,035,241 | A | 7/1991 | Walasek et al. |
| 5,065,758 | A | 11/1991 | Whitehead et al. |
| 5,069,208 | A | 12/1991 | Noppel et al. |
| 5,094,238 | A | 3/1992 | Gibbon |
| 5,119,812 | A | 6/1992 | Angelo |
| 5,129,391 | A | 7/1992 | Brodsky et al. |
| 5,188,103 | A | 2/1993 | Smith |
| 5,190,032 | A | 3/1993 | Zacoi |
| 5,190,033 | A | 3/1993 | Johnson |
| 5,274,865 | A | 1/1994 | Takehashi |
| 5,314,456 | A | 5/1994 | Cohen |
| 5,392,945 | A | 2/1995 | Syrek |
| 5,409,500 | A | 4/1995 | Dyrek |
| 5,456,703 | A | 10/1995 | Beeuwkes, III |
| 5,458,628 | A | 10/1995 | Cipolla |
| 5,540,332 | A | 7/1996 | Kopacz et al. |
| 5,545,197 | A | 8/1996 | Bowen |
| 5,628,772 | A | 5/1997 | Russell |
| 5,643,336 | A | 7/1997 | Lopez-Ciaros |
| 5,679,052 | A | 10/1997 | Rucki |
| 5,700,238 | A | 12/1997 | Hyson |
| 5,716,388 | A | 2/1998 | Petelle |
| 5,733,321 | A | 3/1998 | Brink |
| 5,837,004 | A | 11/1998 | Lavore |
| 5,840,080 | A | 11/1998 | Der Ovanesian |
| 5,879,379 | A | 3/1999 | Mason et al. |
| 5,980,497 | A | 11/1999 | Yavitz |
| 6,030,412 | A | 2/2000 | Klatz et al. |
| 6,017,606 | A | 6/2000 | Sage et al. |
| 6,083,254 | A | 7/2000 | Evans |
| 6,083,256 | A | 7/2000 | Der Ovanesian |
| D432,658 | S | 10/2000 | Haynes |
| 6,126,683 | A | 10/2000 | Momtaheni |
| 6,129,659 | A | 10/2000 | Wilk |
| 6,138,286 | A | 10/2000 | Robrahn et al. |
| 6,155,995 | A | 12/2000 | Lin |
| 6,193,740 | B1 | 2/2001 | Rodriguez |
| 6,202,845 | B1 | 3/2001 | Hill |
| 6,241,711 | B1 | 6/2001 | Weissberg et al. |
| 6,248,125 | B1 | 6/2001 | Helming |
| 6,261,314 | B1 * | 7/2001 | Rich ............... A61F 7/02 607/109 |
| D446,863 | S | 8/2001 | Carroll |
| 6,312,125 | B1 | 11/2001 | Potts |
| 6,316,687 | B1 | 11/2001 | Davis et al. |
| 6,409,746 | B1 | 6/2002 | Igeki et al. |
| 6,440,159 | B1 | 8/2002 | Edwards et al. |
| D463,564 | S | 9/2002 | Siegwart et al. |
| 6,451,046 | B1 | 9/2002 | Leo et al. |
| D464,140 | S | 10/2002 | Lavin, Jr. |
| 6,514,279 | B1 | 2/2003 | Lavin |
| 6,537,308 | B2 | 3/2003 | Burkhart |
| 6,571,799 | B1 | 6/2003 | Daly |
| 6,589,272 | B1 | 7/2003 | Sheikh |
| 6,623,517 | B1 | 9/2003 | DeLuisa et al. |
| 6,648,909 | B2 | 11/2003 | Helming |
| 6,656,210 | B1 | 12/2003 | Plewes |
| 6,823,860 | B2 | 11/2004 | Igaki et al. |
| 6,824,556 | B1 | 11/2004 | Lachance |
| D504,951 | S | 5/2005 | Johnston |
| 6,886,553 | B2 | 5/2005 | Yim |
| 6,886,933 | B2 | 5/2005 | Schwebel |
| 6,908,195 | B2 | 6/2005 | Fuller |
| 6,931,644 | B2 | 8/2005 | Chen |
| 6,936,018 | B2 | 8/2005 | Chalek |
| 7,211,070 | B2 | 5/2007 | Soroudi |
| 7,231,922 | B2 | 6/2007 | Davison et al. |
| 7,243,509 | B2 | 7/2007 | Trinh et al. |
| 7,264,630 | B1 | 9/2007 | Webb |
| 7,395,554 | B2 | 7/2008 | Kitayama |
| 7,794,486 | B2 | 9/2010 | Quincy, III et al. |
| 8,333,793 | B2 | 12/2012 | Igaki et al. |
| 8,636,786 | B2 | 1/2014 | Biser et al. |
| 8,784,391 | B1 | 7/2014 | Biser |
| D768,306 | S | 10/2016 | Biser et al. |

(56) References Cited

U.S. PATENT DOCUMENTS

| | | | |
|---|---|---|---|
| D783,854 S | 4/2017 | Biser et al. | |
| 9,629,746 B1 | 4/2017 | Biser | |
| 2001/0039442 A1* | 11/2001 | Gorge | A61F 7/02 |
| | | | 607/109 |
| 2004/0138729 A1 | 7/2004 | Ladmer | |
| 2005/0187502 A1 | 8/2005 | Krempel et al. | |
| 2005/0229281 A1 | 10/2005 | Glasser | |
| 2005/0278008 A1 | 12/2005 | Ladmer | |
| 2006/0058840 A1* | 3/2006 | Payne | A61F 13/124 |
| | | | 606/201 |
| 2006/0157064 A1* | 7/2006 | Davison | A61F 9/029 |
| | | | 128/858 |
| 2006/0210616 A1 | 9/2006 | Linder | |
| 2007/0016254 A1 | 1/2007 | Grenon et al. | |
| 2007/0016256 A1 | 1/2007 | Korb et al. | |
| 2007/0022521 A1 | 2/2007 | Seynhaeve et al. | |
| 2007/0027431 A1 | 2/2007 | Korb et al. | |
| 2007/0049913 A1 | 3/2007 | Grenon et al. | |
| 2007/0060988 A1 | 3/2007 | Grenon et al. | |
| 2007/0114422 A1 | 5/2007 | Korb et al. | |
| 2008/0114423 A1 | 5/2008 | Grenon et al. | |
| 2008/0114425 A1 | 5/2008 | Korb et al. | |
| 2008/0114426 A1 | 5/2008 | Korb et al. | |
| 2008/0161892 A1* | 7/2008 | Mercuro | A61F 7/10 |
| | | | 607/109 |
| 2009/0287282 A1 | 11/2009 | Biser | |
| 2009/0287283 A1 | 11/2009 | Biser | |
| 2010/0004569 A1* | 1/2010 | Kim | A61F 7/02 |
| | | | 601/17 |
| 2011/0178585 A1 | 7/2011 | Biser | |
| 2014/0142667 A1 | 5/2014 | Biser et al. | |
| 2014/0331383 A1 | 11/2014 | Bially | |
| 2016/0022480 A1 | 1/2016 | Biser et al. | |

FOREIGN PATENT DOCUMENTS

| | | |
|---|---|---|
| JP | S63-62119 | 4/1988 |
| JP | H10-211228 A | 8/1998 |
| JP | 2000-116430 A | 4/2000 |
| JP | 2004-350803 A | 12/2004 |
| WO | WO 2001/039704 A1 | 6/2001 |
| WO | WO 2009/140673 A1 | 11/2009 |
| WO | WO 2014/144183 A1 | 9/2014 |

OTHER PUBLICATIONS

U.S. Appl. No. 14/179,290, Office Action dated Dec. 23, 2016, 24 pages.
U.S. Appl. No. 14/179,290, Office Action dated Nov. 17, 2017, 36 pages.
U.S. Appl. No. 12/153,322, Office Action dated Jul. 8, 2013, 12 pages.
U.S. Appl. No. 12/153,322, Office Action dated Sep. 12, 2012, 8 pages.
U.S. Appl. No. 12/153,322, Office Action dated Mar. 14, 2012, 11 pages.
U.S. Appl. No. 12/153,322, Office Action dated Jun. 9, 2011, 11 pages.
U.S. Appl. No. 12/153,321, Office Action dated Oct. 8, 2013, 12 pages.
U.S. Appl. No. 12/153,321, Office Action dated Aug. 29, 2012, 11 pages.
U.S. Appl. No. 12/153,321, Office Action dated Jun. 12, 2012, 10 pages.
U.S. Appl. No. 12/153,321, Office Action dated Jun. 9, 2011, 24 pages.
U.S. Appl. No. 12/947,189, Office Action dated Jul. 30, 2012, 10 pages.
U.S. Appl. No. 12/947,189, Office Action dated May 23, 201 10 pages.
U.S. Appl. No. 14/163,598, Office Action dated May 18, 2017, 22 pages.
Office Action dated Jul. 2, 2012 for Chinese Application No. 2009801208470, 8 pages.
Office Action dated Mar. 28, 2013 for Chinese Application No. 2009801208470, 8 pages.
Extended European Search Report dated Jan. 4, 2013 for European Application No. EP 09747754.1, 9 pages.
Office Action dated May 28, 2013 for Japanese Application No. 2011-509789, 9 pages.
International Search Report and Written Opinion for PCT Application No. PCT/US2009/044327, dated Jul. 16, 2009, 8 pages.
International Preliminary Report on Patentability for PCT Application No. PCT/US2009/044327, dated Nov. 17, 2010, 7 pages.
International Search Report and Written Opinion for International Application No. PCT/US2014/028482, dated Aug. 11, 2014.
International Preliminary Report on Patentability for PCT Application No. PCT/US2014/028482, dated Sep. 15, 2015, 7 pages.
"Eyes Pack", Eyes Pack Bilateral Eye Compress; Item# CE-101 Red/CE-102 Green; Corso Enterprises, Inc.; Jan. 17, 2008, pp. 1-6; httg://www.eyespack.corn/eyespack,html.
Brookstone Hot/Cold Antistress Sinus Mask Reviews, [Online] Retrieved from the Internet: <URL: http://www.buzzillions.com/reviews/brookstone-hot-cold-anti-stress-sinus-mask-reviews> [Dec. 8, 2011] (4 pages).
Brookstone Hot/Cold Anti Stress Sinus Mask Description, [Online] Retrieved from the Internet: <URL: http://www.buzzillions.com/reviews/brookstone-hot-cold-anti-stress-sinus-mask-reviews#Description> [Dec. 8, 2011] (1 page).
Corso Enterprises, Inc. "Eyes Pack", [Dec. 3, 2009] [online], [initially retrieved on Jan. 21, 2008] Retrieved from the Internet <URL: http://www.eyespack.com/eyespack.html> (6 pgs).
Dry Eye Talk "Suggestions on Hot Compress while away from home." [online], Post #7 by Rebecca Petris, Administrator, on Apr. 10, 2006, Retrieved from the Internet <URL: http://www.dryeyezone.com/talk/showthread.php?t=1254> (2 pgs).
Dry Eye Talk "thermoeyes" [online], Post #1 by Rebecca Petris, Administrator, on May 3, 2006, Retrieved from the Internet <URL: http://www.dryeyezone.com/talk/showthread.php?t=1339> (2 pgs).
Eye World News Magazine "Reporting Live from New Orleans AAO 2004" Scheffer C.G. Tseng, M.D., Ph.D., "Warming device relieves post-Lasik dry eye, research says" (p. 1) [online], Retrieved from the Internet <URL: http://www.eyeworld.org/article.php?sid=2248&strict=&morphologic=&query=slt> [Dec. 3, 2009] (10 pgs).
Eye Mask, Information about the Eye Comfort Gel Pack, [Online] Retrieved from the Internet: <URL: http://www.accurategelpacks.com/eye_mask.html> [Dec. 8, 2011] (1 page).
Gel Eye Mask (VS-TRM01), [Online] Retrieved from the Internet: <URL: http://hzvison.en.made-in-china.com/product/weEQGmfcqkhH/China-Gel-Eye-Mask-VS-TRM01-.html> [Dec. 8, 2011] (1 page).
Elasto Gel Hot/Cold Sinus Mask, [Online] Retrieved from the Internet: <URL: http://www.amazon.com/Elasto-Hot-Cold-Sinus-Mask/dp/B000FHZNQE/ref=pd_sim_hpc_5> [Dec. 8, 2011] (8 pages).
Make Me Heal "Cold & Hot Eye Compress (w/cheek and temple coverage)" [online], [initially retrieved on Feb. 1, 2008]. Retrieved from the Internet <URL: http://www.makemeheal.com/mmh/product.do; jsessionid=87AE399BAA6CD81AD88A660B0191417C?id=10001&procid=10&catid=30> (3 pgs).
Moist Heat Therapy Warming Eye Pillow by Spa Necessities, [Online] Retrieved from the Internet: <URL: http://www.amazon.com/Moist-Heat-Therapy-Warming-Pillow/dp/B0000ZH3F0?SubscriptionId=1GKMRWT8RXFTWF55P882&tag=lightingelect-20&linkCode=xm2&camp=2025&creative=165953&creativeASIN=B0000ZH3F0> [Dec. 8, 2011] (6 pages).
OCuSOFT Lid Scrub Original Pre-Moistened Pads (30/Ctn), [Online] Retrieved from the Internet: <URL:http://www.ocusoft,com/730-1-90.html> [Dec. 8, 2011] (1 page).
Ophthalmology Management "Enhancing Dry Eye Therapy" [online], Retrieved from the Internet <URL: http://www.ophmanagement.com/article.aspx?article=85198>, [published Sep. 2001] (3 pgs).

(56) References Cited

OTHER PUBLICATIONS

Taiwan Stanch Product—Beauty Series, [Online] Retrieved from the Internet: <URL: http://www.taiwanstanch.com/product_explanationE.asp?kind=90&id=185&Page=1> [Dec. 8, 2011] (1 page).

The Body Shop Eye Gel Mask, [Online] Retrieved from the Internet: <URL: http://www.totalbeauty.com/reviews/product/6096441/the-body-shop-eye-gel-mask> [Dec. 8, 2011] (2 pages).

Thermalon Dry Eye Compress, [Online] Retrieved from the internet: <URL: http://www.amazon.com/Thermalon-24342-Dry-Eye-Compress/dp/B004385RPS/ref=sr_1_1?s=hpc&ie=UTF8&qid=1321925614&sr=1-1> [Dec. 8, 2011](7 pages).

The Dry Eye Zone, "Warm Compresses"[online], [initially retrieved on Feb. 1, 2008]. Retrieved from the Internet: <URL: http://www.dryeyezone.com/encyclopedia/hotcompresses.html> (2 pgs).

Sinclair, Marybetts, "Modern Hydrotherapy for the Massage Therapist", 2008, Lippincott Williams & Wilkins, p. 124 accessed via <URL: https://books.google.com/books?id=fE3YnfgAE_0C&pg=PA124&lpg=PA124&dq=eye+compress+fold+sheet&source=bl&ots%20pg%2012#v=onepage&q=eye%20compress%20fold%20sheet&f=false> [Nov. 17, 2017] (2 pages).

\* cited by examiner

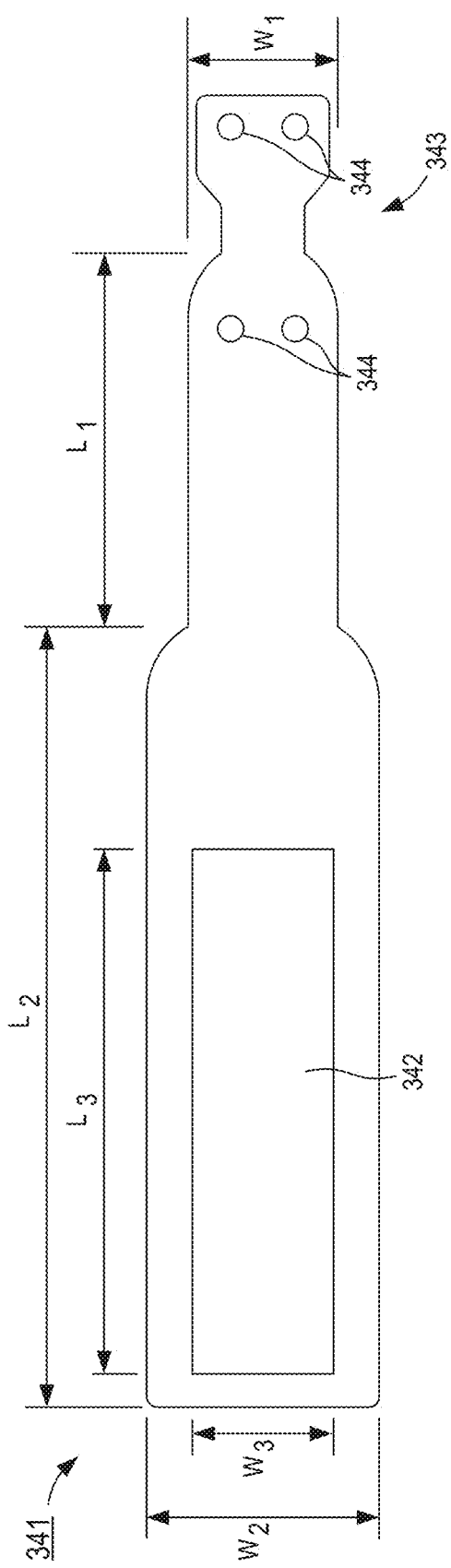
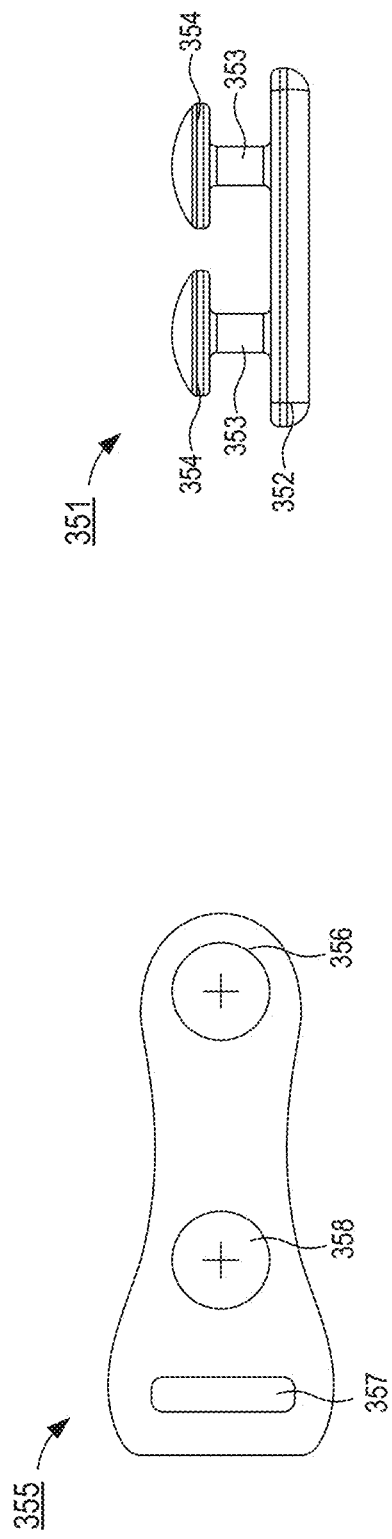
FIG. 14
FIG. 15
FIG. 16

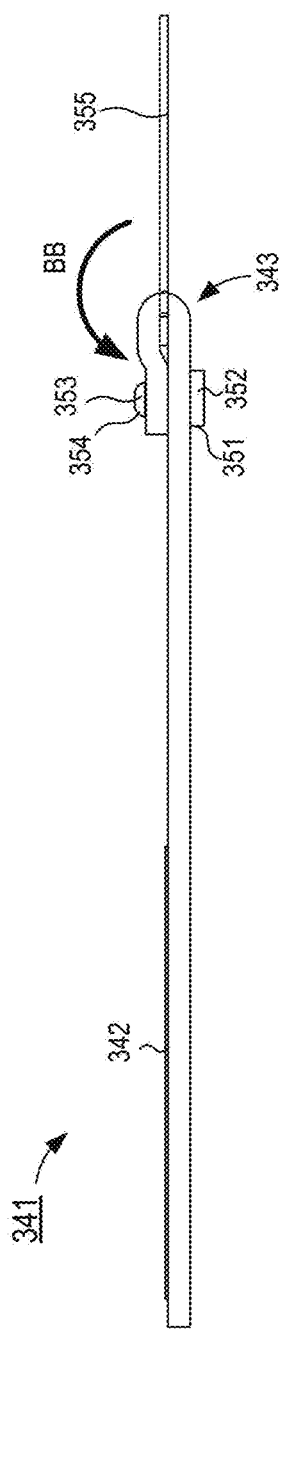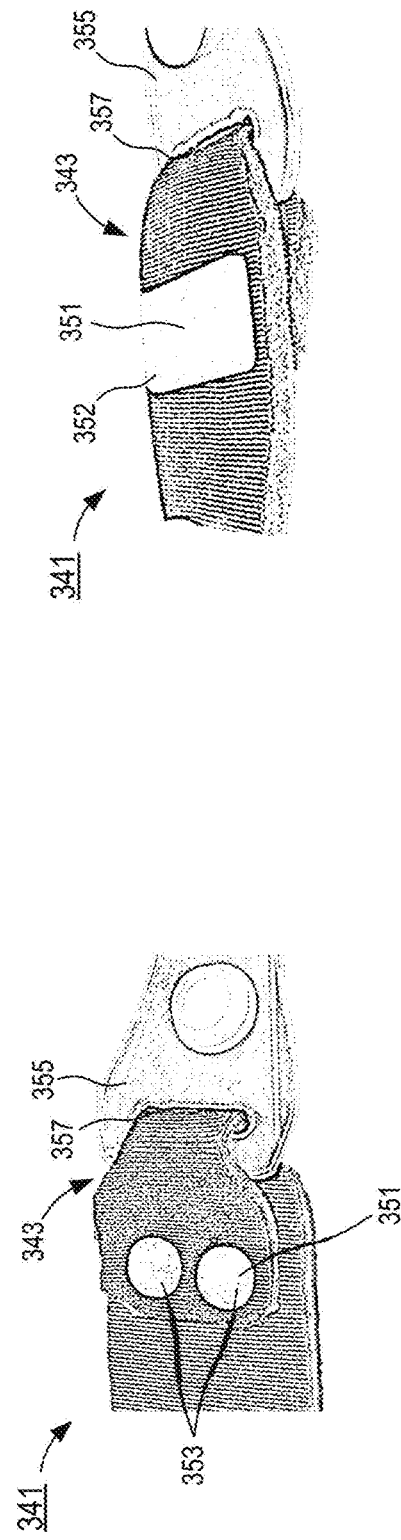
FIG. 20
FIG. 21
FIG. 22

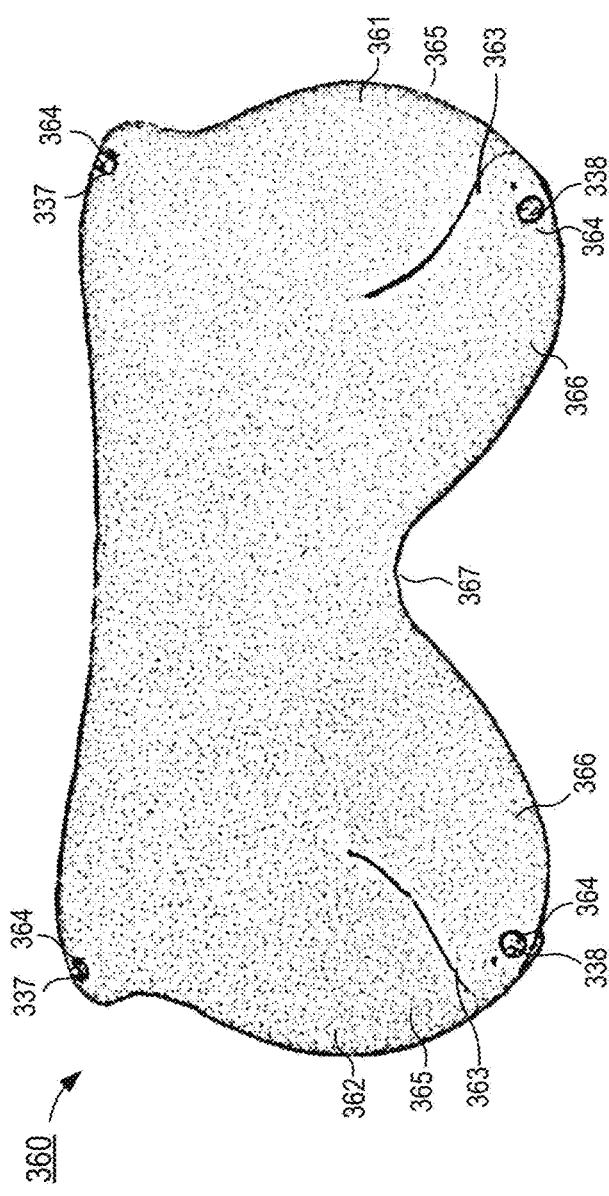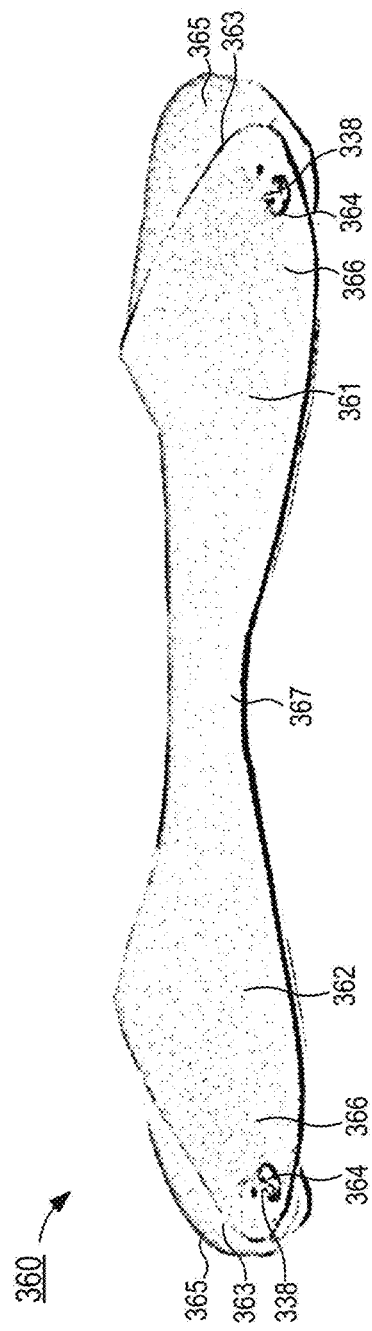

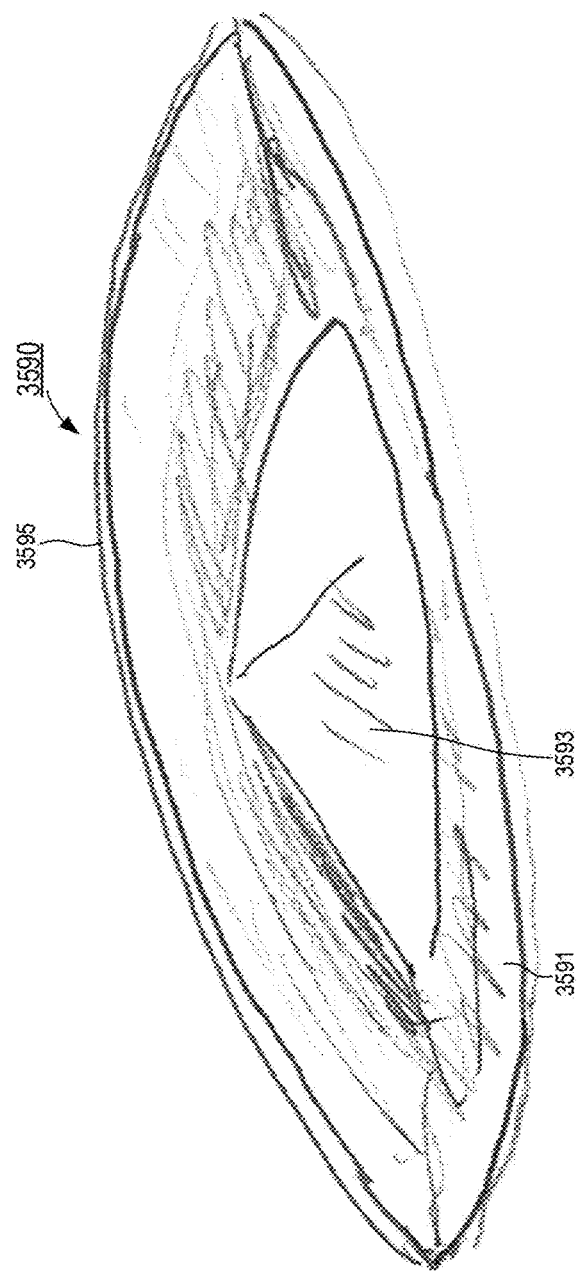

THERMAL EYE COMPRESS SYSTEMS AND METHODS OF USE

CROSS-REFERENCE TO RELATED APPLICATIONS

This application claims priority to and the benefit under 35 U.S.C. § 120 as a Continuation-in-Part (CIP) of U.S. patent application Ser. No. 14/179,290 entitled, "Thermal Eye Compress Systems and Methods of Use," filed Feb. 12, 2014, which (1) claims priority to and the benefit of U.S. Provisional Patent Application Ser. No. 61/852,263 entitled, "Eye Compress Cover and Method of Use," filed Mar. 15, 2013 and U.S. Provisional Patent Application Ser. No. 61/962,067 entitled, "Moistened Disposable Folded Sheets for Use on an Eye Compress, and Methods of Using Same," filed Oct. 30, 2013, and (2) is a CIP of U.S. patent application Ser. No. 14/163,598 entitled, "Thermal Compress System and Methods of Using the Same," filed Jan. 24, 2014, which is a Continuation of U.S. patent application Ser. No. 12/947,189 entitled, "Thermal Compress System and Methods of Using the Same," filed Nov. 16, 2010 (now U.S. Pat. No. 8,636,786), which is a Continuation of International Patent Application Serial No. PCT/US2009/044327 entitled, "Thermal Compress System and Methods of Using the Same," filed May 18, 2009, which is a CIP of (1) U.S. patent application Ser. No. 12/153,321 entitled, "Thermal Bodily Compress Kits and Methods of Using the Same," filed May 16, 2008 and (2) U.S. patent application Ser. No. 12/153,322 entitled, "Thermal Compress Assembly and System With External Frame," filed May 16, 2008, the disclosures of each of which are incorporated herein by reference in their entireties.

This application also claims priority to and the benefit under 35 U.S.C. § 120 as a CIP of U.S. patent application Ser. No. 15/494,574 entitled, "Therapeutic Compress System and Methods of Use," filed Apr. 24, 2017, which is a Continuation of U.S. patent application Ser. No. 14/327,463 entitled, "Therapeutic Compress System and Methods of Use," filed Jul. 9, 2014 (now U.S. Pat. No. 9,629,746), which is a Continuation of U.S. patent application Ser. No. 13/298,445 entitled, "Therapeutic Compress System and Methods of Use," filed Nov. 17, 2011 (now U.S. Pat. No. 8,784,391), which claims priority to and the benefit of U.S. Provisional Patent Application Ser. No. 61/415,153 entitled, "Therapeutic Compress System and Methods of Use," filed Nov. 18, 2010, the disclosures of each of which are incorporated herein by reference in their entireties.

BACKGROUND

The embodiments described herein relate generally to apparatus, systems and methods for applying a therapeutic member to a portion of a user's body. More particularly, the embodiments described herein relate to compress devices, systems, kits and/or methods for providing therapeutic benefit to the eye region of a user by the application or removal of thermal energy, and/or by the application of a therapeutic member.

The application of hot and/or cold compresses is a known therapeutic treatment for some physical ailments. In some instances, a method of thermal compress therapy includes a user holding a cloth (e.g., a washcloth) under hot or cold running water, or in a basin of hot or cold water, and then applying the moist, temperature-adjusted cloth to the desired body part. In some such instances, the cloth is maintained in contact with the desired body part through manual intervention (e.g., the user holds the cloth in place). In some instances, a user may not be able to maintain the position of the cloth due to an ailment and/or impairment (e.g., arthritis or the like).

In other instances, a thermal pack can be heated or cooled, and applied against a body part of the user. Some such thermal packs can be filled with gelatinous substances that can conform to the anatomy under gentle pressure. For example, in some instances, a thermal pack can be used to apply thermal energy to or remove thermal energy from the eye region of the user. In some embodiments, the thermal packs can be included in a device that includes a frame configured to support the thermal packs and a strap system configured to retain the thermal packs in a fixed position relative to the eye region of the user. The anatomy of the eye region, however, can result in challenges to the application of thermal packs. For example, the contour of the eye region can result in challenges to placing the thermal packs in contact with the eye region with a relatively consistent and comfortable amount of force. As such, the level of discomfort and/or ineffective application or removal of thermal energy can, in some instances, deter a user from using some such devices.

Thus, a need exists for improved compress devices, systems, kits, and methods for providing therapeutic benefit to, for example, sensitive portions of the body such as the eye region, by the application or removal of thermal energy and/or by the application of a therapeutic member.

SUMMARY

Apparatus, systems, and methods for providing therapeutic benefit to the eye region of a user by the application or removal of thermal energy and/or by the application of a therapeutic member are described herein. In some embodiments, an apparatus includes a flexible frame, a coupling portion, and an insulating portion. The flexible frame is configured to support a thermal therapeutic member and is transitioned between a first configuration and a second configuration to place the therapeutic member in substantially continuous contact with a target portion of the body. The coupling portion is coupled to the flexible frame and is transitioned from a first configuration to a second configuration to retain the flexible frame in its second configuration. The insulating portion is transitioned from a first configuration to a second configuration to be coupled to the flexible frame. The insulating portion at least partially controls a transfer of thermal energy between the thermal therapeutic member and the target portion of the body.

BRIEF DESCRIPTION OF THE DRAWINGS

FIG. 14 is a schematic illustration of a strap included in the coupling portion of FIG. 13.

FIG. 15 is a schematic illustration of a coupling member included in the coupling portion of FIG. 13.

FIG. 16 is a schematic illustration of a closure member included in the coupling portion of FIG. 13.

FIG. 20 is a schematic illustration of the strap of FIG. 13 in a third configuration.

FIGS. 21 and 22 are a rear perspective view and a front perspective view, respectively, of the portion of the strap illustrated in FIGS. 18 and 19 in the third configuration.

FIGS. 29 and 30 are a front view and a bottom view, respectively, of the first insulating member of FIGS. 23 and 24 in a second configuration and coupled to the flexible frame of FIGS. 5 and 6.

FIG. 106 is a perspective view of the therapeutic device of FIG. 105 disposed in the shipping package of FIG. 104, in a second configuration.

DETAILED DESCRIPTION

Figure 1:
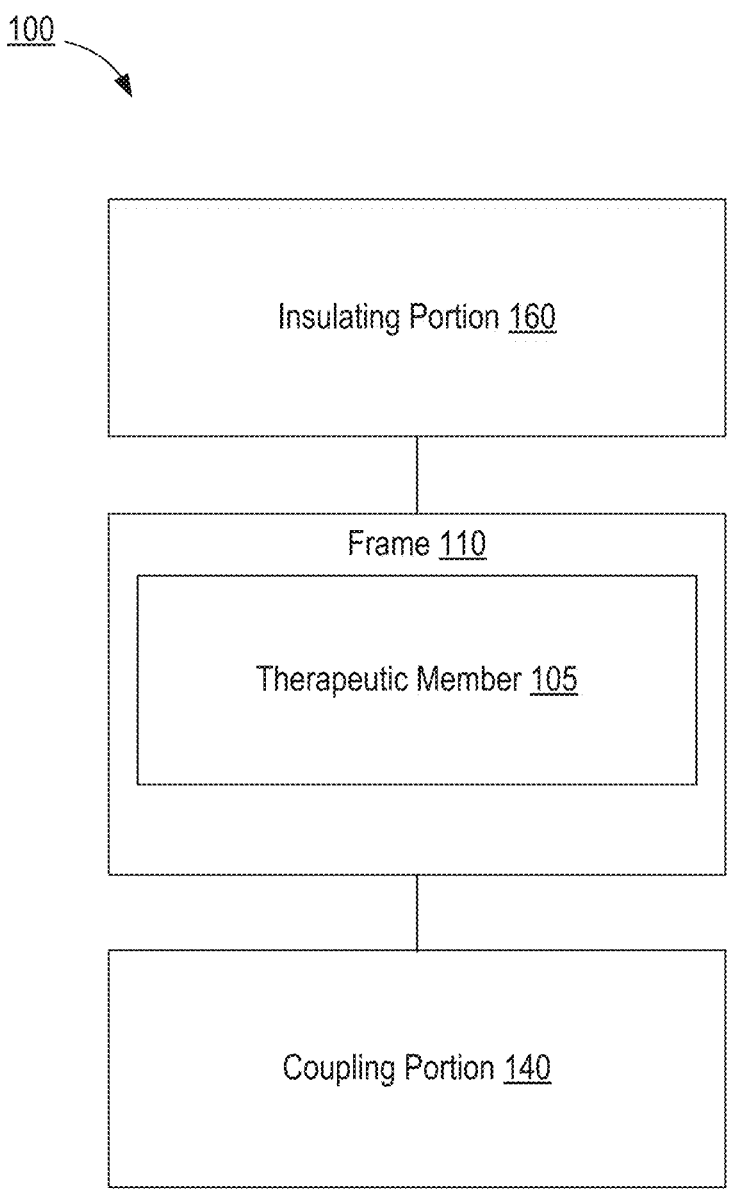
FIG. 1 is a schematic illustration of a therapeutic device according to an embodiment.

In some embodiments, an apparatus includes a flexible frame, a coupling portion, and an insulating portion. The flexible frame is configured to support a thermal therapeutic member and is transitioned between a first configuration and a second configuration to place the therapeutic member in substantially continuous contact with a target portion of the body. The coupling portion is coupled to the flexible frame and is transitioned from a first configuration to a second configuration to retain the flexible frame in its second configuration. The insulating portion is transitioned from a first configuration to a second configuration to be coupled to the flexible frame. The insulating portion at least partially controls a transfer of thermal energy between the thermal therapeutic member and the target portion of the body.

The embodiments described herein can include and/or can form at least a portion of a therapeutic device (e.g., a thermal compress device, system, and/or kit) that can be used to treat or alleviate a variety of abnormal physiological conditions in users, or to provide therapeutic benefit to users who are otherwise in normal condition. The devices and methods can be applied to various body parts such as, for example, soft tissues, muscles, bones, and other tissues and organs of a user. Although the embodiments and methods are described herein as being associated with and/or applied to, for example, an ocular region of a user, in other instances, the embodiments and methods can be associated with and/or applied to any suitable part of the anatomy. Accordingly, the embodiments described herein are not to be construed as being limited only to use in treatments of the eye or ocular region of a user. The embodiments can be adapted to any use in which thermal or other surface treatment is to be provided by contacting a body part of a user with a portion of a device that can transfer thermal energy to or receive thermal energy from the body part, and/or that can transfer a therapeutic member other than thermal energy to the body part.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the value stated. For example, about 0.5 would include 0.45 and 0.55, about 10 would include 9 to 11, about 1000 would include 900 to 1100. In addition, the terms about and approximately can be context specific. For example, if a function is being performed, the term about when used in the context of the function so defined can include any or all variations of the function while still performing that function.

As used herein, the term "set" can refer to multiple features or a singular feature with multiple parts. For example, when referring to a set of walls, the set of walls can be considered as one wall with multiple portions, or the set of walls can be considered as multiple, distinct walls. Thus, a monolithically constructed item can include a set of walls. Such a set of walls may include multiple portions that are either continuous or discontinuous from each other. A set of walls can also be fabricated from multiple items that are produced separately and are later joined together (e.g., via a weld, an adhesive, or any suitable method).

As used herein, the term "stiffness" is related to an object's resistance to deflection, deformation, and/or displacement that is produced by an applied force, and is generally understood to be the opposite of the object's "flexibility." For example, a wall with greater stiffness is more resistant to deflection, deformation and/or displacement when exposed to a force than a wall having a lower stiffness. Similarly stated, an object having a higher stiffness can be characterized as being more rigid than an object having a lower stiffness. Stiffness can be characterized in terms of the amount of force applied to the object and the resulting distance through which a first portion of the object deflects, deforms, and/or displaces with respect to a second portion of the object. When characterizing the stiffness of an object, the deflected distance may be measured as the deflection of a portion of the object different from the portion of the object to which the force is directly applied. Said another way, in some objects, the point of deflection is distinct from the point where force is applied.

Stiffness (and therefore, flexibility) is an extensive property of the object being described, and thus is dependent upon the material from which the object is formed as well as certain physical characteristics of the object (e.g., cross-sectional shape, length, boundary conditions, etc.). For example, the stiffness of an object can be increased or decreased by selectively including in the object a material having a desired modulus of elasticity, flexural modulus and/or hardness. The modulus of elasticity is an intensive property of (i.e., is intrinsic to) the constituent material and describes an object's tendency to elastically (i.e., nonpermanently) deform in response to an applied force. A material having a high modulus of elasticity will not deflect as much as a material having a low modulus of elasticity in the presence of an equally applied stress. Thus, the stiffness of the object can be decreased, for example, by introducing into the object and/or constructing the object of a material having a relatively low modulus of elasticity.

In another example, the stiffness of the object can be increased or decreased by changing the flexural modulus of a material of which the object is constructed. Flexural modulus is used to describe the ratio of the applied stress on an object in flexure to the corresponding strain on the outermost portions of the object. The flexural modulus, rather than the modulus of elasticity, is used to characterize certain materials, for example plastics, that do not have material properties that are substantially linear over a range of conditions. An object with a first flexural modulus is less elastic and has a greater strain on the outermost portions of the object than an object with a second flexural modulus lower than the first flexural modulus. Thus, the stiffness of an object can be increased by including in the object a material having a high flexural modulus.

The stiffness of an object can also be increased or decreased by changing a physical characteristic of the object, such as the shape or cross-sectional area of the object. For example, an object having a length and a cross-sectional area may have a greater stiffness than an object having an identical length but a smaller cross-sectional area. As another example, the stiffness of an object can be reduced by including one or more stress concentration risers (or discontinuous boundaries) that cause deformation to occur under a lower stress and/or at a particular location of the object. Thus, the stiffness of the object can be decreased by decreasing and/or changing the shape of the object.

As used herein, certain components and/or aspects of the embodiments can be identified and/or located with the adjectives "top," "upper," "bottom," "lower," "left," "right," "front," "rear," etc. These adjectives are provided in the context of use of a compress system in therapy of the eye region of a user, and in the context of the orientation of the drawings that show an upright human user. In this context, the terms "top," "bottom," "left," "right," "front," and "back" refer to the orientation of the compress system in relation to the user, in an applied position on the user's face when the user is standing upright (a position known as the "anatomical position") unless explicitly stated otherwise. The compress systems disclosed herein can be worn by a user in any number of positions, including, for example, an upright (sitting or standing) or recumbent position.

Relationships and orientations associated with the components of the embodiments herein may also be described in ways that are common in anatomic medical terminology. For example, the terms "lateral" and "temporal" are used to indicate a location substantially at or along a side portion of the body, while the terms "medial" and "nasal" are used to indicate a location substantially at or along a longitudinal centerline of the body. The terms "superior" and "inferior" can be used to describe an upper or top location and a lower or bottom location, respectively, relative to the body. Similarly, the terms "anterior" and "posterior" can be used to describe a forward location or rearward location, respectively, relative to the body. Moreover, when used in reference to positions on or along the embodiments described herein, the terms "peripheral," "outer," and/or "distal" can refer to a position that is disposed at, along and/or relatively closer to a perimeter of the embodiment, while the terms "central," "inner," and/or "proximal" can refer to a position that is disposed at, along, and/or relatively closer to a center of the embodiment.

FIG. 1 is a schematic illustration of a therapeutic device 100 according to an embodiment. The therapeutic device 100 (also referred to herein as "eye compress device" or "eye compress system") can be used to place a therapeutic member in contact with a target region of the body of a user such as, for example, the ocular region of the face of the user. The therapeutic device 100 includes a flexible frame 110, a coupling portion 140, and an insulating portion 160. The flexible frame 110 is configured to support and/or otherwise be coupled to a therapeutic member 105. The therapeutic member 105 can be any suitable configuration. For example, in some embodiments, the therapeutic member 105 can be a thermal gel pack or the like. In such embodiments, the user can place a surface of the thermal gel pack in contact with, for example, the ocular region of the face and in turn, the thermal gel pack can transfer thermal energy to or receive thermal energy from the ocular region. More specifically, the therapeutic member 105 can include a substantially viscous material or combination of materials that can be heated or cooled to provide thermal energy to or receive thermal energy from, respectively, the body.

In some embodiments, the therapeutic member 105 can include a flexible pouch or the like that can deform when exposed to an external force. Thus, when the therapeutic member 105 is placed in contact with, for example, the ocular region of the patient, the therapeutic member 105 can elastically deform (e.g., nonpermanently deform), bend, flex, or otherwise reconfigure in such a manner that a surface area in contact with the ocular region is greater than a surface area of a substantially rigid or inflexible therapeutic member that is placed in contact with the ocular region. In some embodiments, the therapeutic member 105 can define a single inner volume such that when the therapeutic member 105 is placed in contact with the ocular region, a single volume of thermal gel can transfer thermal energy to or receive thermal energy from at least a portion of the ocular region being treated. For example, in some embodiments, the therapeutic member 105 can define a single inner volume such that when the therapeutic member 105 is placed in contact with the ocular region, a single volume of thermal gel can transfer thermal energy to or receive thermal energy from both the left eye and the right eye of the ocular region. Similarly stated, the therapeutic member 105 can be arranged such that a volume of thermal gel that transfers thermal energy to and/or receives thermal energy from the left eye of the user is in fluid communication with a volume of thermal gel that transfers thermal energy to and/or receives thermal energy from the right eye of the user.

The flexible frame 110 (also referred to herein as "frame") is coupled to the coupling portion 140 and the insulating portion 160 and supports and/or is at least temporarily coupled to the therapeutic member 105. For example, in some embodiments, the frame 110 can include and/or define a set of snaps, buttons, protrusions, apertures, surfaces, etc. that can be matingly coupled to a corresponding set of snaps, buttons, protrusions, apertures, surfaces, etc. included in and/or defined by the therapeutic member 105. Specifically, in some embodiments, the frame 110 can include a set of snaps that can matingly engage a corresponding set of snaps included in the therapeutic member 105 to removably couple the therapeutic member 105 to the frame 110.

The frame 110 can be any suitable shape, size, or configuration. For example, in some embodiments, the flexible frame 110 can have a size and shape that is associated with at least a portion of the ocular region of the user. In such embodiments, the frame 110 can include a first lobe and a second lobe that can substantially correspond to a first eye and a second eye of the user. Thus, when the therapeutic member 105 is coupled to the frame 110 and the therapeutic member 105 is placed in contact with the ocular region of the user, the frame 110 can support the therapeutic member 105 to maintain a surface of the therapeutic member 105 in contact with, for example, the left eye region and the right eye region of the user. Moreover, in some embodiments, the first lobe and the second lobe can each define an aperture that can reduce the stiffness of the frame 110 and/or that can provide a portion of the frame 110 which can provide other means for enhancing the experience of the user, when the therapeutic device 100 is disposed about the ocular region. In some embodiments, for example, a portion of the therapeutic member 105 can be configured to extend anteriorly through the apertures such that when the therapeutic member 105 is placed in contact with the ocular region of the user, a force exerted by the therapeutic member 105 directly on the globe of the eye (and/or eye lid) is reduced. In other embodiments, the frame 110 can be substantially solid (e.g., the frame 110 does not define the apertures). Although the frame 110 is described above as supporting the therapeutic member 105 that is in contact with both the left eye and the right eye, in other embodiments, the frame 110 can support a therapeutic member that is in contact with a single eye (i.e., the left eye or the right eye) of the user.

The flexible frame 110 can be formed from any suitable material such as one or more polymers (e.g., plastics). Examples of suitable polymers can include polylactides, polyglycolides, polylactide-co-glycolides (PLGA), polyanhydrides, polyorthoesters, polyetheresters, polycaprolactones, polyesteramides, poly(butyric acid), poly(valeric acid), polyurethanes, nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, low density polyethylene (LDPE), high density polyethylene (HDPE) and/or blends or copolymers thereof. As such, the frame 110 can have a stiffness that can allow the frame 110 to bend, flex, elastically deform, and/or otherwise reconfigure between a first, undeformed configuration and a second, deformed configuration when exposed to an external force. More specifically, the frame 110 can have a stiffness that is sufficiently low to allow the frame 110 to transition from the first configuration to the second configuration (e.g., bend and/or deform in at least one plane when exposed to an external force) to place a surface of the therapeutic member 105 in contact with the ocular region of the user. In some embodiments, when the frame 110 is in the second configuration and when the therapeutic device 100 is coupled to a portion of the body, a force exerted by the therapeutic member 105 is distributed along the portion of the body so as to aid in a reduction of discomfort for the user, and/or to increase a surface area of the therapeutic member 105 that is in contact with the portion of the body of the user, as described in further detail herein.

The coupling portion 140 of the therapeutic device 100 is coupled to the frame 110 and can be transitioned between a first configuration and a second configuration to removably couple the therapeutic device 100 to the user. The coupling portion 140 can be any suitable shape, size, or configuration. For example, in some embodiments, the coupling portion 140 can be one or more straps coupled to the frame 110 and configured to be transitioned between a first configuration and a second configuration. More specifically, in some embodiments, the coupling portion 140 can include a first strap (not shown in FIG. 1) coupled to a first side of the frame 110 and a second strap (not shown in FIG. 1) coupled to a second side of the frame 110. In such embodiments, the first strap can include a portion that can engage a corresponding portion of the second strap to removably couple the first strap to the second strap, thereby placing the coupling portion in its second configuration. For example, in some embodiments, the first strap and the second strap can define a hook-and-loop coupling (e.g., Velcro®). In this manner, when in the second configuration a portion of the first strap can overlap a portion of the second strap (or vice versa) in such a way that a surface of the first strap engages a surface of the second strap to form the hook-and-loop coupling. In some embodiments, the coupling portion 140 can be arranged such that the relatively soft surface formed by the loop portion is oriented towards the user, while the relatively rigid surface formed by the hook portion is oriented away from the user.

Thus, the therapeutic device 100 can be placed in a desired position relative to the ocular region of the user and the coupling portion 140 can be transitioned from its first configuration to its second configuration to substantially maintain the therapeutic device 100 in the desired position relative to the ocular region. Expanding further, the first strap and the second strap of the coupling portion 140 can extend in a posterior direction from the frame 110, can be looped around the head of the user, and can be coupled together to maintain the therapeutic device 100 in a substantially fixed position relative to the head of the user. The arrangement of the coupling portion 140 can be such that the portion of the first strap that engages the portion of the second strap is adjustable. That is to say, when in the second configuration, the part of the coupling portion 140 that is overlapping can be increased or decreased. More specifically, an area that is circumscribed by the therapeutic device 100 can be increased or decreased by decreasing or increasing, respectively, an overlapping region of the coupling portion 140. Thus, the coupling portion 140 can couple the therapeutic device 100 to users with different sized anatomy (e.g., heads).

In some embodiments, at least a part of the coupling portion 140 can formed from a relatively flexible material (e.g., an elastic material) that can be stretched, for example, from an undeformed configuration (e.g., having an initial length) to a deformed configuration (e.g., having a relatively longer length). In such embodiments, a user can place at least a part of the coupling portion 140 in the deformed configuration (e.g., by stretching at least a part of the coupling portion 140) to, for example, increase a tension within at least the part of the coupling portion 140. Thus, in some instances, a user can increase an overlapping region of the coupling portion 140 which can, for example, increase a tension within the coupling portion 140 that can be operable in coupling the therapeutic device 100 to the patient, as described in further detail herein.

Although the first strap and the second strap are described above as forming a hook-and-loop coupling, in other embodiments, the first strap can include and/or can define a set of snaps, buttons, protrusions, apertures, clamps, etc. that can engage a corresponding set of snaps, buttons, protrusions, apertures, clamps, etc. included in and/or defined by the second strap. In still other embodiments, the coupling portion 140 can include a single elastic strap that can be transitioned from a first, substantially undeformed configuration to a second, substantially deformed configuration (e.g., stretched).

The arrangement of the therapeutic device 100 can be such that the frame 110 and the coupling portion 140 substantially circumscribe the anatomy of the user. More particularly, the coupling portion 140 can be placed in the second configuration to couple the therapeutic device 100 to the head of the user such that the thermal agent 105 is placed in contact with the ocular region. In some embodiments, the coupling portion 140 can be selectively placed in the second configuration such that a desired amount of force is exerted by the therapeutic device 100 on the head of the user. For example, as described above, the coupling portion 140 can be placed in the second configuration to circumscribe a given area that can substantially correspond to a perimeter of the head of the user. Therefore, when the therapeutic member 105 is placed in contact with the ocular region of the user and the coupling portion 140 is adjusted (e.g., adjusted to increase the tension in the coupling portion 140, for example, by stretching at least a part of the coupling portion 140 such that an overlapping area thereof is increased, as described above), a force exerted by the therapeutic device 100 on the head of the user is increased. Conversely, the coupling portion 140 can be adjusted to decrease the tension in the coupling portion 140, for example, by decreasing an overlapping area of the coupling portion 140 such that a force exerted by the therapeutic device 100 on the head of the user is decreased. Thus, the coupling portion 140 can be placed in its second configuration such that a desired amount of force (as determined by the user) is exerted by the therapeutic member 105 on the ocular region of the user. Moreover, the force exerted by the therapeutic device 100 on the head of the user can be sufficient to place the frame 110 in its second configuration (e.g., can deform the frame 110). As such a force that is, in turn, exerted by the therapeutic member 105 is distributed on the ocular region as to increase the comfort of the user and/or to increase the surface area of the therapeutic member 105 that is in contact with the ocular region, than would otherwise be possible.

The insulating portion 160 of the therapeutic device 100 can be any suitable shape, size, or configuration and can be formed from any suitable insulating material or combination thereof. For example, in some embodiments, the insulating portion 160 can be formed from a relatively thin neoprene-foam fabric material. More specifically, the insulating portion 160 can include a neoprene-foam core that is surrounded by a fabric such as, for example, spandex (e.g., Lycra®), or the like. In other embodiments, the insulating portion 160 can be formed from, for example, polyester, polyethylene terephthalate, polyester-olefin, polyester microfibers, and/or the like. In other embodiments, the insulating portion 160 can be formed from a fabric, such as a fabric derived from natural materials including felts, wools, heavy-gauge cotton, nylon fabrics, foams, plastics, woven and nonwoven materials, and/or the like.

As described above, the insulating portion 160 can be coupled to the frame 110. More specifically, the insulating portion 160 can be transitioned from a first configuration to a second configuration to be removably coupled to the frame 110. In some embodiments, the insulating portion 160 can be substantially flat (e.g., substantially planar) when in its first configuration and can be transitioned to its second configuration in which the insulating portion 160 includes and/or defines one or more convex portions. In some embodiments, the insulating portion 160 can define a deformable portion that can be moved relative to a surface of the insulating portion 160 to place the insulating portion 160 in the second configuration. For example, in some embodiments, the insulating portion 160 can define a cut that can allow a first portion disposed on a first side of the cut to be folded onto a second portion disposed on a second side of the cut and substantially opposite the first side. In this manner, the insulating portion 160 can be transitioned from its first configuration to its second configuration in which the deforming of the insulating portion 160 results in a tenting having a convex and/or conical shape. In some embodiments, the insulating portion 160 can be placed in its second configuration to form two convex portions that substantially correspond to the first lobe and the second lobe (described above) of the frame 110. In some embodiments, the convex portions of the insulating portion 160 can substantially correspond to the portions of the therapeutic member 105 that extend through the apertures defined by the frame 110, as described above.

The insulating portion 160 can be coupled to the frame 110 via any suitable coupling. For example, in some embodiments, the insulating portion 160 can define a set of apertures that can each receive a protrusion or post that extends from an anterior surface of the frame 110. Furthermore, the arrangement of the insulating portion 160 can be such that when in the second configuration a first aperture on a first side of the cut (described above) and a second aperture on a second side of the cut are substantially aligned. Thus, the first aperture and the second aperture can be configured to receive the same protrusion or post that extends from the anterior surface of the frame 110. In some embodiments, the protrusions can include an end portion that can be flared or flanged such that when disposed in an aperture defined by the insulating portion 160, the protrusions can maintain the insulating portion 160 in the second configuration to couple the insulating portion 160 to the frame 110.

With the insulating portion 160 coupled to the frame 110, the insulating portion 160 can substantially reduce the transfer of thermal energy from an anterior surface of the therapeutic member 105 in an anterior direction. For example, the convex portions formed by the insulating portion 160 can be configured to surround at least a portion of the anterior surface of the therapeutic member 105. In this manner, surrounding at least the portion of the anterior surface of the therapeutic member 105 reduces thermal energy transfer that would otherwise be transferred from or to the anterior surface of the therapeutic member 105 (e.g., due to convection heat transfer or the like).

While the insulating portion 160 is described as being disposed in an anterior position relative to the frame 110, in some embodiments, the insulating portion 160 can include a second insulating member (not shown in FIG. 1) that can be disposed in a posterior position relative to the therapeutic member 105. For example, in some embodiments, the second insulating member can be a relatively thin sheet or fabric that can be placed onto or coupled to a posterior or anterior surface of the frame 110 and/or a posterior surface of the therapeutic member 105. In some embodiments, the second insulating member (also referred to herein as "sheet") can include a portion that includes, for example, an adhesive or the like that can couple the second insulating member to the frame 110 and/or the therapeutic member 105. In some instances, the second insulating member can have a moisture content that can enhance the transfer of thermal energy between the ocular region of the user and the therapeutic member 105. In some instances, the second insulating member can enhance the comfort of the user while using the therapeutic device 100. For example, in some embodiments, the second insulating member can be disposed relative to the therapeutic member 105 to cover an edge of thereof and/or to cover a coupling member configured to couple the therapeutic member 105 to the frame 110 (or vice versa), that could otherwise contact the user.

In use, the therapeutic member 105 can be coupled to the frame 110 and can be configured to, for example, receive thermal energy. For example, in some embodiments, the therapeutic device 100 can be placed in a microwave oven, disposed in hot water, positioned in a heating device, electrically connected to an electrical source, and/or the like such that the potential thermal energy of the therapeutic member 105 is increased. In some instances, the insulating portion 160 can be coupled to the frame 110 or to the therapeutic member 105 after the thermal energy is transferred to the therapeutic member 105. In other instances, the insulating portion 160 can be coupled to the frame 110 or to the therapeutic member 105 prior to thermal energy being transferred to the therapeutic member 105. With the thermal energy transferred to the therapeutic member, the user can move the therapeutic device 100 to place the therapeutic member 105 in contact with, for example, the ocular region. Once in the desired position, the coupling portion 140 can be transitioned from its first configuration to its second configuration to couple the therapeutic device 100 to the head of the user. Thus, thermal energy can be transferred from the therapeutic member 105 to the ocular region. Moreover, the arrangement of the therapeutic device 100 can be such that the transfer of the thermal energy is substantially uniform on a desired target area of the ocular region. In addition, the force exerted by the therapeutic member 105 on the ocular region can be distributed and/or diffused in such a manner as to increase the comfort of the user while using the therapeutic device 100.

Figure 2:
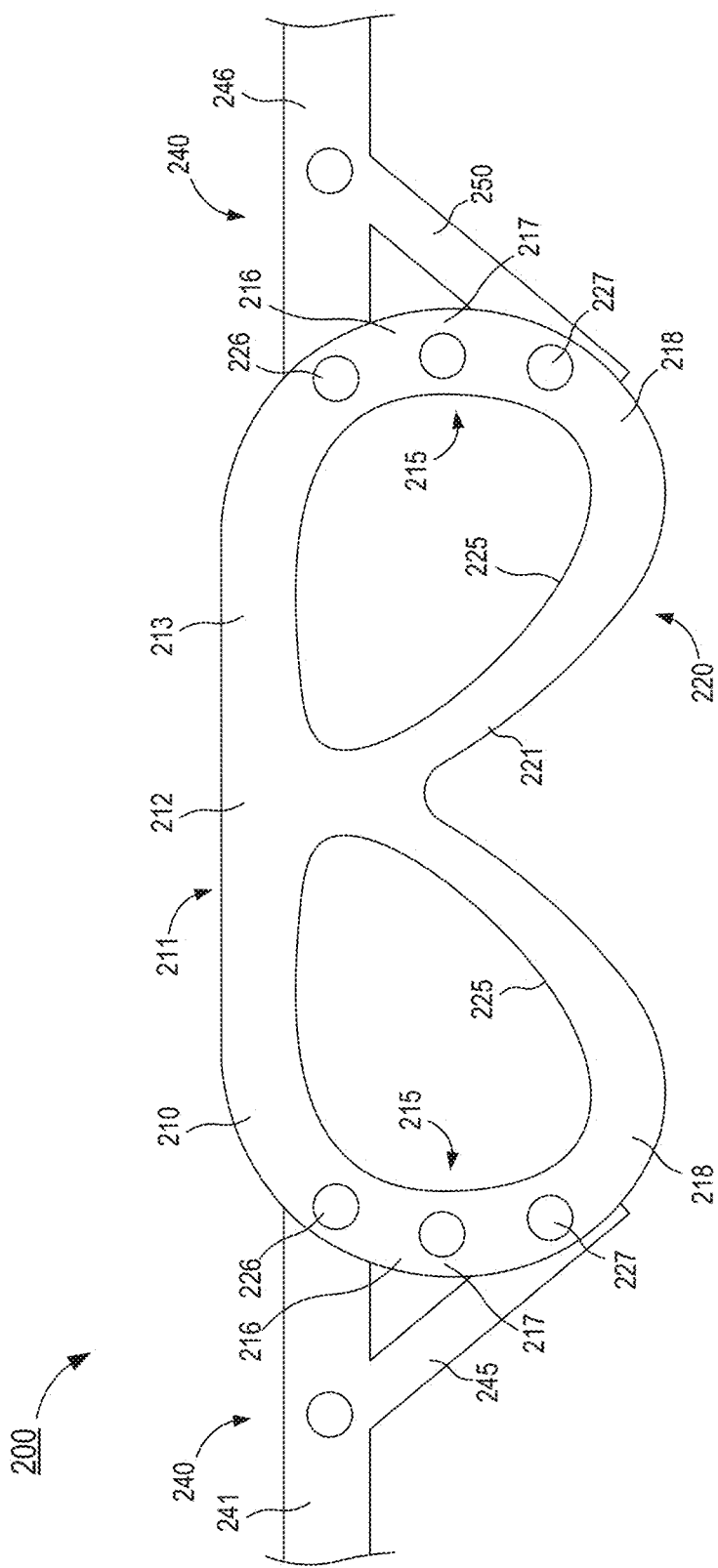
FIG. 2 is a schematic illustration of a therapeutic device according to another embodiment.

FIG. 2 illustrates at least a portion of a therapeutic device 200 according to another embodiment. The therapeutic device 200 can be used to place a therapeutic member in contact with a target region of the body of a user such as, for example, the ocular region of the face of the user. The therapeutic device 200 (also referred to herein as "eye compress device" or "eye compress system") includes a flexible frame 210 and a coupling portion 240 having a V-shaped strap system with a first strap 241 and a second strap 246. The flexible frame 210 is configured to support and/or otherwise to be coupled to a therapeutic member (not shown in FIG. 2). The therapeutic member can be any suitable configuration. For example, in some embodiments, the therapeutic member can be a thermal gel pack or the like. In some embodiments, the therapeutic member can be substantially similar to or the same as the therapeutic member 105 described above with reference to FIG. 1. Thus, the therapeutic member is not described in further detail herein.

As described above, the V-shaped strap system 240 (also referred to herein as "coupling portion") includes the first strap 241 and the second strap 246. The first strap 241 and the second strap 246 extend in a substantially perpendicular direction from the flexible frame 210. The first strap 241 includes an inferior member 245 that extends at an angle from the first strap 241 to form a V-shape. In some embodiments, the inferior member 245 is coupled to the first strap 241 (e.g., via a snap fit, rivet, or the like) in such a manner that the inferior member 245 can pivot or rotate relative to the first strap 241. In other embodiments, the inferior member 245 is monolithically formed with the first strap 241. Moreover, the flexible frame 210 includes a first attachment point 226 to which an end portion of the first strap 241 is coupled and a second attachment point 227 to which an end portion of the inferior member 245 is coupled. In some embodiments, the first strap 241 and/or the inferior member 245 can be rotatably coupled to the first attachment point 226 and/or the second attachment point 227, respectively. Thus, in some embodiments, the first strap 241 and the inferior member 245 can pivot relative to the flexible frame 210. Similarly, the second strap 246 includes an inferior member 250 that extends at an angle from the second strap 246 to form the V-shape. The second strap 246 and the inferior member 250 are coupled to a first attachment point 226 and a second attachment point 227, respectively, of the corresponding side portion 215 in a similar manner as described above with reference to the first strap 241 and the inferior member 245.

The flexible frame 210 (also referred to herein as "frame 210") can be monolithically formed from a relatively flexible material such as those described above with reference to the frame 110 of FIG. 1. The frame 210 can be transitioned from a first configuration to a second configuration when the therapeutic device 200 is coupled to the body, as described in further detail herein. The frame 210 has a top portion 211 including a top central region 212 and superior regions 213 (relative to the user's eye); a side portion 215 including a superotemporal region 216 disposed at about a midpoint between the first attachment points 226 and the second attachment points 227, an inferotemporal region 218, and a centrolateral region 217 disposed at about a midpoint between a top edge of the frame 210 and a bottom edge of the frame 210; and an inferior portion 220 including an inferomedial region 221. The frame 210 also defines a set of apertures 225. For example, as shown in FIG. 2, the frame 210 includes two apertures 225 that correspond to the left eye region and the right eye region of the user. Although portions of the frame 210 are specifically described, certain areas, portions, and/or regions of frame 210 can overlap with other areas, portions, and regions, such that there is no clear delineation between one area, portion, or region, and its contiguously adjoining area, portion, or region. That is to say, while specific portions are described, the union, intersection, and/or transition between adjacent portions need not signify a substantial change in a physical property of the frame 210.

Figure 3:
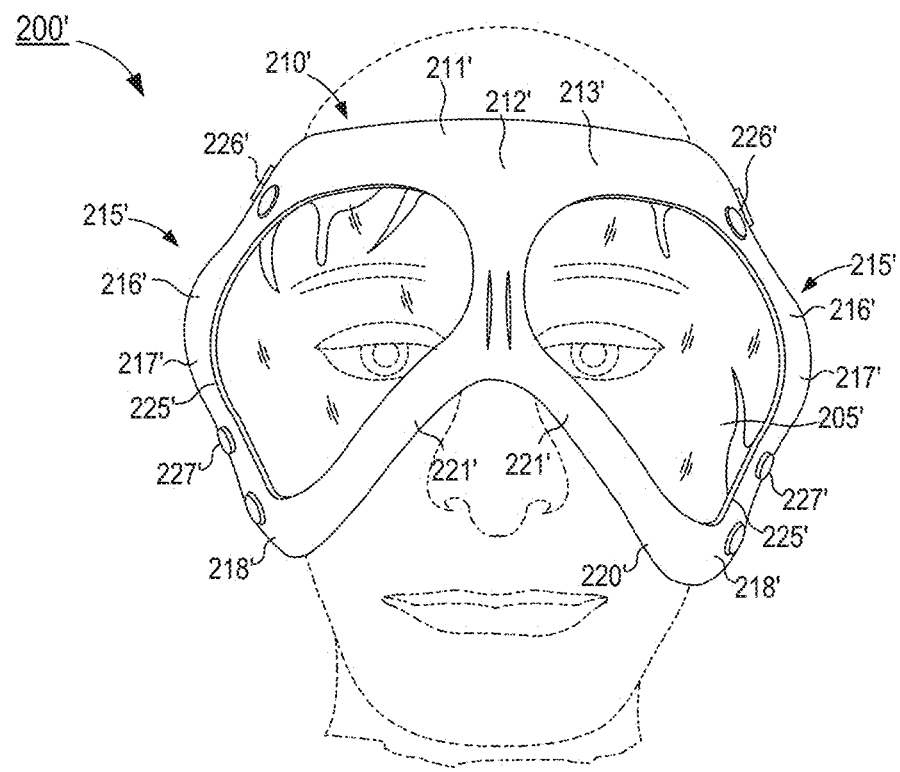
FIGS. 3 and 4 are a front schematic illustration and a right side schematic illustration, respectively, according to another embodiment coupled to a portion of the body.
Figure 4:
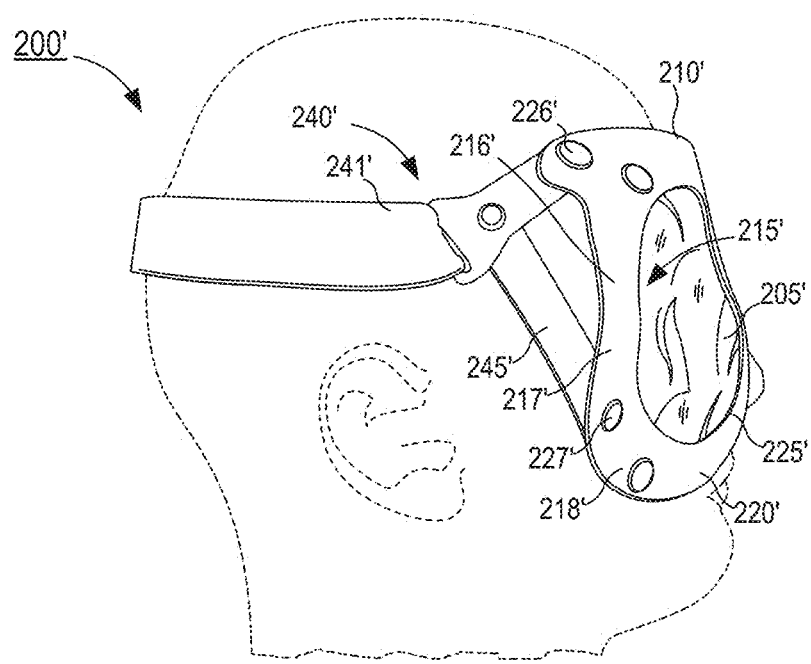

In some embodiments, the frame 210 of the therapeutic device 200 can be configured to increase a convex bend in a portion of the frame 210 when the frame 210 is applied to a user's face. For example, as shown in FIGS. 3 and 4, in some embodiments, a therapeutic device 200' can be positioned adjacent to the face of a user and transitioned between a first configuration and a second configuration to be coupled thereto. The therapeutic device 200' can include a frame 210' and a coupling portion 240' that can be substantially similar in form and/or function to the frame 210 and the coupling portion 240, respectively, described above with reference to FIG. 2. Thus, portions of the therapeutic device 200' are not described in further detail herein. As described above, in some instances, the therapeutic device 200' can be placed adjacent to the face of the user and the coupling portion 240 and more particularly, at least one strap 241' can be manipulated to couple the therapeutic device 200' to the head of the user.

As shown in FIGS. 3 and 4, the therapeutic device 200' can be arranged such that a superotemporal region 216', an inferotemporal region 218', and/or a centrolateral region 217' of a side portion 215' of the frame 210' can bend, flex, elastically deform, etc. when the frame 210' is applied to a user's face. In some embodiments, arrangement of the frame 210' (e.g., at least the side portion 215') can be such that an angle of a convex bend is increased when the frame 210' is applied to a user's face. For example, in some embodiments, the centrolateral region 217' and/or the superotemporal region 216' can be configured to bend and/or deform substantially at or near the midpoint between a first attachment point 226' (coupled to an end portion of the strap 241' (FIG. 4) and a second attachment point 227' (coupled to an end portion of an inferior member 245'(as described above)) such that an anterior surface of the side portion 215' forms an obtuse angle (i.e., greater than 90° but less than 180°) or an acute angle (i.e., less than 90°) between the first attachment point 226' and the second attachment point 227'. Such arrangement can, in some embodiments, reduce a rearward pressure upon a therapeutic member 205' (e.g., substantially similar to the therapeutic member 105) coupled thereto. In turn, a reward pressure applied to the eye region by the therapeutic member 205' is reduced. As such, a pressure that is transmitted to the surface of a user's closed eyelids can be reduced, which in some instances, can result in increased comfort for the user.

In some embodiments, the side portion 215' of the frame 210' can be configured such that the side portion 215' can have an increased flexibility relative to other portions of the frame 210'. Said another way, the arrangement of the side portion 215' can be such that the side portion 215' has a stiffness that is less than a stiffness of the top portion 211' and/or the inferior portion 220'. The stiffness of the side portion 215' can be reduced by, for example, weakening at least the side portion 215', incorporating a different material having a lower flexural modulus into the side portion 215', incorporating a different chemical preparation in the side portion 215', forming one or more discontinuities in the side portion 215', using a different total mass of material in the side portion 215', reducing a cross-sectional area of the side portion 215', and/or the like.

In some embodiments, the side portion 215' of the frame 210' can be reduced in mass by reducing the amount of physical material in the side portion. By way of example, the side portion 215' can be reduced in mass by being thinned. In some embodiments, the side portion 215' of the frame 210' can be thinned generally in a manner that would be described as in a "z-plane," or anteroposteriorly, relative to the position of the frame 210' when the frame 210' is applied to a user's face (see e.g., FIG. 3). In other embodiments, the side portion 210' of the frame can be thinned in a manner that could be described as in an "x-y plane" or a combination of medial-lateral and superior-inferior, relative to the position of the frame 210' when applied to the user's face (see e.g., FIG. 4). In some embodiments, the increased flexibility (e.g., the reduced stiffness as a result of thinning and/or the like) can be such that at least one region of the side portion 215' forms a more acute angle than would otherwise occur without the increased flexibility, when the frame 210 is applied to the user's face in a position of use.

Figure 5:
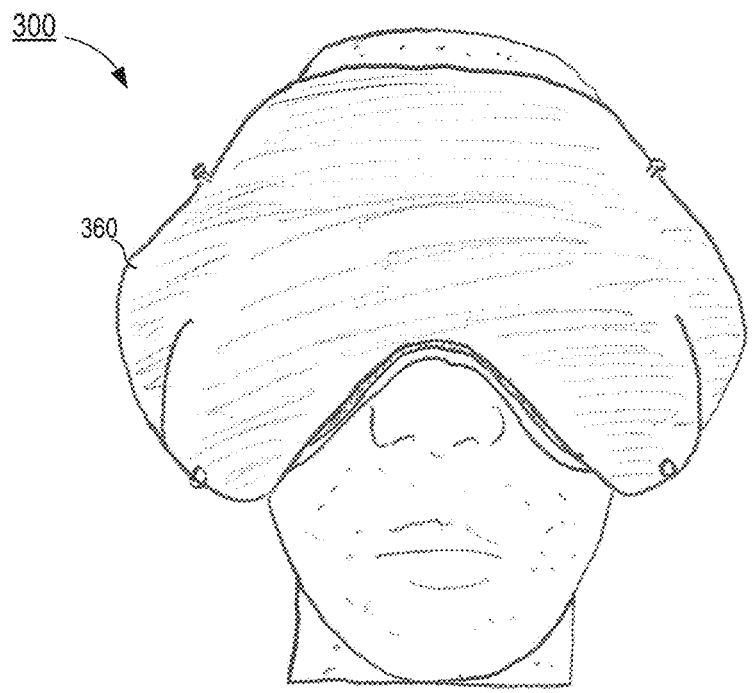
FIGS. 5 and 6 are a front view and a side view, respectively, of a therapeutic device coupled to a portion of the body according to another embodiment.
Figure 6:
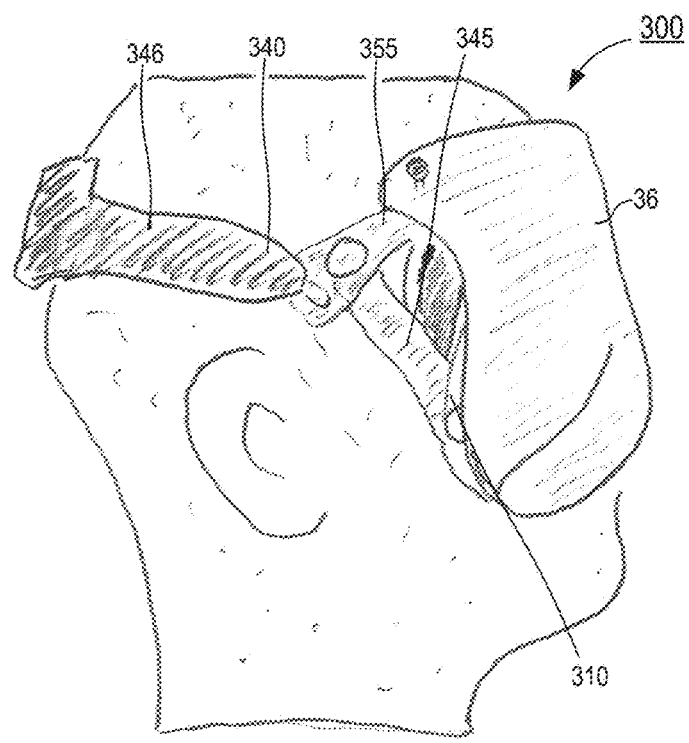

Referring now to FIGS. 5-44, a therapeutic device 300 is illustrated according to another embodiment. As shown in FIGS. 5 and 6, the therapeutic device 300 can be coupled to, for example, the head of a user to place a therapeutic member in contact with a target region of the face such as, for example, the ocular region. The therapeutic device 300 includes a flexible frame 310 (see e.g., FIGS. 7-12), a coupling portion 340 (see e.g., FIGS. 12-22), a first insulating member 360 (see e.g., FIGS. 23-32), and a second insulating member 370 (see e.g., FIGS. 33-37). The therapeutic device 300 (also referred to herein as "eye compress device" or "eye compress system") can be any suitable configuration. For example, in some embodiments, the therapeutic device 300 can be an eye compress or the like such as those described in U.S. patent application Ser. No. 12/153,321 entitled, "Thermal Bodily Compress Kits and Methods of Using Same," filed May 16, 2008; U.S. patent application Ser. No. 12/153,322 entitled, "Thermal Compress Assembly and System with External Frame," filed May 16, 2008; U.S. patent application Ser. No. 12/947,189 entitled, "Thermal Compress System and Methods of Using the Same," filed Nov. 16, 2010; U.S. patent application Ser. No. 13/298,445 entitled, "Thermal Bodily Compress Kits and Methods of Using Same," filed Nov. 17, 2011; U.S. Provisional Patent Application Ser. No. 61/852,263 entitled, "Eye Compress Cover and Method of Use," filed Mar. 15, 2013; and U.S. Patent Application Ser. No. 61/962,067 entitled, "Moistened Disposable Folded Sheets for Use on an Eye Compress, and Methods of Using Same," filed Oct. 30, 2013, the disclosures of which are incorporated herein by reference in their entireties.

Figure 7:
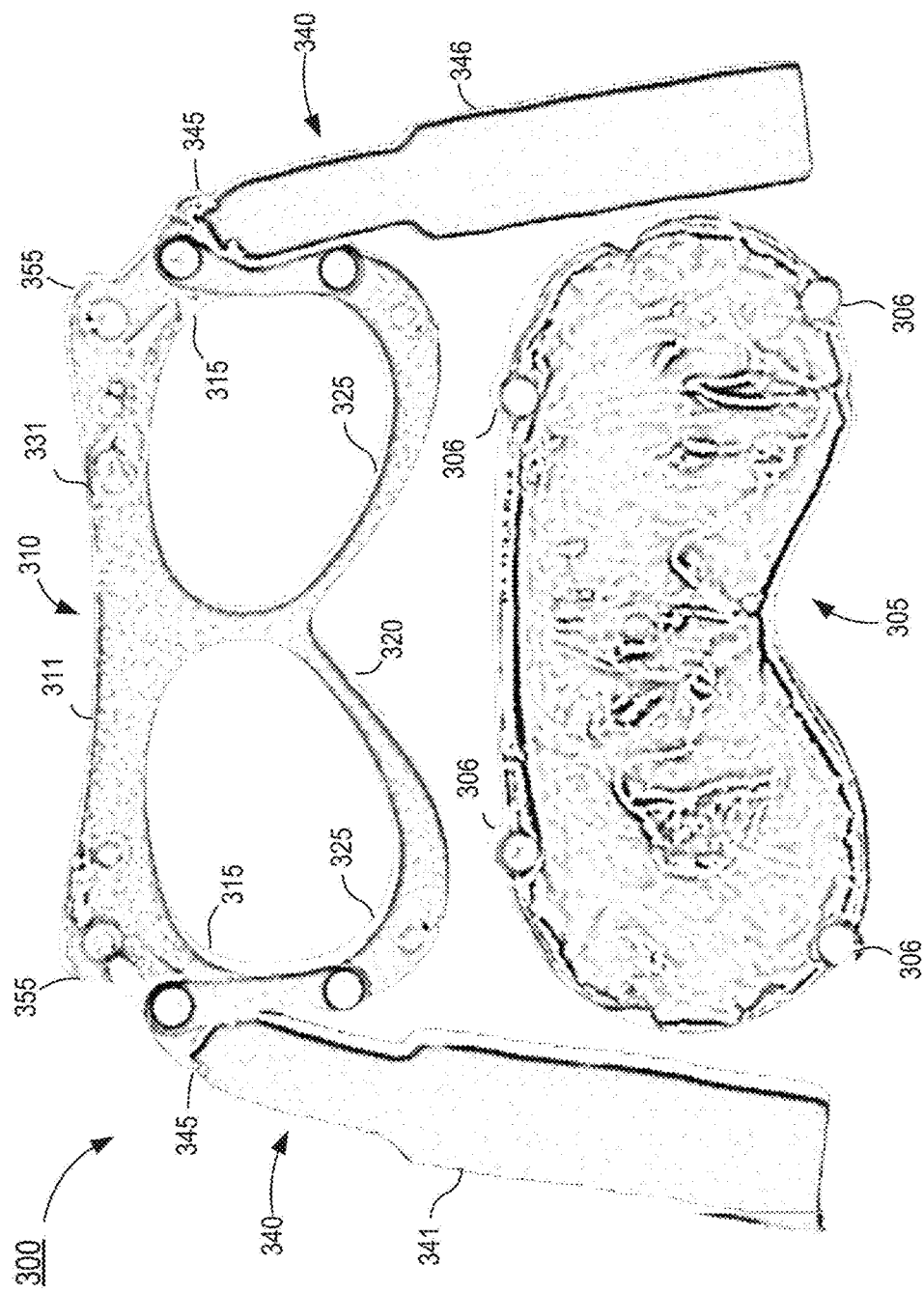
FIG. 7 is a rear view of a portion of the therapeutic device of FIGS. 5 and 6 and a therapeutic member.
Figure 8:
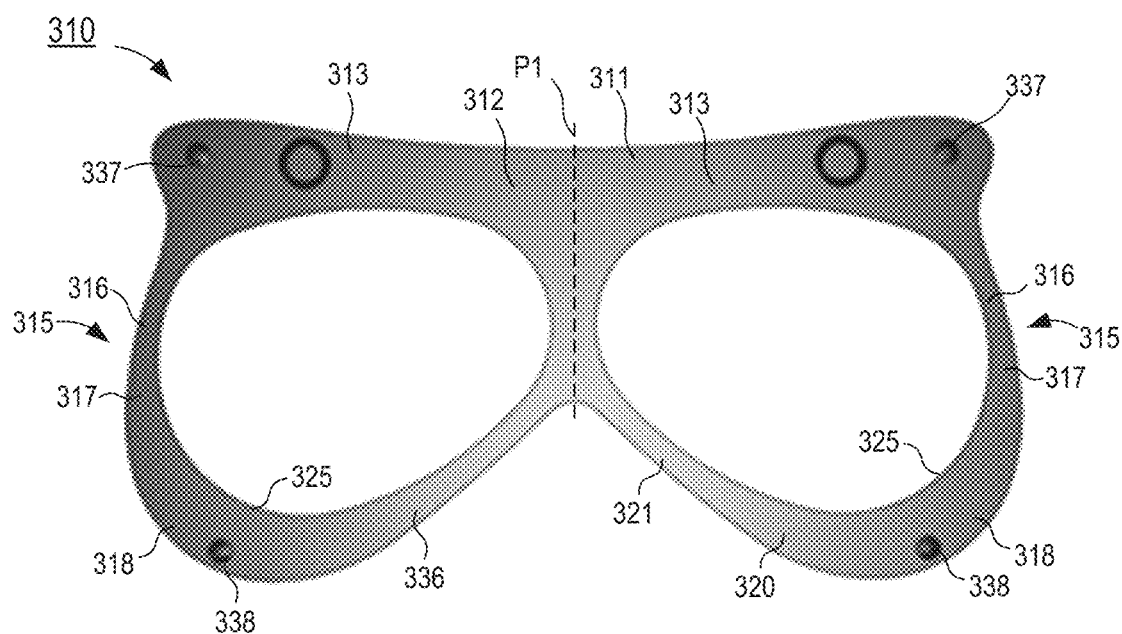
FIGS. 8 and 9 are a front view and a rear view, respectively, of a flexible frame included in the therapeutic device of FIGS. 5 and 6 in a first configuration.

As shown in FIGS. 7 and 8, the flexible frame 310 is configured to support and/or otherwise be coupled to a therapeutic member 305. The therapeutic member 305 can be any suitable configuration. For example, in some embodiments, the therapeutic member 305 can be a thermal gel pack or the like. In such embodiments, the user can place a surface of the thermal gel pack in conductive thermal contact with, for example, the ocular region of the face and in turn, the thermal gel pack can transfer thermal energy to or receive thermal energy from the ocular region. More specifically, the therapeutic member 305 can include a substantially viscous material or combination of materials that can be heated or cooled to provide thermal energy to or receive thermal energy from, respectively, the body.

In some embodiments, the therapeutic member 305 can be disposed in a flexible pouch or the like that can deform when exposed to an external force. Thus, when the therapeutic member 305 is positioned against, for example, the ocular region of the patient, the therapeutic member 305 can elastically deform (e.g., nonpermanently deform), bend, flex, or otherwise reconfigure in such a manner that a surface area in contact with the ocular region is greater than a surface area in contact with an ocular region of a substantially rigid or inflexible therapeutic member that is positioned against the ocular region. In some embodiments, the therapeutic member 305 can define a single inner volume such that when the therapeutic member 305 is placed in conductive thermal contact with the ocular region, a single volume of thermal gel can transfer thermal energy to or receive thermal energy from both the left eye and the right eye of the ocular region. Similarly stated, the therapeutic member 305 can be arranged such that a volume of thermal gel that transfers thermal energy to and/or receives thermal energy from the left eye of the user is in fluid communication with a volume of thermal gel that transfers thermal energy to and/or receives thermal energy from the right eye of the user.

The flexible frame 310 (also referred to herein as "frame") is coupled to the coupling portion 340 (see e.g., FIG. 7) and the first insulating member 360 (see e.g., FIGS. 5 and 6) and supports and/or is at least temporarily coupled to the therapeutic member 305. More specifically, the frame 310 has a posterior surface 331 that includes a set of couplers 332 (see e.g., FIG. 9) that can be matingly coupled to a corresponding set of couplers 306 (see e.g., FIG. 7) included in the therapeutic member 305. The couplers 332 and 306 can be, for example, a set of snaps or the like that can be matingly engaged to removably couple the therapeutic member 305 to the frame 310. Similarly, the frame 310 has an anterior surface 336 that includes a set of protrusions 337 and 338 (see e.g., FIG. 8) that can engage a portion of the first insulating member 360, as described in further detail herein.

Figure 9:
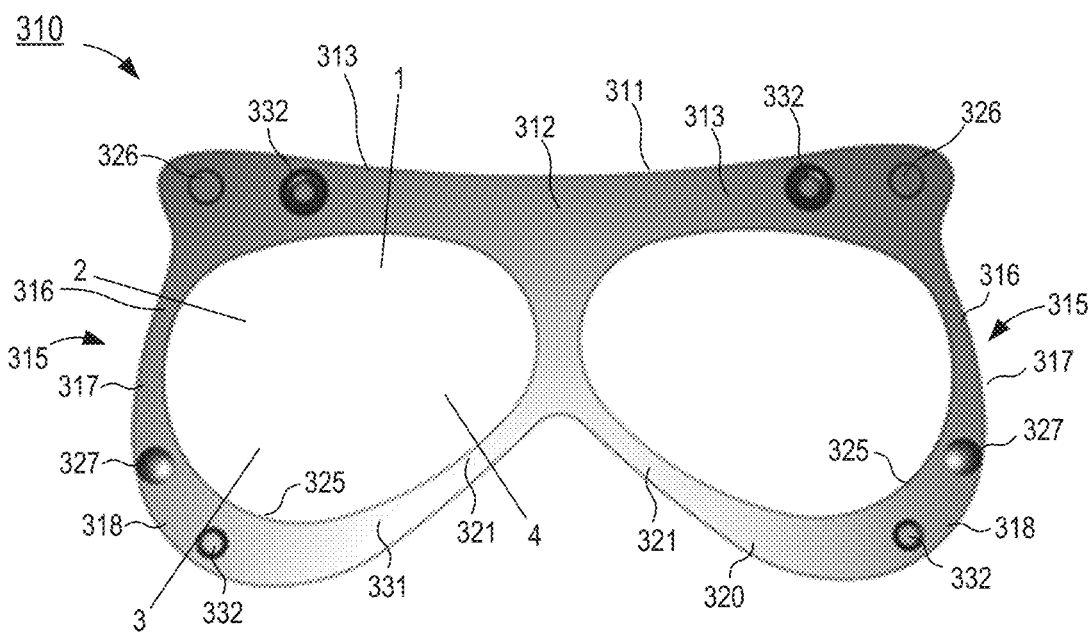

The frame 310 can be any suitable shape, size, or configuration. For example, as is shown in FIGS. 8 and 9, the frame 310 can be arranged to have a substantially smooth contour that can, for example, increase the esthetics of the frame 310. As another example, the frame 310 can have a size and shape that is associated with at least a portion of the ocular region of the user. As such, the frame 310 can include a first lobe and a second lobe that can substantially correspond to a first eye and a second eye of the user. The arrangement of the frame 310 can be such that the first lobe and the second lobe are substantially similar in size and shape while being oriented in opposite directions. Similarly stated, the frame 310 is substantially symmetrical about a plane $P_1$ that passes through a midpoint of the frame 310, as shown in FIG. 8. In this manner, when the therapeutic member 305 is coupled to the frame 310 and the therapeutic member 305 is placed in contact with the ocular region of the user, the frame 310 can support the therapeutic member 305 to maintain a surface of the therapeutic member 305 in contact with the left eye region and the right eye region of the user, as described in further detail herein.

The frame 310 can be monolithically formed from a relatively thin (e.g., between about 0.01" and about 0.15") and flexible material such as those described above with reference to the frame 110 of FIG. 1. As such, the frame 310 can have a stiffness that can allow the frame 310 to bend, flex, elastically deform, and/or otherwise reconfigure between a first, undeformed configuration and a second, deformed configuration when exposed to an external force. More specifically, at least a portion of the frame 310 can have a stiffness that is sufficiently low to allow the frame 310 to transition between a first configuration (e.g., a substantially planar configuration) and a second configuration (e.g., a substantially nonplanar configuration) to place a surface of the therapeutic member 305 in contact with the ocular region of the user. In some embodiments, when the frame 310 is in the second configuration and when the therapeutic device 300 is coupled to a portion of the body, a force exerted by the therapeutic member 305 is distributed along the portion of the body that can reduce discomfort and/or that can increase a surface area of the therapeutic member 305 that is in contact with the portion of the body, as described in further detail herein.

As shown in FIGS. 8 and 9, the frame 310 has a top portion 311 including a top central region 312 and superior regions 313 (relative to the user's eye); a side portion 315 including a superotemporal region 316 disposed at about a midpoint between a first attachment point 326 and a second attachment point 327 on each side portion 315, an inferotemporal region 318, and a centrolateral region 317 disposed at about a midpoint between a top edge of frame 310 and a bottom edge of frame 310; and an inferior portion 320 including an inferomedial region 321. The frame 310 also defines a set of apertures 325. For example, as shown in FIGS. 8 and 9, the frame 310 includes two apertures 325 that correspond to the left eye region and the right eye region. The apertures 325 can, for example, reduce the stiffness of the frame 310 and/or can provide a portion of the frame 310 which reduces rearward pressure upon the eye region when the frame 310 is disposed about the ocular region. In some embodiments, for example, a portion of the therapeutic member 305 can be configured to extend through the apertures 325 such that when the therapeutic member 305 is placed in contact with the ocular region of the user, a force exerted by the therapeutic member 305 directly on the globe of the eye and/or the eye socket is reduced. More specifically, by selectively reducing the stiffness of the frame 310 and allowing a portion of the therapeutic member 305 to extend through the apertures 325, a rearward pressure can be redistributed in such a way as to reduce direct rearward pressure on the eye. Thus, the frame 310 and the therapeutic member 305 can exert a rearward force on the eye that is lower than a force that would otherwise be exerted by, for example, a frame and therapeutic member that did not redistribute the force in such a way as to reduce direct rearward pressure upon the eye (e.g., resulting from a frame with greater stiffness, or the like). In some instances, the reduced rearward force exerted on the eye can increase a user's comfort while being sufficient to substantially maintain the therapeutic member 305 in contact with the eye and/or ocular region. Although portions of the frame 310 are specifically described, certain areas, portions, and/or regions of frame 310 can overlap with other areas, portions, and regions, such that there is no clear delineation between one area, portion, or region, and its contiguously adjoining area, portion, or region. That is to say, while specific portions are described the union, intersection, and/or transition between adjacent portions need not signify a substantially change in a physical property of the frame 310.

The frame 310 can be arranged such that portions of the frame 310 have a different stiffness. For example, the arrangement of the side portion 315 can be such that the side portion 315 has a stiffness that is less than a stiffness of the top portion 311 and/or the inferior portion 320. As another example, the frame 310 can be arranged such that certain regions and/or sub-portions of the frame 310 within the side portion 315 have a stiffness that is less than a stiffness of other regions and/or sub-portions of the frame 310 within the side portion 315. The stiffness of the side portion 315 can be reduced by, for example, weakening at least the side portion 315, incorporating a different material having a lower flexural modulus into the side portion 315, incorporating a different chemical preparation in the side portion 315, forming one or more discontinuities in the side portion 315, using a different total mass of material in the side portion 315, reducing a cross-sectional area of the side portion 315, and/or the like.

By way of example, the superotemporal region 316 of the side portion 315 can have a cross-sectional area that is less than a cross-sectional area of the top portion 311, the inferior portion 320, and/or the inferotemporal region 318, as shown in FIGS. 8 and 9. More specifically, in some embodiments wherein the frame 310 has a substantially uniform thickness, the superotemporal region 316 can have a width defined between a peripheral edge of the frame 310 and an edge defining the aperture 325 that is narrower than a width (similarly defined) of the top portion 310, the inferotemporal region 318, and/or the inferior portion 320. For example, in some embodiments, the superior region 313 of the top portion 310 can have a width (taken at or about the line 1 in FIG. 8) of about 18 millimeters (mm); the superotemporal region 316 can have a width (taken at or about the line 2) of about 6.2 mm; the inferotemporal region 318 can have a width (taken at or about the line 3) of about 19.2 mm; and the inferomedial region 321 can have a width (taken at or about the like 4) of about 7.0 mm. Although specifically described above, the superotemporal region 316 can have any suitable width relative to another region of the frame 310. In some embodiments, the superotemporal region 316 can have a width of about 50% to about 33% of, for example, the inferotemporal region 318. In other embodiments, the superotemporal region 316 can have a width of about 90%, 80%, 70%, 60%, 50%, 40%, 35%, 33%, 25%, 20%, or less of, for example, the inferotemporal region 318.

Figure 10:
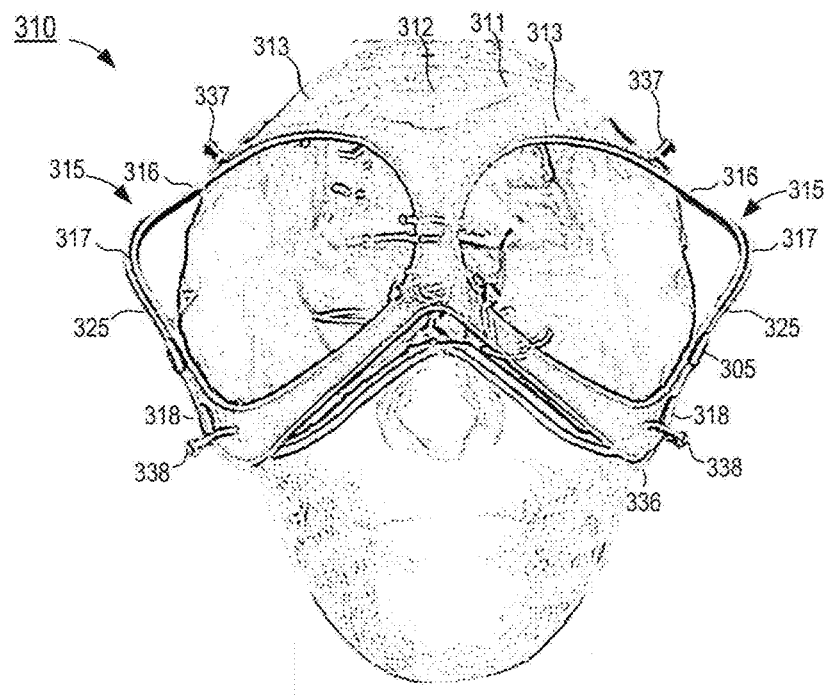
FIGS. 10-12 are a front view, a perspective view, and a side view, respectively, of a portion of the therapeutic device of FIGS. 5 and 6 coupled to the portion of the body and illustrating the flexible frame in a second configuration.
Figure 11:
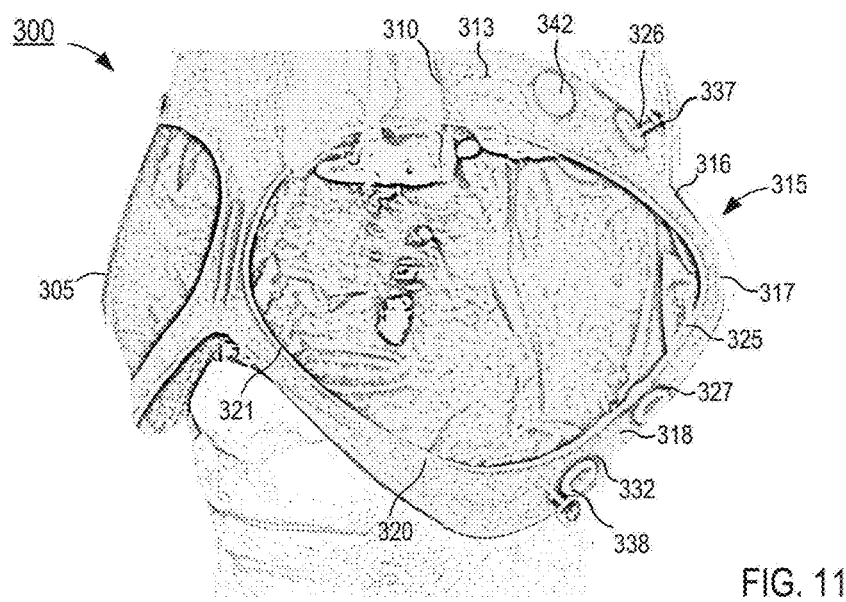
Figure 12:
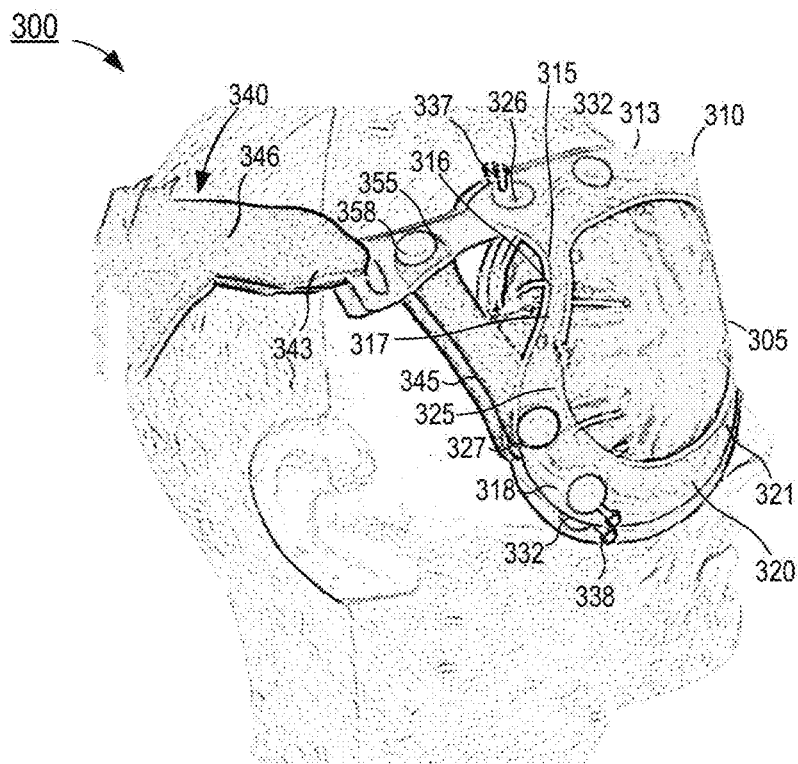

In this manner, at least the superotemporal region 316 of the side portion 315 of the frame 310 can be configured to form a convex bend in a portion of the frame 310 when the frame 310 is applied to a user's face, as shown in FIGS. 10-12. Similarly stated, the reduced stiffness of the side portion 315 can be such that the centrolateral region 317 is pushed in an anterior direction away from the user when the frame 310 is applied to the face of the user. Thus, the side portion 315 can be configured to bend and/or elastically deform between the first attachment point 326 and the second attachment point 327 such that an anterior surface of the side portion 315 forms an obtuse angle (i.e., greater than 90° but less than 180°) or an acute angle (i.e., less than 90°) between the first attachment point 326 and the second attachment point 327. In some embodiments, arrangement of the frame 310 can be such that an angle of a convex bend is increased when the frame 310 is applied to a user's face. Such arrangement can, in some embodiments, reduce a rearward pressure upon a portion of the therapeutic member 305 that, in turn, reduces a rearward pressure applied to the globe of the eye and/or the eye region. As such, a pressure that is transmitted to the surface of a user's closed eyelids can be reduced, which in some instances, can result in increased comfort for the user.

Figure 13:
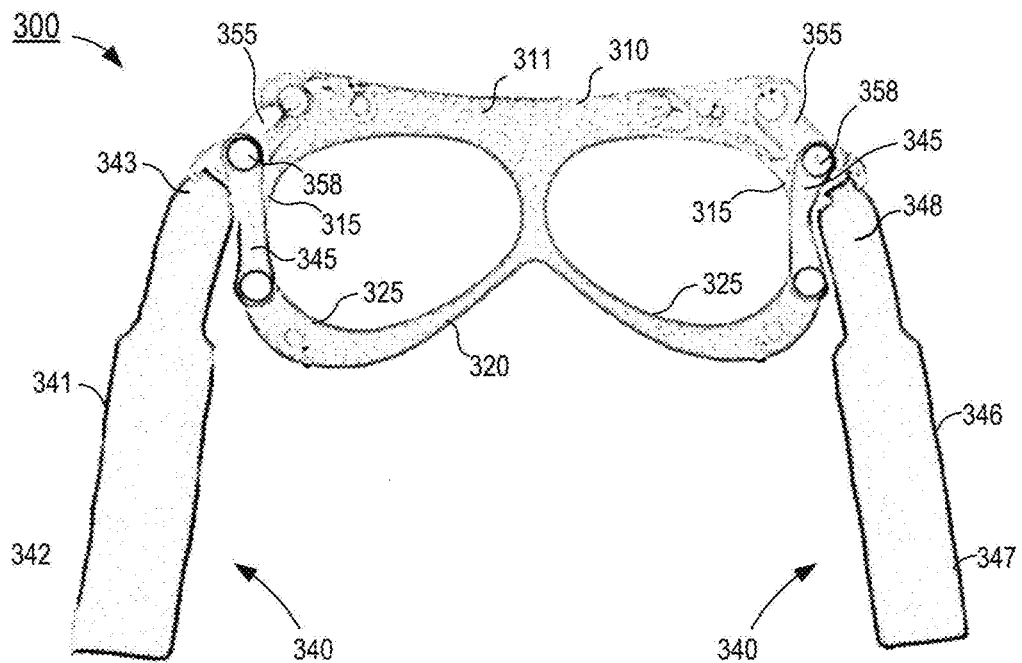
FIG. 13 is a rear view of a portion of the therapeutic device of FIGS. 5 and 6 illustrating a coupling portion.

As shown in FIGS. 12 and 13, the coupling portion 340 of the therapeutic device 300 includes a first strap 341 and a second strap 346 that are each coupled (either directly or indirectly) to a coupling member 355 and an inferior member 345. As described in further detail herein, the coupling members 355 and the inferior members 345 can be coupled to the first attachment point 326 and the second attachment portion 327, respectively, of the frame 310 to couple the first strap 341 and the second strap 346 to the frame 310. Moreover, the coupling portion 340 can be transitioned between a first configuration (see e.g., FIG. 13) and a second configuration (see e.g., FIG. 12) to temporarily couple the therapeutic device 300 to the head of the user. As shown in FIG. 13, the first strap 341 includes a first coupling portion 342 configured to engage the second strap 346 and a second coupling portion 343 configured to couple the first strap 341 to the one of the coupling members 355 and the frame 310. Similarly, the second strap 346 includes a first coupling portion 347 configured to engage the first strap 341 and a second coupling portion 348 configured to couple the second strap 346 to the other coupling member 355 and the frame 310.

As shown in FIG. 14, the first strap 341 can have an overall shape that includes a first portion having a first width $W_1$ and a second portion having a second width $W_2$. For example, in some embodiments, the first width $W_1$ can be about 1" and the second width $W_2$ can be about 1.5". In some embodiments, the width $W_2$ can be based at least in part on the width $W_1$. For example, the width $W_2$ can be 10%, 20%, 30%, 40%, 50%, 60%, 70%, 80%, or 90% greater than the first width $W_1$. In other embodiments, the width $W_2$ can be more than 90% greater than the width $W_1$. The first strap 341 can include a relatively abrupt transition from the first width $W_1$ to the second width $W_2$ that can increase the ergonomics of the first strap 341. In other embodiments, the transition from the first width $W_1$ to the second width $W_2$ can extend over a distance corresponding to a length of the strap 341. For example, in some embodiments, the transition can extend over a distance of about 0.1", 0.15", 0.20", 0.25", 0.30", 0.35", 0.4", 0.5", 0.75", 1.0", 1.25", 1.5", 1.75", 2.0", 2.25", 2.5", or any fraction therebetween.

In some instances, the arrangement of the transition from the first width $W_1$ to the second width $W_2$ can reduce the likelihood of the first strap 341 slipping through the hand of a user while placing the therapeutic device 300 against the face by providing a tactile indication to the user that the first strap 341 could be slipping. Accordingly, the user can grip the first strap 341 more tightly, which can reduce slippage. The transition from the first width $W_1$ to the second width $W_2$ can be positioned along a length of the first strap 341 that can be associated with a width of the user's hand. For example, the transition from the first width $W_1$ to the second width $W_2$ can be positioned such that when a user places the therapeutic device 300 to his or her face, the user's thumb and forefinger are positioned at and/or near the transition. Thus, when the therapeutic device 300 is transitioned to a position in which the weight of the therapeutic device 300 is no longer supported entirely by the palm, the user can grip the first strap 341 at a position along the second width $W_2$ and/or at about the transition between the first width $W_1$ and the second width $W_2$. In one embodiment, the first portion having the first width $W_1$ can have a first length $L_1$ and the second portion having the second width $W_2$ can have a second length $L_2$. In some embodiments, the first length $L_1$ can be about 2.5" and the second length $L_2$ can be about 5". In other embodiments, the first length $L_1$ and the second length $L_2$ can have any suitable dimensions, and the first length $L_1$ can be any fraction of the second length $L_2$. For example, the first length $L_1$ can be about 1.5", 1.75", 2.0", 2.25", 2.75", 3.0", or any other suitable length. As another example, the second length $L_2$ can be about 3", 4", 6", 7", 8", or any other suitable length. Similarly, the first length $L_1$ can be about 30%, 40%, 50%, 60%, 70%, or any other suitable fraction of the second length $L_2$. As such, the first length $L_1$ can, for example, correspond roughly to the width of a human hand. Although not shown in FIG. 14, the second strap 346 can be arranged in a similar manner. For example, the second strap 346 can include a first portion having the first width $W_1$ and the first length $L_1$, and a second portion having the second width $W_2$ and the second length La.

The first coupling portion 342 of the first strap 341 is disposed along the second portion of the first strap 341. The first coupling portion 342 can be any suitable shape, size, or configuration. For example, in some embodiments, the first coupling portion 342 can include a first half of a hook-and-loop coupling mechanism (e.g., Velcro®). By way of example, the first coupling portion 342 of the first strap 341 can include a set of relatively small loops while the first coupling portion 347 of the second strap 346 can include a set of relatively small hooks. In this manner, the coupling portion 340 can be manipulated to place the first coupling portion 342 of the first strap 341 in contact with the first coupling portion 347 of the second strap 346 to transition the coupling portion 340 from its first configuration to its second configuration. When in the second configuration, the first coupling portion 342 of the first strap 341 can at least partially overlap the first coupling portion 347 of the second strap 342 (or vice versa) in such a way as to form the hook-and-loop coupling. In some embodiments, the coupling portion 340 can be arranged such that the first coupling portion 342 or 347 including the relatively soft surface formed by the loop portion of the hook-and-loop coupling is oriented towards the user, while the first coupling portion 347 or 342, respectively, including the relatively rigid surface formed by the hook portion is oriented away from the user.

As described above, the second coupling portion 343 of the first strap 341 can couple the first strap 341 to the frame 310. The second coupling portion 348 of the second strap 346 can be the same in form and function as the second coupling portion 343 of the first strap 341. Thus, a discussion of the second coupling portion 343 of the first strap 341 also applies to the second coupling portion 348 of the second strap 346. As shown in FIGS. 15-22, the second coupling portion 343 can engage the coupling member 355 (see e.g., FIG. 15) and a closure member 351 (see e.g., FIG. 16) to be coupled to the first attachment point 326 of the frame 310. More specifically, the second coupling portion 343 can be transitioned through a set of configurations to be coupled to the coupling member 355, which in turn is coupled to the first attachment point 326 of the frame 310. Furthermore, the closure member 351 includes a base 352 and a set of protrusions 353 (see e.g., FIG. 16) that selectively engage the second coupling portion 343 to maintain the coupling between the first strap 341 and the coupling member 355.

Figure 17:
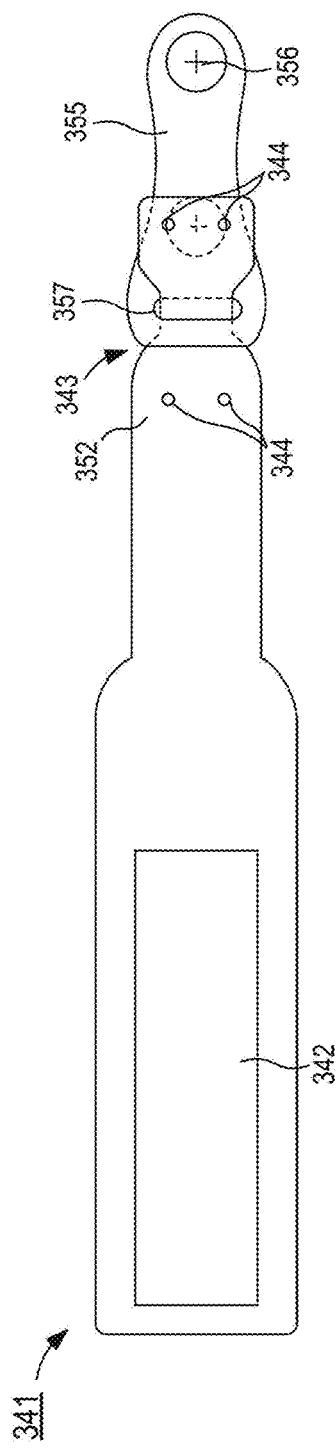
FIG. 17 is a schematic illustration of the strap of FIG. 13 partially coupled to the coupling member of FIG. 15.
Figure 19:
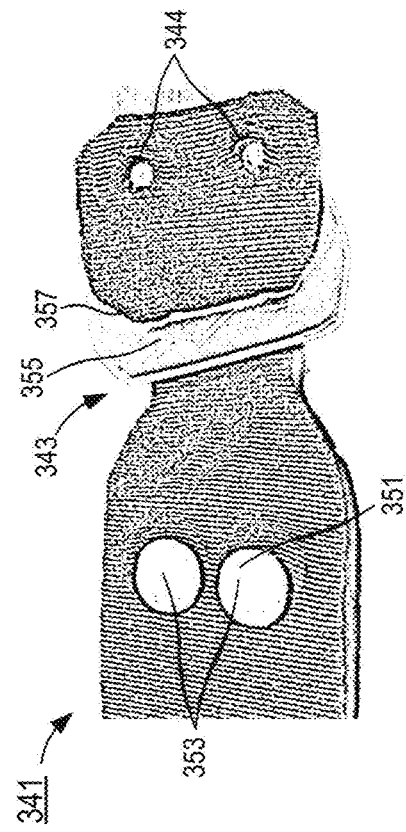
FIGS. 18 and 19 are perspective views of a portion of the strap illustrated in FIG. 13 in a first configuration and a second configuration, respectively.
Figure 18:
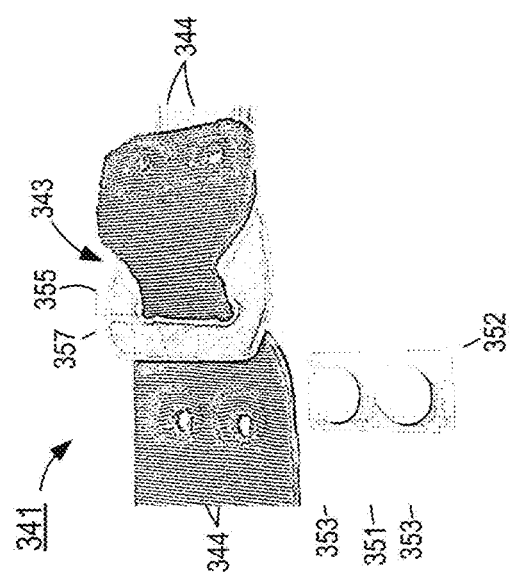

In use, the second coupling portion 343 can be inserted into a slot 357 defined by the coupling member 355 to place the second coupling portion 343 in a first configuration, as indicated by the arrow AA in FIG. 17. As shown in FIGS. 18 and 19, the closure member 351 can be manipulated, for example, to place the base 352 in contact with a first side of the second coupling portion 343, and to insert the protrusions 353 through a corresponding set of openings 344 defined by the second coupling portion 343. More specifically, the second coupling portion 343 includes four openings 344 that can be arranged in a rectangular orientation relative to one another, as shown in FIG. 17. Similarly stated, the set of openings 344 can be arranged in pairs of adjacent openings 344 with the pairs being aligned along a length of the second coupling portion 343 and each adjacent opening 344 in one pair being aligned along a width of the second coupling portion 343. In this manner, the protrusions 353 of the closure member 351 can be disposed in the adjacent openings 344 of one pair, as shown in FIG. 19. The protrusions 353 include a flanged end 354 (see e.g., FIG. 16) that can be pushed through the openings 344 to be disposed on a second side of the second coupling portion 343 opposite the first side, thereby placing the second coupling portion 343 in a second configuration, as shown in FIG. 19. Although the closure member 351 is shown and described above as being unitarily formed (i.e., monolithically formed and/or otherwise forming a single component), in other embodiments, a closure member can be formed of two or more units formed independently (i.e., two separate components).

Once in the second configuration, the second coupling portion 343 can be folded about the coupling member 355 such that the two pairs of openings 344 are aligned coaxially, as indicated by the arrow BB in FIG. 20. Thus, the protrusions 353 of the closure member 351 can be inserted into the corresponding openings 344 such that the flanged end 354 extends beyond a surface of the second coupling portion 343, thereby placing the second coupling portion 343 in a third configuration. In this manner, the first strap 341 can be coupled to the coupling member 355, as shown in FIGS. 21 and 22. Moreover, the coupling member 355 can include a first attachment portion 356 that can be coupled to the first attachment point 326 of the frame 310. For example, in some embodiments, the attachment portion 356 of the coupling member 355 and the first attachment point 326 can form a snap fit or the like that can rotatably couple the coupling member 355, and therefore the first strap 341, to the frame 310. As described above, the second coupling portion 348 of the second strap 346 can be arranged in a similar manner to couple the second strap 346 to the frame 310.

Referring back to FIGS. 12 and 13, the inferior members 345 are coupled to a second attachment portion 358 of the coupling members 355 and are configured to extend at an angle therefrom to allow the inferior members 345 to be coupled to the second attachment points 327 of the frame 310. For example, the inferior members 345 can form a snap fit or the like with the second attachment portion 358 of the coupling members 355 and the second attachment points 327 of the frame 310. Furthermore, the arrangement of the coupling members 355 and the inferior members 345 can form a bifid or V-shape, in which the inferior members 345 extend from the second attachment portion 358 toward the frame 310 at an angle relative to the coupling member 355. Similarly stated, the second attachment points 327 of the frame 310 are disposed in an inferior position relative to the first attachment points 326 and as a result the inferior members 345 traverse a space defined between the coupling member 355 and the second attachment points 327 such that the inferior members 345 are oriented at an angle relative to the coupling members 355.

When the user places the coupling portion 340 in the second configuration to couple the therapeutic device 300 to his or her head, the straps 341 and 346 can exert a force on the coupling members 355 that helps to maintain the therapeutic device 300 in a desired position. The arrangement of the coupling members 355 and the inferior members 345 is such that the force exerted by the straps 341 and 346 is distributed between the coupling members 355 and the inferior members 345 which, in turn, exert a portion of the force on the first attachment point 326 and the second attachment point 327, respectively. Thus, the force exerted by the straps 341 and 346 is distributed along a length of the side portion 315 of the frame 310. Moreover, by thinning at least a portion of the superotemporal region 316 and/or the centrolateral region 317, the distributed force can elastically deform the side portions 315 of the frame 310. In this manner, the force exerted by the frame 310 and the straps 341 and 346 to couple to the therapeutic device 300 to the user can be distributed along the user's head in a manner that can increase a user's comfort and/or can increase a surface area of the therapeutic member 305 in contact with the ocular region of the user.

Expanding further, as described above, the straps 341 and 346 exert a rearward force (for example, toward the rear of the user's head) upon frame 310, which is transmitted through therapeutic member 305 and hence, upon the eye region of the user. The bifid or V-shaped strap arrangement of the coupling portion 340 can divide and/or otherwise distribute the rearward force vector of the straps 341 and 346 into a pair of force vectors exerted on the frame 310, one directed above and one directed below the eye level of the user, thus reducing pressure directly upon the eyes of the user and in some instances, increasing user comfort. In some embodiments, the use of the bifid or V-shaped arrangement of the coupling portion 340, and in particular an arrangement in which the coupling members 355 are formed from a relatively inelastic material and the inferior members 345 are formed from a relatively elastic material, can result in an outward or convex bending of the side portions 315 of the flexible frame 310. Thus, for example, the force exerted by the straps 341 and 346 upon the frame 310 can displace a region associated with attachment point 326 in an posterior-inferotemporal direction, and can displace the inferotemporal region 318 associated with attachment point 327 in a posterior-superotemporal direction. Moreover, the arrangement of the frame 310 can be such that the side portions 315 elastically deform (i.e., nonpermanently deform or otherwise reconfigure) in a convex and generally anterotemporal direction in response to the forces exerted on the frame 310 by the coupling portion 340.

In some embodiments, the outward or convex bending of the side portions 315, especially when such a convex bending is positioned at and/or near the eye level of the user, can, for example, result in a reduced rearward pressure upon therapeutic member 305. Thus, a rearward pressure exerted upon the user's eyes is less than a rearward pressure that would otherwise be exerted by a frame having side portions of greater stiffness (e.g., side portions that were not configured to outwardly or convexly bend, as described above). Said another way, forces exerted by the coupling portion 340 and/or the frame 310 that would otherwise be directed rearward toward the eye regions and that could, for example, result in an increase in pressure upon the eyes, and/or an increase in ocular discomfort, are converted and/or distributed by the anterotemporal bending of the frame 310, into forces that are directed anterotemporally away from the eye region, which can, for example, result in a decreased pressure upon the eyes, and/or can, for example, result in greater user ocular comfort. In addition, the convex bending of the frame 310 shortens a vertical distance between the upper couplers 332 and the lower couplers 332 of the frame 310, thereby reducing a tension within a portion of the therapeutic member 305 that can otherwise result from a stretching of therapeutic member 305 between the upper couplers 332 and the lower couplers 332 of the frame 310. Thus, as the tension is decreased, the therapeutic member 305 can assume a less rigid configuration, which in turn, can reduce the pressure placed upon the eyes, and/or can reduce the ocular discomfort of the user.

Although the frame 310 and/or coupling portion 340 are specifically described above, in other embodiments, the frame 310 and/or the coupling portion 340 can be arranged in any suitable manner that can, for example, increase the convex bending of a portion of the frame 310 to decrease a direct pressure exerted on the eyes, and/or can reduce user discomfort. For example, by weakening or thinning at least a portion of the superotemporal region 316 and/or the centrolateral region 317, a distributed force can result in an amount of elastic deformation of the side portions 315 of the frame 310 that is greater than an amount of elastic deformation of a side portion not weakened or thinned. In some instances, a reduction in pressure exerted on the eye region, and/or a reduction in user discomfort (i.e., an increase in user comfort) can, for example, allow a user to more easily apply therapeutic device 300 in a close-fitting and therapeutic manner, which in turn, can improve therapeutic outcomes. As described above, the apertures 325 defined by the frame 310 allow a portion of the therapeutic member 305 to extend anteriorly, away from the eyes and substantially without resistance, when the therapeutic device 300 is coupled to the head of the user. Thus, the arrangement of the apertures 325 can further reduce a force exerted by the therapeutic member 305 directly toward the globe of the eye. As such, the apertures 325 and hence, the reduction of posteriorly-directed forces within the region of the apertures 325, can further reduce the pressure upon the globe of the eye, and/or can increase the comfort of the user.

While the arrangement of the side portions 315 and the apertures 325 of the frame 310 reduce a rearward pressure exerted on the eyes of the user, the relatively larger surface area of the frame 310 substantially at and/or near the inferotemporal region 318 can, for example, exert a force upon a larger surface area, and in some embodiments upon a larger volume, of therapeutic member 305. In some embodiments, the larger surface area of the inferotemporal region 318 can be such that when the straps 341 and 346 exert a force on the frame 310 (as described above), at least a portion of the inferotemporal region 318 is displaced in a superoposterior direction, which in turn can displace a greater volume of contents of the therapeutic member 305 substantially in the same direction. More specifically, in some instances, such contents of the therapeutic member 305 can be displaced in the superoposterior direction up from a cheek region and toward the eye of the user. Similarly, the relatively large surface area of the superior region 313 of the frame 310 can displace a volume of content of the therapeutic member 305 in an inferoposterior direction. Thus, the force exerted by the inferotemporal region 318, and also in some embodiments by superior region 313, can be such that a volume of the contents (e.g., thermal gel) included in the therapeutic member 305 is pushed and/or directed toward the ocular region of the user. Moreover, by allowing the side portion 315 to bend in an anterolateral or convex direction (as described above), the inferotemporal region 318, and also in some embodiments by superior region 313, can direct a volume of the contents of the therapeutic member 305 in such a way that the total effect of force exerted by frame 310 upon the therapeutic member 305 is smaller than would otherwise be possible without the selective bending or flexing of the side portion 315. Moreover, with a portion of the therapeutic member 305 extending through the apertures 325 (as described above), a force exerted by the therapeutic member 305 directly toward the globe of the eye is reduced, which in some embodiments can thereby further increase comfort of the user.

Referring now to FIGS. 23-32, the first insulating member 320 can be transitioned from a first configuration (FIGS. 23, 24, 27 and 28) to a second configuration (FIGS. 29-32) to be coupled to an anterior surface of the frame 310. The first insulating member 360 (also referred to herein as "insulating portion") can be any suitable shape, size, or configuration and can be formed from any suitable insulating material or combination thereof. For example, the first insulating member 360 can have a shape that is associated with the frame 310 and can be formed from a relatively thin neoprene-foam fabric material. In some embodiments, the first insulating member 360 can be a cover or the like such as those described in U.S. Provisional Patent Application Ser. No. 61/852,263 entitled, "Eye Compress Covers and Methods of Use," filed Mar. 15, 2013, the disclosure of which is incorporated herein by reference in its entirety. In some embodiments, the first insulating member 360 can include a neoprene-foam core that is surrounded by a fabric such as, for example, spandex (e.g., Lycra®), or the like. In other embodiments, the first insulating member 360 can be formed from, for example, polyester, polyethylene terephthalate, polyester-olefin, polyester microfibers, and/or the like. In other embodiments, the first insulating member 360 can be formed from fabrics derived from natural materials including felts, wools, heavy-gauge cotton, nylon fabrics, foams, plastics, woven and nonwoven materials, and/or the like.

Figure 23:
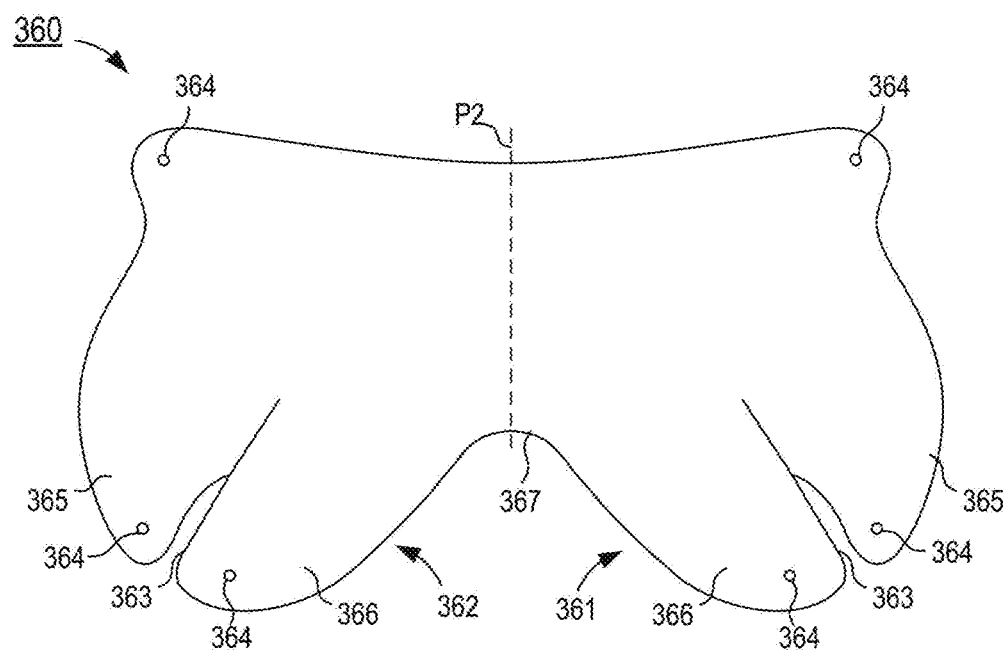
FIGS. 23 and 24 are front views of a first insulating member included in the therapeutic device of FIGS. 5 and 6.
Figure 24:
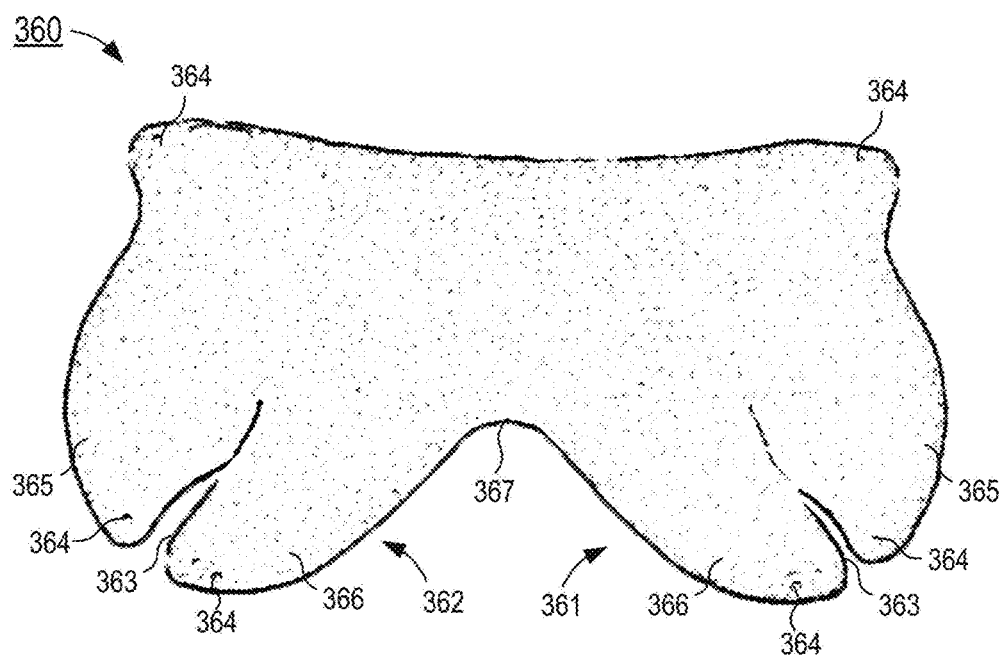

As shown in FIGS. 23 and 24, the first insulating member 360 is substantially flat (e.g., substantially planar or including an anterior surface and a posterior surface that are substantially parallel and two dimensional) when in its first configuration. The first insulating member 360 has a first lobe 361 and a second lobe 362 at least partially defined and/or separated by a nasal region 367, and defines a set of openings 364. The arrangement of the first insulating member 360 can be such that the first lobe 361 and the second lobe 362 are substantially similar in size and shape while being oriented in opposite directions. Similarly stated, the first insulating member 360 is substantially symmetrical about a plane $P_2$ that passes through a midpoint of the nasal region 367, as shown in FIG. 23. Thus, a discussion of the first lobe 361 of the first insulating member 360 also applies to the second lobe 362 of the first insulating member 360.

The first lobe 361 defines a slit 363 that separates a portion of the first lobe 361 into a first leaflet 365 disposed on a first side of the slit 363 and a second leaflet 366 defined on a second side of the slit 363. The first lobe 361 can be arranged such that a width of the slit 363 varies along its length. As an example, the width of the slit 363 can increase along length. More particularly, the slit 363 can have a first width at an origin (e.g., a first end portion in a position that generally corresponds to the center of the eye region) and a second width at a peripheral position (e.g., a second end portion in a position that generally corresponds to a peripheral edge of the first insulating member 360). In some embodiments, the arrangement of the slit 363 can be such that as the slit 363 transitions from the first width to the second width, a wedge-shaped space is defined between the first leaflet 365 and the second leaflet 366, as shown in FIGS. 23 and 24. In some embodiments, the first leaflet 365 can include a substantially curvilinear edge surface and the second leaflet 366 can include a substantially linear edge surface, which collectively define the slit 363. In some embodiments, the slit and/or an edge surface of the leaflets 365 and 366 can be configured to selectively position the leaflets 365 and 366 relative to one another when the first insulating member 360 is in the second configuration, as described further below. In some embodiments, a peripheral or distal portion of the first leaflet 365 and the second leaflet 366 that collectively define a portion of the slit 363 can be substantially rounded.

Figure 25:
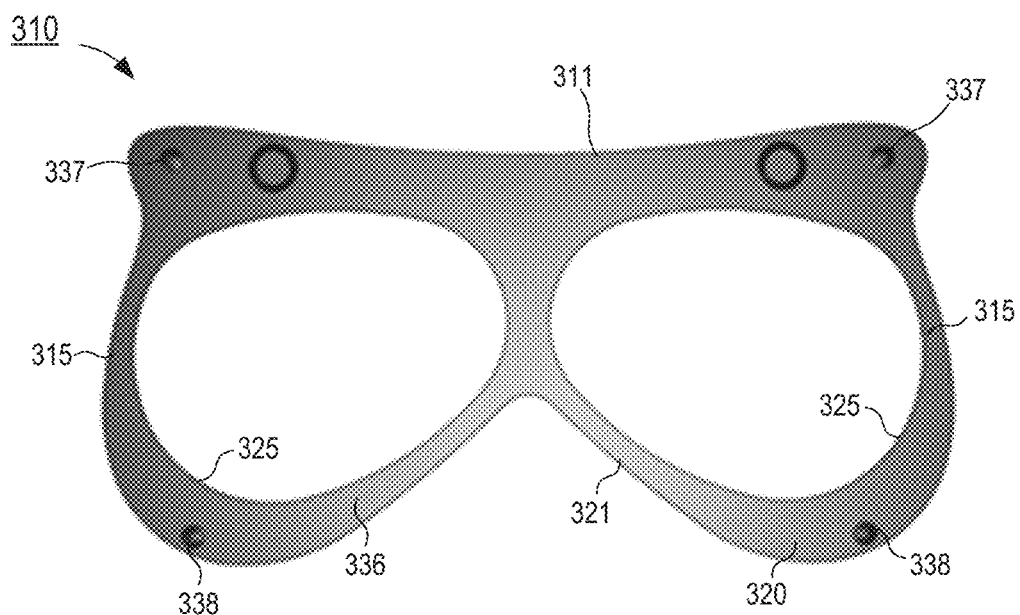
FIG. 25 is a front view of the flexible frame of FIGS. 11 and 12.
Figure 26:
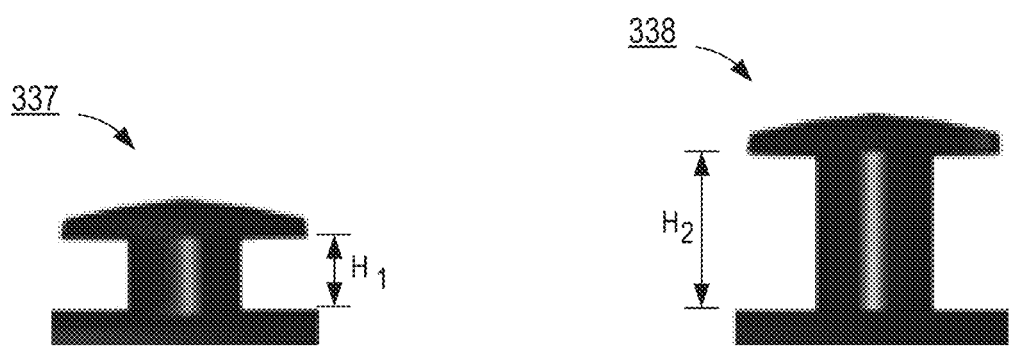
FIG. 26 is a side view of a first coupling member and a second coupling member included in the flexible frame of FIG. 25.

The arrangement of the slit 363 can allow the second leaflet 366 to be moved relative to the first leaflet 365 (or vice versa) to couple the first lobe 361 to the frame 310. Furthermore, portions of the second lobe 362 can be moved in a similar manner to couple the second lobe to the frame 310. For example, as shown in FIGS. 25 and 26, the anterior surface 336 of the frame 310 includes a first set of posts 337 and a second set of posts 338. The first set of posts 337 are disposed along the top portion 311 of the frame 310 and the second set of posts 338 are disposed along the inferior portion 320 of the frame 310. As such, the first set of posts 337 and the second set of posts 338 can be inserted into the set of openings 364 defined by the first insulating member 360 to couple the first insulating member 360 thereto. As shown in FIG. 26, the first set of posts 337 and the second set of posts 338 can each include a flanged end portion that can be placed in contact with an anterior surface of the first insulating member 360, when disposed in the openings 364, to at least temporarily maintain the position of the first insulating member 360 relative to the frame 310. Furthermore, the first set of posts 337 can have a first height $H_1$ defined between a base and the flanged end that can substantially correspond with a width of the first insulating member 360. Similarly, the second set of posts 338 can have a second height H2 defined between a base and the flanged end that can about twice the width of the first insulating member 360, as described in further detail herein.

Figure 27:
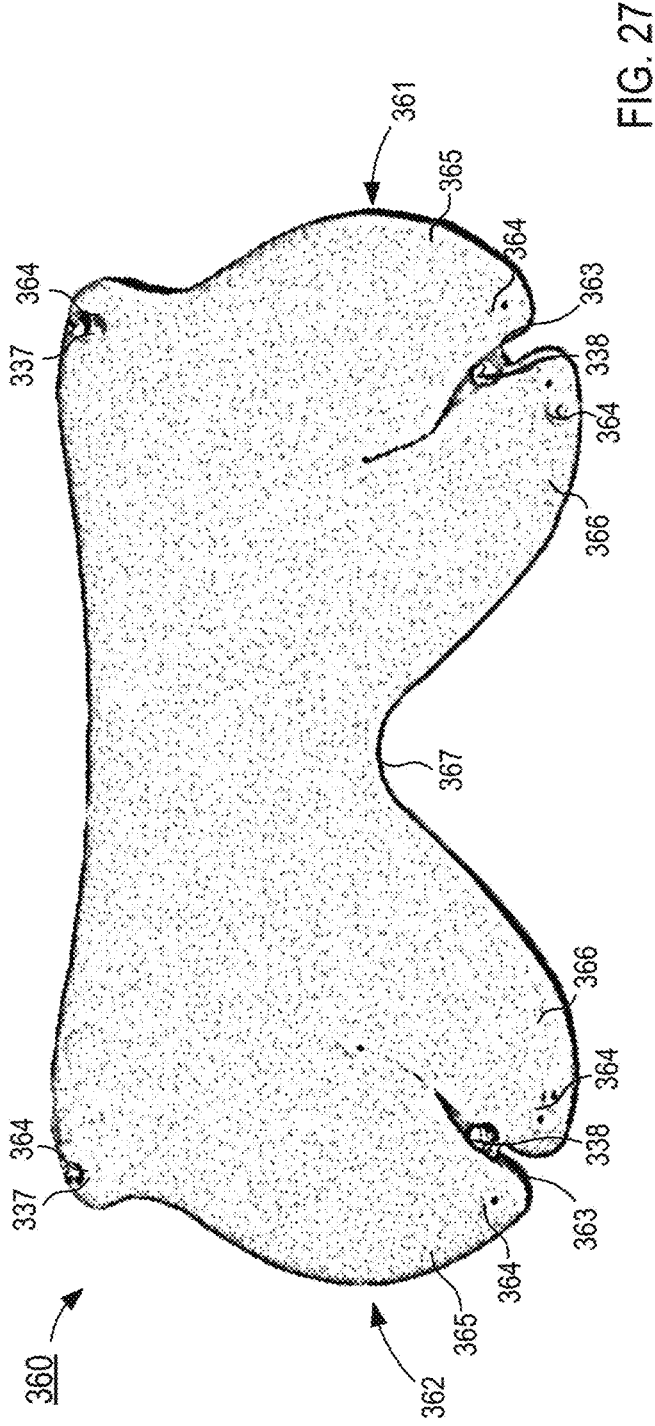
FIGS. 27 and 28 are a front view and a bottom view, respectively, of the first insulating member of FIGS. 23 and 24 in a first configuration and partially coupled to the flexible frame of FIG. 8.
Figure 28:
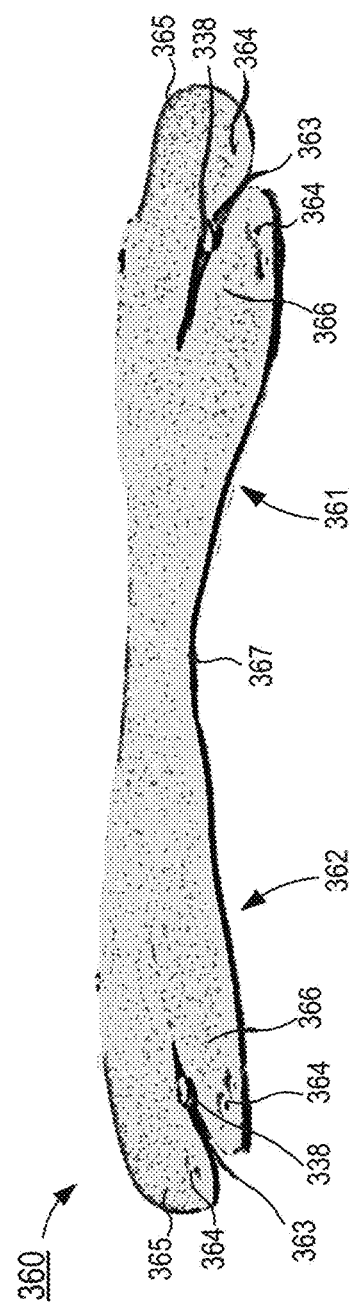
Figure 31:
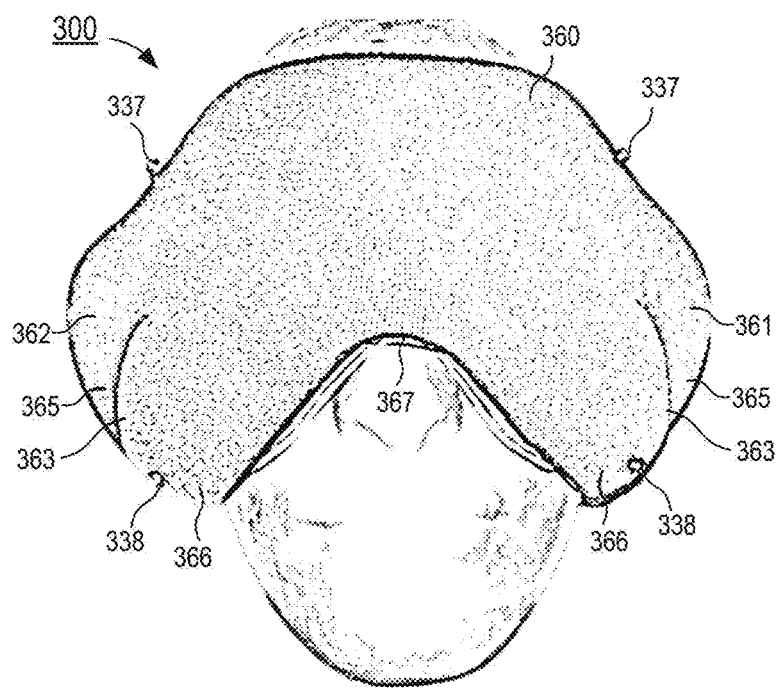
FIGS. 31 and 32 are a front view and a side view, respectively, of the therapeutic device of FIGS. 5 and 6 coupled to the portion of the body.
Figure 32:
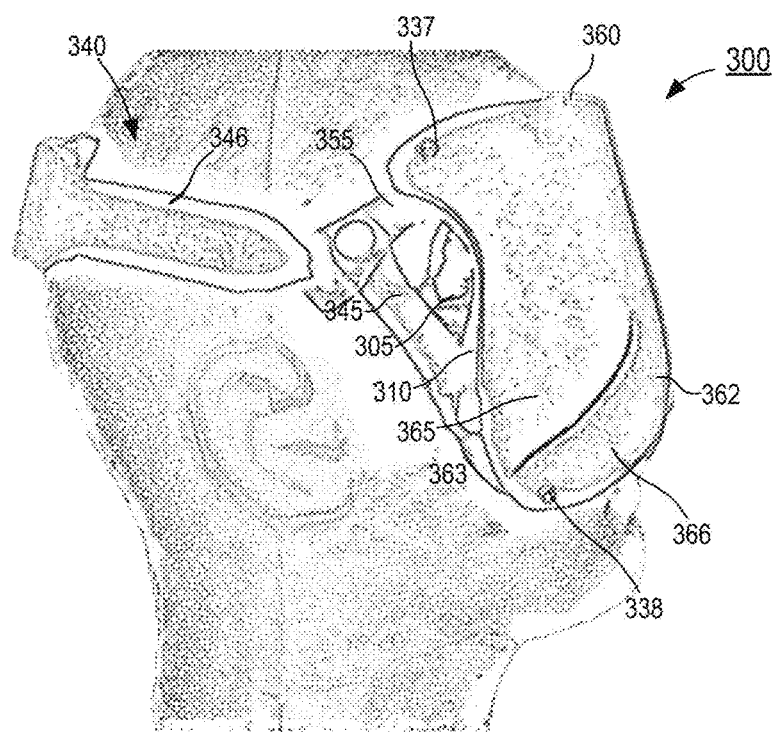

As described above, the first insulating member 360 can be transitioned from a first configuration to a second configuration to be coupled to the frame 310. For example, FIGS. 27 and 28 illustrate the first insulating member 360 in the first configuration and partially coupled to the frame 310 (e.g., the first set of posts 337 are disposed in the openings 364 along a top of the first insulating member 360). As shown in FIGS. 29 and 30, the user can manipulate the first lobe 361 and the second lobe 362 to place the first insulating member 360 in the second configuration, thereby coupling the first insulating member 360 to the frame 310. For example, the user can manipulate the first lobe 361 and the second lobe 362 to insert the second set of posts 338 in the openings 364 defined by the first leaflets 365 and then can move the second leaflets 366 relative to the first leaflets 365 to insert the second set of posts 338 in the openings 364 defined by the second leaflets 366. As a result, a portion of the second leaflets 366 overlaps a portion of the first leaflets 365 so that the leaflets 365 and 366 substantially fully cover the front portion of therapeutic member 305 substantially without any gaps being present between leaflets 365 and 366. Moreover, the arrangement of the slit 363 can increase the flexibility of the lobes 361 and 362 as well as minimize material that would otherwise bunch, obstruct, and/or prevent the first leaflets 365 and/or the second leaflets 366 from fully overlapping one another and thereby fully covering the front portion of therapeutic member 305. Furthermore, the height $H_1$ of the first set of posts 337 and the height H2 of the second set of posts 338 can be such that the flanged ends are in contact with the anterior surface of the first insulating member 360 to at least temporarily retain the position of the first insulating member 360 relative to the frame 310.

As shown in FIGS. 29-32, by moving the first leaflets 365 and the second leaflets 366 relative to one another, the first lobe 361 and the second lobe 362 are deformed. Similarly stated, when the first insulating member 360 is in its second configuration, the first lobe 361 and the second lobe 362 are transitioned from having an anterior surface that is substantially flat or two-dimensional to having the anterior surface that is not flat or three-dimensional. For example, the first lobe 361 and the second lobe 362 can form a convex and/or conical shape that extends in the anterior direction. More specifically, moving the second leaflets 366 such that the portion of the second leaflets 366 overlaps the portion of the first leaflets 365 results in a tenting of the first lobe 361 and the second lobe 362. In this manner, the first insulating member 360 can be placed in its second configuration to form two convex portions that substantially correspond to the first lobe and the second lobe (described above) of the frame 310. In some embodiments, the relative position of the openings 364 defined by the first leaflets 365 and the second leaflets 366 can modify one or more characteristics of the convex portion. For example, in some embodiments, the openings 364 can be disposed at a predetermined distance from a surface (i.e., a periphery surface or the like) of the first leaflets 365 and the second leaflets 366 that defines the slit 363. By way of example, in some embodiments, the openings 364 can be about 5 millimeters (mm) from the surface, about 10 mm from the surface, about 14 mm from the surface, about 20 mm from the surface, about 30 mm from the surface, about 50 mm from the surface about 75 mm from the surface, about 100 mm from the surface, or any distance or fraction of distance therebetween. Moreover, the relative positioning of the opening 364 defined by the first leaflets 365 can be different from a relative positioning of the opening 364 defined by the second leaflets 366. For example, the opening 364 defined by the first leaflets 365 (e.g., lateral leaflets) can be less than 10 mm from the surface, while the opening 364 defined by the second leaflets 366 (e.g., medial leaflets) can be greater than 10 mm from the surface.

In some embodiments, the convex portions of the first insulating member 360 can substantially correspond to the portions of the therapeutic member 305 that extend through the apertures defined by the frame 310, as described above. For example, the convex shape of the first lobe 361 and the second lobe 362 can define a posterior volume (not shown) that can receive the portions of the therapeutic member 305. As a result, the first insulating member 360 surrounds at least the portion of the anterior surface of the therapeutic member 305 to reduce thermal energy that would otherwise be transferred from or to the anterior surface of the therapeutic member 305 (e.g., due to convection heat transfer or the like). Moreover, the convex shape of the first lobe 361 and the second lobe 362 reduces a force that would otherwise be exerted by a substantially flat or non-convex first insulating member on the anterior surface of the therapeutic member 305, which reduction in force can increase a user's comfort level. In addition, the first insulating member 360 can include and/or be formed from a material (e.g., neoprene, neoprene foam, other foam materials, and/or the like) that can have a stiffness that is sufficient to remain in the second configuration without external support of the convex portion of the first lobe 361 and the second lobe 362.

Figure 33:
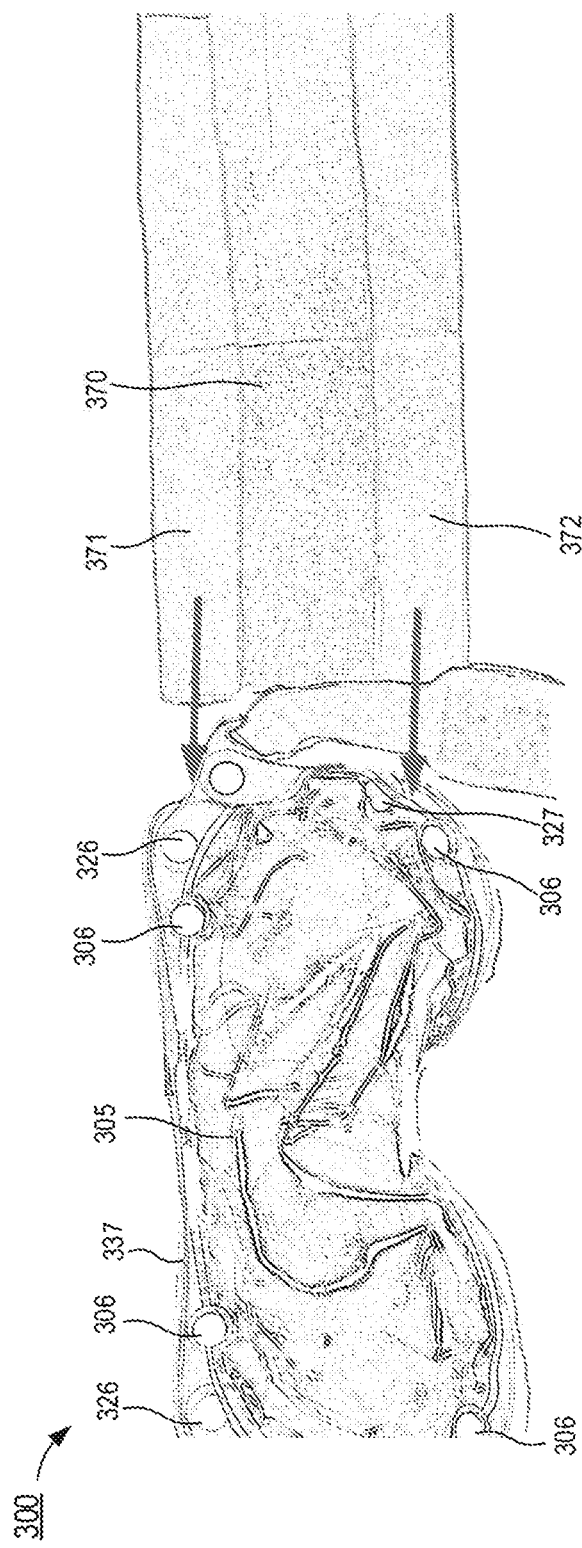
FIG. 33 is a rear view of the therapeutic device of FIGS. 5 and 6 and a second insulating member according to an embodiment.
Figure 34:
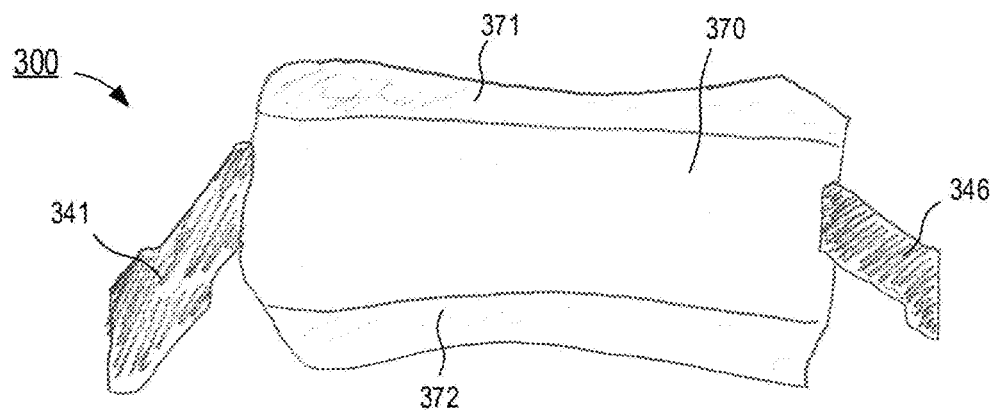
FIG. 34 is a rear view of the second insulating member of FIG. 33 coupled to the therapeutic device of FIGS. 5 and 6.
Figure 35:
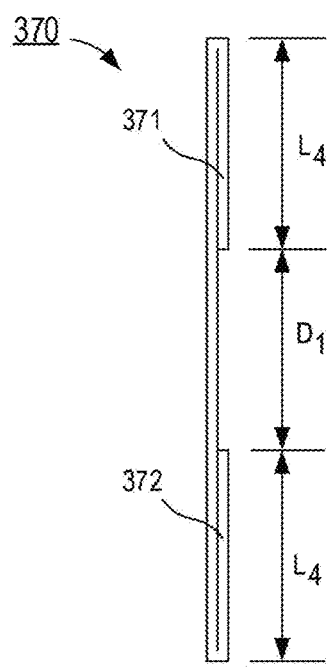
FIG. 35 is a side view of the second insulating member of FIG. 33.

While the first insulating member 360 is described as being disposed in an anterior position relative to the frame 310, the second insulating member 370 can be disposed in a posterior position relative to the therapeutic member 305. For example, as shown in FIGS. 33-35, the second insulating member 370 (also referred to herein as "sheet") can be a relatively thin sheet or fabric that can be coupled to a posterior surface of the frame 310 and/or a posterior surface of the therapeutic member 305. In some embodiments, the second insulating member 370 can be formed from a fibrous nonwoven fabric or the like that can be disposable. In some embodiments, the second insulating member 370 can be substantially similar to the folded sheets described in co-pending U.S. Provisional Patent Application Ser. No. 61/962,067, entitled, "Moistened Nonwoven Disposable Folded Sheets for Use on an Eye Compress, and Methods of Using Same," filed Oct. 30, 2013, the disclosure of which is incorporated by reference above.

In some embodiments, the second insulating member 370 can include a portion that includes, for example, an adhesive or the like that can couple the second insulating member 370 to the frame 310 and/or the therapeutic member 305. In other embodiments, the second insulating member 370 can be disposed adjacent to the therapeutic member 305 and at least temporarily retained in a fixed position during use of the therapeutic device 300. For example, in use the second insulating member 370 can be disposed between the therapeutic member 305 and the face of the user and can be maintained in a relatively fixed position by a force exerted by the therapeutic device 300 that is operable in coupling the therapeutic device 300 to the user. As another example, the second insulating member 370 can be disposed upon a surface of the therapeutic member 305, and can, for example, be held in place by gravity, moisture, electrostatic force, surface tension, friction, and/or the like.

The second insulating member 370 can have a shape and size that is associated with the therapeutic member 305 and/or the frame 310. For example, the second insulating portion 370 can have a length and a width that are sufficient to cover at least a portion of the therapeutic member 305 and/or the frame 310 when coupled thereto. For example, the second insulating member 305 can have a length of between about 6" and 12", between about 7" and 11", between about 8" and 10", between about 8.5" and 9.5" or about 9", and a width between about 3" and 6", between about 3.5" and 4.5", between about 3.75" and 4.25", or about 4".

The second insulating member 370 can include a first folded region 371 and a second folded region 372. The first folded region 371 and the second folded region 372 can be, for example, folded in a similar direction such that when the second insulating member 370 is coupled to the therapeutic member 305 and/or the frame 310, the folded regions 371 and 372 are placed in contact with a surface of the therapeutic member 305 and/or the frame 310. Similarly, second insulating member 370 can be placed upon the surface of the therapeutic member 305 such that the folded regions 371 and 372 face away from the surface, as shown in FIG. 33. The folded regions 371 and 372 can be configured to increase a thickness of the second insulating member 370 in selected areas. For example, when coupled to the therapeutic member 305 and/or the frame 310, the first folded region 371 can cover the first attachment points 326 of the frame 310 and a superior set of the couplers 306 of the therapeutic member 305. Similarly, the second folded region 372 can cover the second attachment points 327 of the frame 310 and an inferior set of couplers 306 of the therapeutic member 305. For example, as shown in FIG. 35, the first folded region 371 and the second folded region 372 can each have a length $L_4$ and can define a distance $D_1$ therebetween. In some embodiments, the distance $D_1$ and the length $L_4$ can be substantially the same. In other embodiments, the distance $D_1$ and the length $L_4$ can be different (e.g., the distance $D_1$ is greater than the length $L_4$). In other embodiments, the first folded region 371 can have a length that is different from a length of the second folded region 372.

By way of example, in some embodiments, the length $L_4$ of the first folded region 371 and the second folded region 372 can be between about 2.5" and 0.5", between about 1.75" and 0.75", between about 1.5" and 1.0", or about 1.25". The distance $D_1$ defined between the first folded region 371 and the second folded region 372 can be between about 0.5" and 2.5", between about 0.75" and 2.25", between about 1.0" and 2", between about 1.25" and 1.75", or about 1.5". In other embodiments, the second insulating member 370 can be arranged such that the distance $D_1$ is a percentage of the width of the second insulating member 370. By "width of the second insulating member" it is understood that the width can be measured when the second insulating member 370 is either in a folded configuration (wherein the width is equal to, for example, $2*L_4+D_1$), or in an unfolded configuration (wherein the width is equal to, for example, $4*L_4+D_1$). For example, in some embodiments, the distance $D_1$ can be about 5%, 6%, 7%. 8%, 9%, 10%, 15%, 20%, 30%, 40%, 50%, 60%, or any suitable percentage or fraction of a percent therebetween of the width of the second insulating member 370. In other embodiments, the second insulating member 370 can be arranged such that distance $D_1$ is a percentage of the width of the length $L_4$. For example, the distance $D_1$ can be about 10%, 15%, 20%, 25%, 50%, 75%, 100%, 120%, 150%, 200%, or any suitable percentage of fraction of a percent therebetween of the length $L_4$. While in some embodiments, folds in a second insulating member can be prearranged in a package, for example, by a manufacturer, in other embodiments, a second insulating member need not be packaged in a folded configuration. In such embodiments, for example, a user can re-form or fold the second insulating member before or after application of the second insulating member to therapeutic member 305. In some embodiments, the second insulating member can include, for example, a visual indication (e.g., a line, marking, shading, etc.) that can be associated with an axis about which the user can fold the second insulating member.

Figure 36:
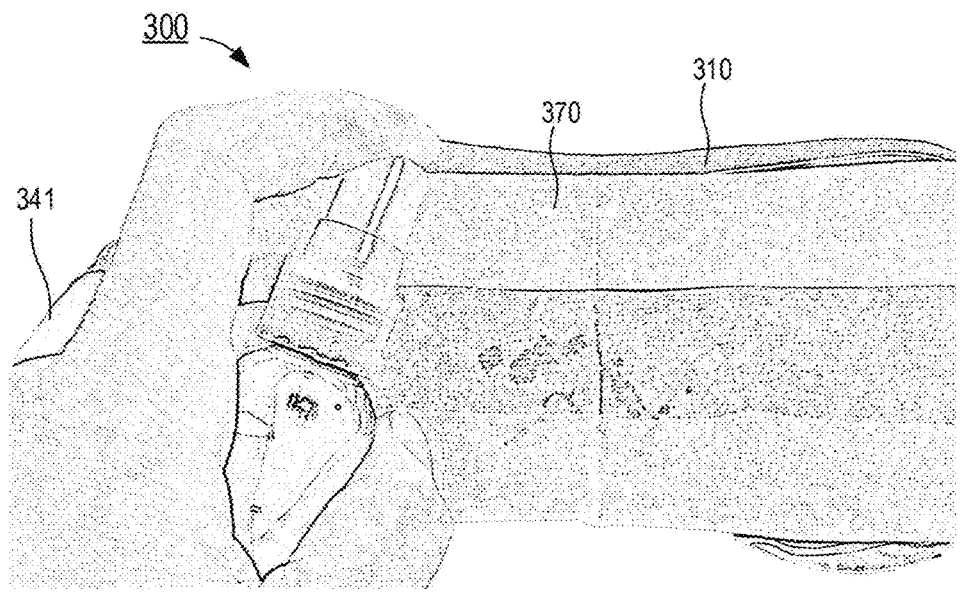
FIG. 36 is a rear view of a user spraying a fluid on the second insulating member of FIG. 33 while coupled to the therapeutic device of FIGS. 5 and 6.

In some instances, the second insulating member 370 can have a moisture content that can enhance the transfer of thermal energy between the ocular region of the user and the therapeutic member 305. For example, as shown in FIG. 36, the user can spray a fluid (e.g., water, saline, etc.) on the second insulating member 370 prior to coupling the therapeutic device 300 to his or her head. Thus, the fluid can enhance the transfer of thermal energy between the ocular region of the user and the therapeutic member 305. In some embodiments, the fluid can include and/or can otherwise be composed of, for example, an aqueous solvent, a facial botanical extract blend (e.g., Aloe Vera, cucumber extract, and/or the like), 1,3-Dimethylol-5,5-dimethylhydantoin (DMDM hydantoin), iodopropynyl butylcarbamate, propylene glycol, butylene glycol, and any suitable fragrance and/or aromatic agent. More specifically, in some embodiments, the fluid can include, for example, propylene glycol having a concentration of between about 0.1% and about 5.0%. In other embodiments, the fluid can have a concentration of propylene glycol of about 0.1%, about 0.25%, about 0.5%, about 0.75%, about 1.0%, about 1.25%, about 1.5%, about 1.75%, about 2%, about 2.25%, about 2.5%, about 2.75%, about 3.0%, about 3.25%, about 3.5%, about 4.0%, about 4.5%, or about 5%. In still other embodiments, the fluid can have a concentration of propylene glycol that is less than about 0.1% or greater than about 5.0%.

In some embodiments, the fluid can have a concentration of butylene glycol of between about 0.05% and about 3.0%. In other embodiments, the fluid can have a concentration of butylene glycol of about 0.1%, about 0.2%, about 0.3%, about 0.4%, about 0.5%, about 0.6%, about 0.7%, about 0.8%, about 0.9%, about 1.0%, about 1.25%, about 1.50%, about 1.75%, about 2.00%, about 2.50%, or about 3.0%. In still other embodiments, the fluid can have a concentration of butylene glycol of less than about 0.05% or greater than about 3.0%.

In some embodiments, the fluid can have a concentration of fragrance of between about 0.0025% and about 1.5%. In other embodiments, the fluid can have a concentration of fragrance of about 0.0025%, about 0.005%, about 0.0075%, about 0.01%, about 0.0125%, about 0.015%, about 0.02%, about 0.03%, about 0.04%, about 0.05%, about 0.06%, about 0.07%, about 0.08%, about 0.09%, about 0.10%, about 0.12%, about 0.14%, about 0.16%, about 0.18%, about 0.20%, about 0.22%, about 0.24%, about 0.26%, about 0.28%, about 0.30%, about 0.35%, about 0.40%, about 0.45%, about 0.50%, about 0.75%, about 1.0%, about 1.25%, or about 1.5%. In still other embodiments, the fluid can have a concentration of fragrance of less than about 0.0025% or greater than about 1.5%.

In some embodiments, the fluid can have a concentration of a facial botanical extract blend of between about 0.05% and about 3%. In embodiments, the fluid can have a concentration of a facial botanical extract blend of about 0.1%, about 0.2%, about 0.3%, about 0.4%, about 0.5%, about 0.6%, about 0.7%, about 0.8%, about 0.9%, about 1.0%, about 1.25%, about 1.50%, about 1.75%, about 2.00%, about 2.50%, or about 3.0%. In still other embodiments, the fluid can have a concentration of a facial botanical extract blend of less than about 0.05% or greater than about 3.0%.

The fluid can, in some embodiments, provide greater comfort to the user, by increasing the amount of moisture applied to the user's body. In some embodiments, the fluid can include an aromatic and/or therapeutic agent. Thus, spraying the second insulating member 370 with the fluid (i.e., that includes the aromatic and/or therapeutic agent) can increase the amount of the agent, such as a fragrance, contained in and/or suspended by the second insulating member 370. In some instances, the second insulating member 370 can be selectively sprayed with a fluid in one or more targeted locations along the second insulating member 370 which can be associated with, for example, a specific region and/or a corresponding anatomical structure. Moreover, in some instances, an area of the second insulating member 370 sprayed by a fluid can be increased or decreased by increasing or decreasing, respectively, a distance between the second insulating member 370 and, for example, a spray nozzle of a spray bottle. For example, in some instances, when disposed at a distance of around 0.25" from the second insulating member 370, a small mist atomizer of a size typically fitted to a spray bottle of around 2 to 4 ounces of fluid can deliver a spray of fluid to a substantially circular area of the second insulating member 370 with a radius of around 1.125". Similarly, in other instances, when such a sprayer is disposed at about 0.5" from the second insulating member 370, a substantially circular area with a radius of around 1.5" can be sprayed; when the sprayer is disposed at about 1" from the second insulating member 370, a substantially circular area with a radius of about 1.75" can be sprayed, and when the sprayer is disposed at about 1.5" from the second insulating member 370, a substantially circular area with a radius of about 2" can be sprayed.

In some instances in which a second insulating member 370, when disposed in a position of use on the therapeutic member 305 (as described above), covers a surface area of, for example, around 36 square inches, a spray radius of about 1.125" to 2.0" allows for delivery of a focused area of spray delivery, which can be, for example, about 3% to about 5.5% of the surface area of secondary insulating member 370. In this manner, a desired amount of fluid can be sprayed on a focused area of the second insulating member 370 at one or more target locations along the surface area of the second insulating member 370, where each target location can correspond to a particular anatomic region. Because the degree of moisture can furthermore affect the transfer of thermal energy that is transmitted from the therapeutic member 305, through secondary insulating member 370, and to the skin of the user, precise moisture control can, for example, enhance both convenience for the user and therapeutic outcomes of the therapeutic device 300. Although a specific range of spray radii is described above, in other embodiments, a broader or larger area of the secondary insulating member 370 can also be targeted by a spray.

Figure 37:
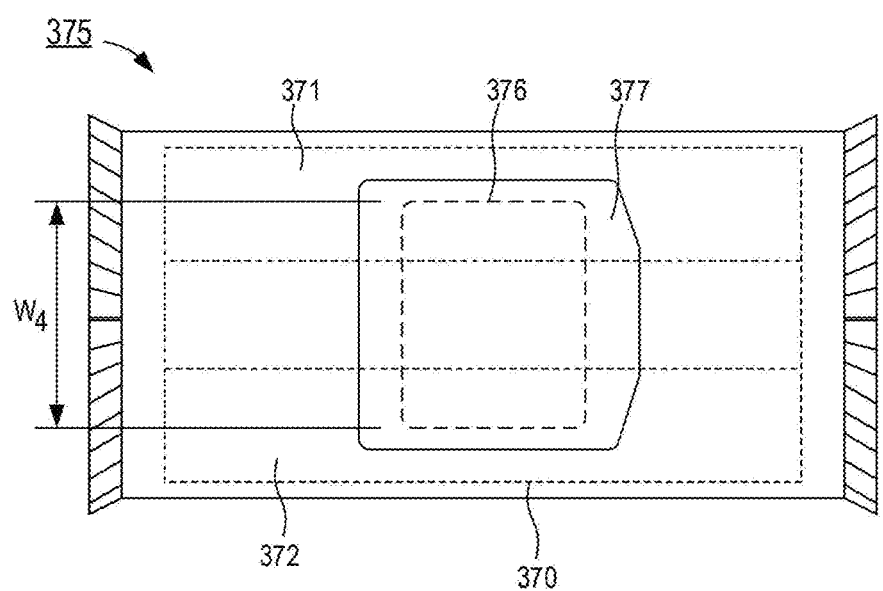
FIG. 37 is a top view of a package configured to house one or more of the second insulating members of FIG. 33 according to an embodiment.

In some instances, a manufacturer can, for example, manufacture a spray bottle (such as described above) and the second insulating member 370. In such instances, the spray bottle, one or more second insulating members 370, and instructions for use can be, for example, shipped and/or packaged together as a kit or shipped and/or packaged independently. For example, as shown in FIG. 37, in some embodiments, the second insulating member 370 can be stored in a sealable package 375. The sealable package 375 can be configured to store any number of second insulating members 370 in a substantially stacked configuration and can at least temporarily maintain a moisture level of the second insulating members 370 when sealed. In some instances, the sealable package 375 can be configured to maintain the second insulating members 370 with a first moisture content (i.e., level) that is lower than a second moisture content, whereby the second moisture content is the content typically recommended for use. In such instances, keeping relatively lower moisture content in the sealable package 375 of the second insulating members 370 can, for example, lower costs of manufacture and shipping, and can in some instances lower the risk of moisture dripping down a face of a user when in use. Such a lower moisture level can also improve the thermal insulation qualities of the second insulating member 370.

As shown in FIG. 37, the sealable package defines an opening 376 and includes a seal member 377. The sealable package 375 can be arranged such that the opening 376 exposes at least one of an edge of the first folded region 371 or the second folded region 372. The opening 376 can be any suitable shape, size, or configuration. For example, as shown, the opening 376 can expose an edge of first folded region 371 and an edge of second folded region 372. In embodiments, opening 376 can have a width $W_4$ sufficient to expose one or more edges of one or more folded regions (e.g., folded regions 371 and 372). For example, the width $W_4$ of the opening 376 can be about 1.25", about 1.5", about 1.75", about 2.0", about 2.25", about 2.5", about 2.75", or more, or any fraction therebetween. In one embodiment, the width $W_4$ of the opening 376 can be about 2.5". In some instances, the width $W_4$ of the opening 376 can be described as a percentage of the width of the package 375. For example, the width $W_4$ of the opening 376 can be about 30% of the width of the package 375, about 40% of the width of the package 375, about 50% of the width of the package 375, about 60% of the width of the package 375, or any percent or fraction of a percent therebetween. In some embodiments, the width $W_4$ of the opening 376 can be less than 30% of the width of the package 375 or can be greater than 60% of the width of the package 375. In one embodiment, the width $W_4$ of the opening 376 can be about 62.5% of the width of the package 375.

In some embodiments, the package 375 can include and/or be formed from a relatively flexible material and as such, can deform, deflect, and/or otherwise reconfigure when exposed to a force, thereby changing one or more dimensions thereof. Thus, in some instances, the width $W_4$ of the opening 376 can be described as a percentage of the width of, for example, the second insulating member 370 disposed in the package 375. For example, in some instances, the width $W_4$ of the opening 376 can be described as a percentage of the folded width of the second insulating member 370 (i.e., $(2*L_4+D_1)$, as described above). In other instances, the width $W_4$ of the opening 376 can be described as a percentage of the unfolded width of the second insulating member 370 (i.e., $(4*L_4+D_1)$, as described above). By way of example, in some embodiments, the width $W_4$ of the opening 376 can be about 30% of the folded width of the second insulating member 370, about 40% of the folded width of the second insulating member 370, about 50% of the folded width of the second insulating member 370, about 60% of the folded width of the second insulating member 370, or any percent or fraction of a percent therebetween. In some embodiments, the width $W_4$ of the opening 376 can be less than 30% of the folded width of the second insulating member 370 or can be greater than 60% of the folded width of the second insulating member 370. In one embodiment, the width $W_4$ of the opening 376 can be about 62.5% of the folded width of the second insulating member 370.

In some instances, the opening 376 can have and/or can define an area, where the area is a product of the length and the width of the opening 376. In some embodiments, the opening 376 can have an area of about 2.5 square inches (sq. in.), about 3.0 sq. in, about 3.5 sq. in, about 4.0 sq. in, about 4.5 sq. in., about 4.75 sq. in, about 5.0 sq. in, or any area or fraction of an area therebetween. In some embodiments, the area of the opening 376 can be less than 2.5 sq. in. or greater than about 5.0 sq. in. In one embodiment, the opening 376 can have and/or can define an area of around 5.0 sq in. Thus, a user can remove the second insulating member 370 by engaging a pick point or the like formed by a folded region, via the opening 376.

Although shown in FIG. 37 in a substantially open configuration, the seal member 377 can be moved relative to the opening 376 to substantially fluidically isolate an inner volume defined by the sealable package 375 from a volume outside of the sealable package 375. For example, in some embodiments, the seal member 377 can include an adhesive or the like that can form the substantially fluidic seal. In other embodiments, the seal member 377 can engage a surface of the sealable package 375 to form a friction or snap fit that can form the substantially fluidic seal. Thus, the second insulating members 370 can be maintained in an environment having suitable moisture content.

Figure 38:
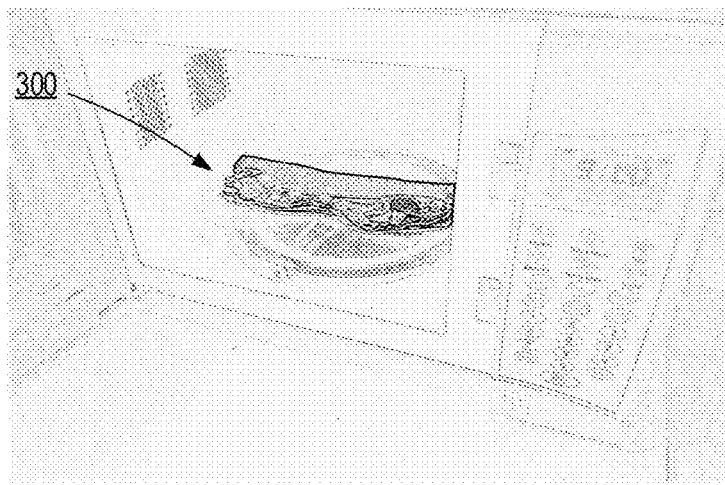
FIGS. 38 and 39 are illustrations of a method for transferring thermal energy to the therapeutic member included in the therapeutic device of FIGS. 5 and 6.
Figure 39:
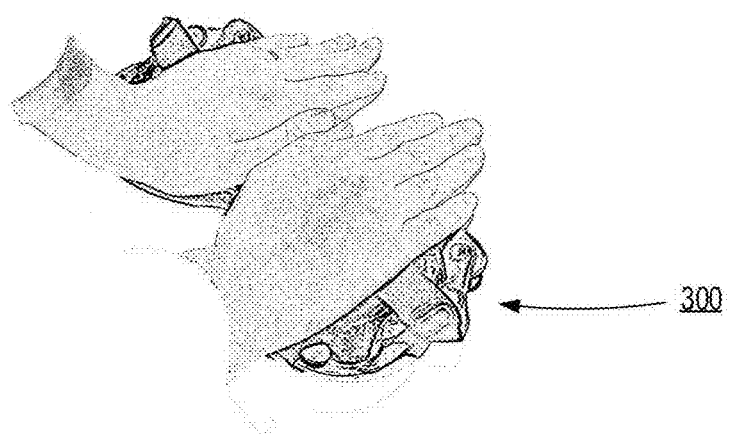

In use, the therapeutic member 305 can be coupled to the frame 310 and can be configured to, for example, receive thermal energy. In some embodiments, the therapeutic device 300 can be placed in a microwave oven, disposed in hot water, positioned in a heating device, electrically connected to an electrical source, and/or the like such that the potential thermal energy of the therapeutic member 305 is increased. As shown in FIG. 38, the therapeutic device 300 can be placed in a conventional microwave oven to receive energy that results in an increase of temperature of the therapeutic member 305. The therapeutic member 305 can be heated to any suitable temperature. For example, in some embodiments, the therapeutic device 300 can be placed in the microwave oven and activated on a "high" setting for about 15 seconds. The therapeutic device 300 can be removed from the microwave oven and can be, for example, massaged, pressed, mixed, or otherwise reconfigured to evenly distribute areas of relatively high or relatively low temperature. For example, in some embodiments, a user can systematically press on alternating portions of the therapeutic device 300 about 10 times, for a total of about 20 presses, as shown in FIG. 39. The therapeutic member 305 can then be configured to receive more thermal energy. For example, in some embodiments, the therapeutic device 300 is placed in the microwave oven for an additional 15 seconds on the "high" setting. Once completed, the user can again manipulate the therapeutic device 300 to evenly distribute areas of relatively high or relatively low temperature, as described above. If after the two rounds of heating and mixing the temperature of the therapeutic member 305 is insufficient, the user can adjust the timing at a subsequent heating, for example, by increasing the timing by about one or two seconds. The selection of two rounds of heating of 15 seconds each, followed by subsequent adjustment of as little as one or two seconds each time, was non-arbitrary and was based upon a four-part study, as described below.

In the first part of the study, it was determined through empirical testing that a more thorough distribution of heat in the contents included in the therapeutic member 305 (also referred to herein as "gel contents") could be obtained through the sequential heating, mixing, re-heating, and re-mixing of the gel contents than could be achieved through a single heating and mixing of the gel contents, even when the total duration of microwave heating and the total amount of mixing remained constant. Said another way, when a single round of microwave heating (of a first duration and energy setting) followed by a single round of mixing (of a first number of alternating impressions) was divided into two discrete sets of the same total length of heating and the same total number of alternating impressions, respectively, (i.e., within each of the two discrete sets of rounds, the length of heating and the number of alternating impressions were divided exactly in half relative to the single set of rounds), the thermal homogeneity of the gel contents was increased, relative to the method using a single round of heating and a single round of mixing.

In the second part of the study, detailed interviewing with test subjects and dry eye patients regarding instructions for preparing a microwave-heated therapeutic member (e.g., the therapeutic member 305) concluded that both initial comprehension and subsequent recall of directions for use was increased when, for example, the directions for use instructed users to perform two rounds of heating of equal time, rather than two rounds of heating at somewhat unequal times. A similar finding occurred regarding the number of alternating impressions performed in each of the two rounds performed to mix the therapeutic member after heating. For example, it was found to be easier for users to remember an instruction such as "heat twice, for 10 seconds each time," or "heat for 10 seconds a first time, and 10 seconds the next time" rather than, for example, "heat for 10 seconds a first time, and heat for 8 seconds the next time." Comprehension and subsequent recall was also improved when "round" numbers (e.g., 10, 15, 20, etc.) were used for both the duration of heating and number of alternating impressions, rather than "non-round" numbers (e.g., 11, 16, 19, etc.). The use of "round" numbers also allowed variations in the adjustment of heating-times mentioned above. For example, instead of increasing a heating-time from, for example, two rounds of 15 seconds to two rounds of 16 seconds or 17 seconds, the use of "round" numbers allowed users to increase a heating time from, for example, two rounds of 15 seconds to one round of 15 seconds and a second round of 20 seconds.

The third part of the study was conducted using numerous standardized therapeutic members of a uniform weight and volume using about seven ounces of gel product, and tested across 4 different microwave ovens. Three heating-and-mixing protocols were tested. The protocols tested two rounds of heating and mixing, with heating (on a "high" setting) placed at three time settings: 15 seconds, 20 seconds, and 25 seconds. The results were measured using a highly accurate electronic thermometer placed in contact with a surface of the therapeutic member. The results are shown in table 1 below:

TABLE 1

| Microwave Oven Characteristics | | | | Average Temperature (Fahrenheit) Achieved with Timing (secs + secs)* | | |
|---|---|---|---|---|---|---|
| Brand | Watts | Cu. In. | Age (Yrs) | 15 + 15 | 20 + 20 | 25 + 25 |
| Ewave | 1,000 | 1,046 | 9 | 103 | 114 | 123 |
| Emerson | 1,050 | 1,007 | 6 | 103 | 117 | 127 |
| Sharp | 1,000 | 1,063 | 4 | 110 | 121 | 135 |
| Cuisinart | 1,000 | 1,615 | 0.2 | 109 | 124 | 138 |
| AVERAGE: | | | | 106 | 119 | 131 |

As shown, the use of two rounds of 15 seconds of heating produced an average result of 106 degrees Fahrenheit (F), whereas the use of two rounds of 20 seconds of heating produced an average result of 119 degrees F. In some instances, a desired range of thermal application for eyelid heating is around 109 to 113 degrees F. Thus, in testing of the numerous 7-ounce therapeutic members (e.g., the therapeutic member 305) across 4 microwave ovens, the use of two rounds of 15 seconds of heating approached but did not exceed the normal lower bound of the target therapeutic temperature of 109 degrees F., whereas the use of two rounds of 20 seconds of heating did exceed the normal lower bound of the target therapeutic temperature of 109 degrees F.

In the fourth part of the study, scenarios of microwave-oven heating adjustment were discussed with users and were tested on the therapeutic members used in the third part of the study. It was found that a majority of users were apt to adjust a subsequent timing of microwave-oven activation based on a previous experience with, for example, a pre-scribed and/or recommended time of activation (i.e., heating), even though the result created a timing of activation that was other than a round number. Said another way, most users found it easy to comprehend and remember a method of use in which two microwave heatings of, for example, 15 seconds each, producing a temperature of the gel contents that was, in some instances, insufficient for user comfort, could be adjusted such that a subsequent set of two microwave heatings of, for example, 16 or 17 seconds each, in which the gel contents were slightly warmer than the previous heating of 15 seconds. It was found that allowing the gel pack to return substantially to room temperature after each set of heatings, and using the same microwave oven, improved the accuracy and reproducibility of the set of heatings, which aided user convenience by improving the efficiency of preparation.

In further testing, it was found that a stepwise, incremental increase in temperature over the course of a set of heatings resulted in, for example, improved safety of the heatings (e.g., reduced the likelihood of overheating that could otherwise be injurious) and gave the users a greater sense of control and mastery over their own experience with the therapeutic device (e.g., the therapeutic device 300). In some instances, such methods of a step-wise, precisely incremental increase in heating-time between uses of the device could also be applied to other heating methods, such as a method of heating a therapeutic member in hot water. Because adequate heating of a therapeutic member in hot water can take longer than, for example, heating of the therapeutic member in a microwave oven, the step-wise incremental increase in time can be on the order of, for example, 5 or 10 seconds rather than, for example, the 1 or 2 second increase associated with microwave heating. While each of the above methods or steps added incrementally to improvements in the use of the therapeutic device, the communication of two or more of the methods or steps, in the form of instructions for the sequential performance of such methods or steps, can be made to users. In some instances, it was found that instructions regarding the sequential performance of the methods or steps (described above) enabled users, ranging in age from 24 to 84, to employ a reliable course of action and rapidly achieve mastery over the therapeutic member preparation. Test subjects reported that the device was "easy and simple" to use and gave highly satisfying results. At least a part of the data from such empirical testing is described in further detail herein.

In some instances, the first insulating member 360 can be coupled to the frame 310 after the thermal energy is transferred to the therapeutic member 305 (such as, for example, by the methods described above). In other instances, the first insulating member 360 can be coupled to the frame 310 prior to thermal energy being transferred to the therapeutic member 305. Similarly, the second insulating member 370 can be coupled to the frame 310 and/or the therapeutic member 305 before or after the thermal energy is transferred to the therapeutic member 305. In some instances, the user can spray the second insulating member 370 to increase a moisture content of the second insulating member 370, regardless of an initial hydration level of the second insulating member 370 (such as, for example, a hydration level maintained when the second insulating member 370 is disposed in a sealable package or the like). Similarly, the user can spray the second insulating member 370 to increase a chemical content (e.g., a fragrance, therapeutic agent, or the like) of the second insulating member 370, regardless of an initial chemical content. Said another way, in some instances, the second insulating member 370 can be manufactured and packaged with a first level of moisture content and/or chemical content, and despite the manufactured level of moisture content and/or chemical content spray, the user can spray the second insulating member 370 with a spray that can add to, for example, a moisture content and/or a chemical content according to a user's choosing.

Figure 40:
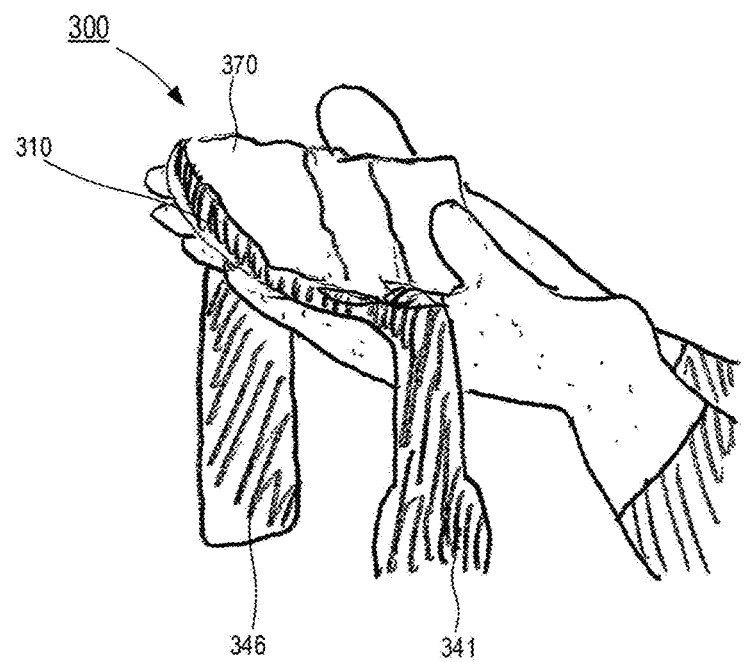
FIGS. 40 and 41 are illustrations of a method for coupling the therapeutic device of FIGS. 5 and 6 to the head of a user.
Figure 41:
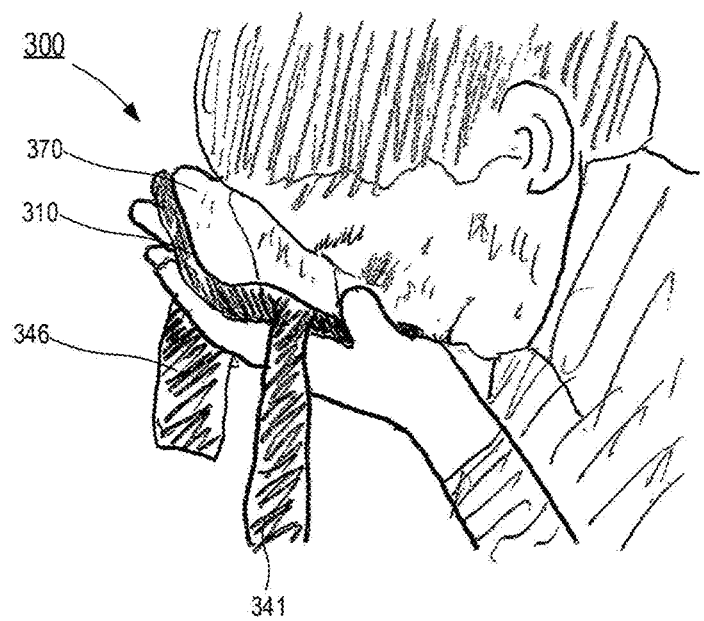

With the desired amount of thermal energy transferred to the therapeutic member 305, the user can move the therapeutic device 300 to place the therapeutic member 305 in contact with, for example, the ocular region, as shown in FIGS. 40 and 41. In some embodiments in which therapeutic member 305 is filled with a gelatinous substance such as an aqueous gelatinous substance, the contents (i.e., the gelatinous substance) of the therapeutic member 305 tend to flow in response to an applied force such as, for example, gravity. Thus, for example, when therapeutic device 300 is in a position of use against the face of a user (e.g., a substantially vertical position as shown in FIGS. 10-12), the contents within therapeutic member 305 flow toward lower regions of the face (e.g., such as those positioned near the cheeks of the user) and away from upper regions of the face (e.g., such as those positioned near the eyes of the user). Such a repositioning of the contents can, for example, reduce a volume of the contents available for conductive thermal contact with the eyes of the user.

In some instances, to increase a volume of the contents available for conductive thermal contact with the eyes of the user, a user can hold therapeutic device 300 in a horizontal position (see e.g., FIG. 40). In this position, the contents can be more evenly spread throughout therapeutic member 305 such that areas corresponding to the upper regions and the lower regions (e.g., associated with the eyes and the cheeks, respectively) contain roughly equal amounts and/or volumes of the gelatinous contents. In this manner, maintaining the therapeutic device 300 in a horizontal position and bringing the face into a roughly horizontal position prior to application to the face can result in a greater amount and/or volume of the contents of the therapeutic member 305 that are placed in thermal contact with the eye region than would otherwise result from application of the therapeutic device 300 in a substantially vertical configuration. In some instances, a user can enhance conductive thermal contact of the gelatinous content with the eye region by pressing upon the therapeutic member 305 to achieve greater apposition with the eye regions, prior to elevating the head to a vertical position.

Although some degree of gravitational repositioning of the gelatinous substance can result from the user lifting his or her head from a substantially horizontal position to a substantially vertical position, the degree of gravitational repositioning can be reduced by, for example, maintaining a pressure between a portion of the therapeutic device 300 and a portion of the face (e.g., a portion of the therapeutic device 300 that is associated with and/or substantially aligned with the eye region). In this manner, the pressure exerted by the user can compress the gelatinous content of the therapeutic member 305 against the face (including the cheek regions) and can force the gelatinous contents upwards toward the eye region. Thus, a greater amount and/or volume of thermal material (e.g., the gelatinous contents) is displaced upwards toward the eye region and maintained in conductive thermal contact with the eye region due to the compression of lower regions of therapeutic member 305 against the cheek regions of the user than can otherwise result from placing the therapeutic member 305 in conductive thermal contact with the eye region when the face of the user is in a substantially vertical position.

A head-down position of application (e.g., a horizontal position) can also allow the second insulating member 370 (and/or other suitable moist disposable non-woven fibrous fabric sheet) to stay in position on the therapeutic member 305 prior to use without, for example, being mechanically coupled thereto and regardless of, for example, a moisture content of the second insulating member 370 (e.g., a relatively low moisture content can reduce a surface friction between the second insulating member 370 and a surface of the therapeutic member 305). In some instances, a user can maintain a head-down position and/or a head-bent-forward position even after the therapeutic member 305 is in a stable position in relation to the user's face. In some such instances, a user can maintain the head down position and/or the head-bent-forward position to, for example, reduce a pressure exerted by the therapeutic member 305 on the eye region that can otherwise result from the face supporting at least a portion of the weight of the therapeutic member 305.

Once in the desired position, the coupling portion 340 can be transitioned from its first configuration to its second configuration to couple the therapeutic device 300 to the head of the user. Thus, thermal energy can be transferred from the therapeutic member 305 to the ocular region. Moreover, the arrangement of the therapeutic device 300 can be such that the transfer of the thermal energy is substantially uniform on a desired target area of the ocular region. In addition, the force exerted by the therapeutic member 305 on the ocular region can be distributed and/or diffused in such a manner as to increase the comfort of the user while using the therapeutic device 300. More specifically, the arrangement of the frame 310 can be such that when the therapeutic device 300 is coupled to the head of the user, at least part of the side portion 315 of the frame 310 (e.g., the superotemporal region 316 and/or the centrolateral region 317) can bend, flex, or otherwise reconfigure in such a manner that a force exerted on the ocular region of the user by the therapeutic device 300, or for example by the therapeutic member 305, is reduced. Similarly, the arrangement of the first insulating member 360 in its second configuration is such that the therapeutic member 305 is allowed to extend through the apertures 325 defined by the frame 310 without the first insulating member 360 exerting undue force of the anterior surface of the therapeutic member 305. Thus, the first insulating member 360 can provide thermal insulation without exerting undue force that can otherwise lead to discomfort for the user.

During use of the therapeutic device 300, the thermal energy potential (e.g., a difference in temperature) between the therapeutic member 305 and the ocular region of the user is naturally reduced. In some instances, such a reduction in thermal energy potential can occur in and/or at, for example, peripheral regions of the contents of the therapeutic member 305 that are in closer thermal contact with an outer surface or casing containing the contents at a faster rate than more centrally located regions. More specifically, in some instances, thermal energy can be transferred from the relatively hotter surface of the therapeutic member 305 to an external volume of relatively cooler air via, for example, convection heat transfer. Thermal energy can also be transferred from the relatively hotter surface of the therapeutic member 305 to the external surface of the user's skin via, for example conductive heat transfer, wherein the heat transferred to the user's skin is then dispersed to other areas of the user's body through, for example, the action of the user's blood circulation. In contrast, thermal energy is transferred from more centrally located regions of the contents to more peripherally located regions of the contents substantially via, for example, conduction heat transfer. Thus in some instances, the thermal energy potential between the peripheral regions of the contents of the therapeutic member 305 and the eye region can be reduced at a faster rate than, for example, the thermal energy potential between the central regions of the contents and the eye region.

Figure 42:
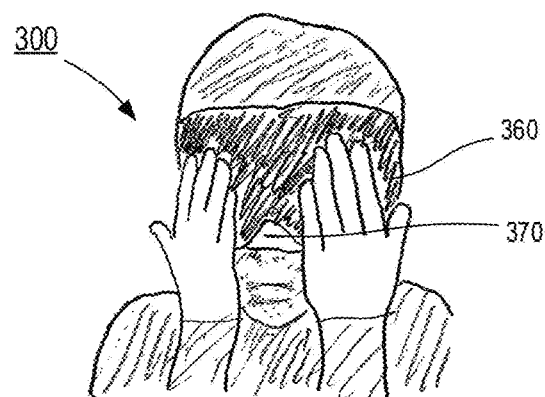
FIGS. 42 and 43 are illustrations of a method for increasing a thermal output and a compressive force of the therapeutic member when the therapeutic device of FIGS. 5 and 6 is coupled to the head of the user.
Figure 43:
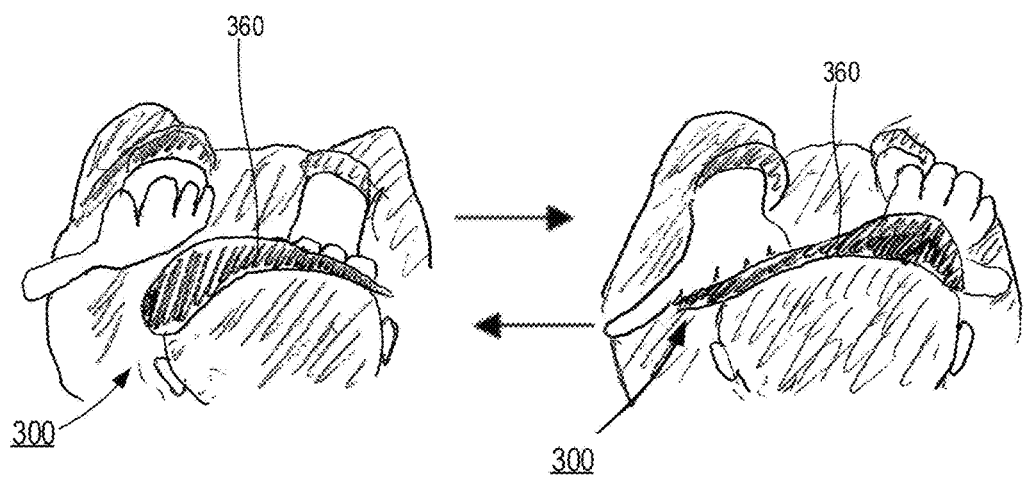

As shown in FIGS. 42 and 43, in some instances, the user can press in an alternating manner upon a portion of the therapeutic device 300 associated with, for example, the left eye and a portion of the therapeutic device 300 associated with, for example, the right eye. In this manner, areas of relatively higher temperature or relatively lower temperature can be diffused in the therapeutic member 305, which in turn, can increase the thermal energy transfer between the therapeutic member 305 and the ocular region of the user. For example, such alternating pressure exerted on the therapeutic member 305 can, in some instances, redistribute the contents of the therapeutic member 305. More specifically, relatively warmer volumes and/or particles of the contents originally disposed in more central locations of the therapeutic member 305 and relatively cooler volumes and/or particles of the contents originally disposed in more peripheral locations of the therapeutic member 305 (as described above) are redistributed within a volume defined by the therapeutic member 305. In this manner, the application of pressure in the alternating manner can, for example, increase a thermal homogeny within the therapeutic member 305. In some instances, such alternating pressure can be modified by the user in order to produce a thermal experience controlled instantaneously by the user. Such a method of use can also extend the user's experience of a useful treatment of thermal application, that might otherwise be inconvenienced by the therapeutic interruption associated with, for example, re-heating the therapeutic member 305 to an acceptable temperature.

In some instances, an action of pressing in an alternating manner upon portions of the therapeutic device 300 can result in pulsating alterations in the pressure transmitted to the ocular regions of the user. Such alterations in pressure can, for example, be transmitted to the eyelid regions and thus, to the meibomian glands, resulting in a form of eyelid treatment that is commonly known as "eyelid massage." Imparting such alternating differences in pressure can be distinct from or occur simultaneously with the aforementioned diffusion of temperature. Imparting such "eyelid massage" through the content of the therapeutic device 305, such as a gelatinous substance capable of thermal adjustment, can result in a more gentle and safe compression of the meibomian glands than is otherwise available through the more commonly-recommended methods of "eyelid massage," often employing direct and sometimes uncomfortable and/or unhygienic manipulation of the eyelids with the fingers. In some instances, a synergy of both pressure and temperature application to the eyelids can result from the application of the alternating pressure described above. In some embodiments, the therapeutic member 305 can include and/or can be otherwise packaged with instructions associated with the application of pressure in the alternating manner described above.

Figure 44:
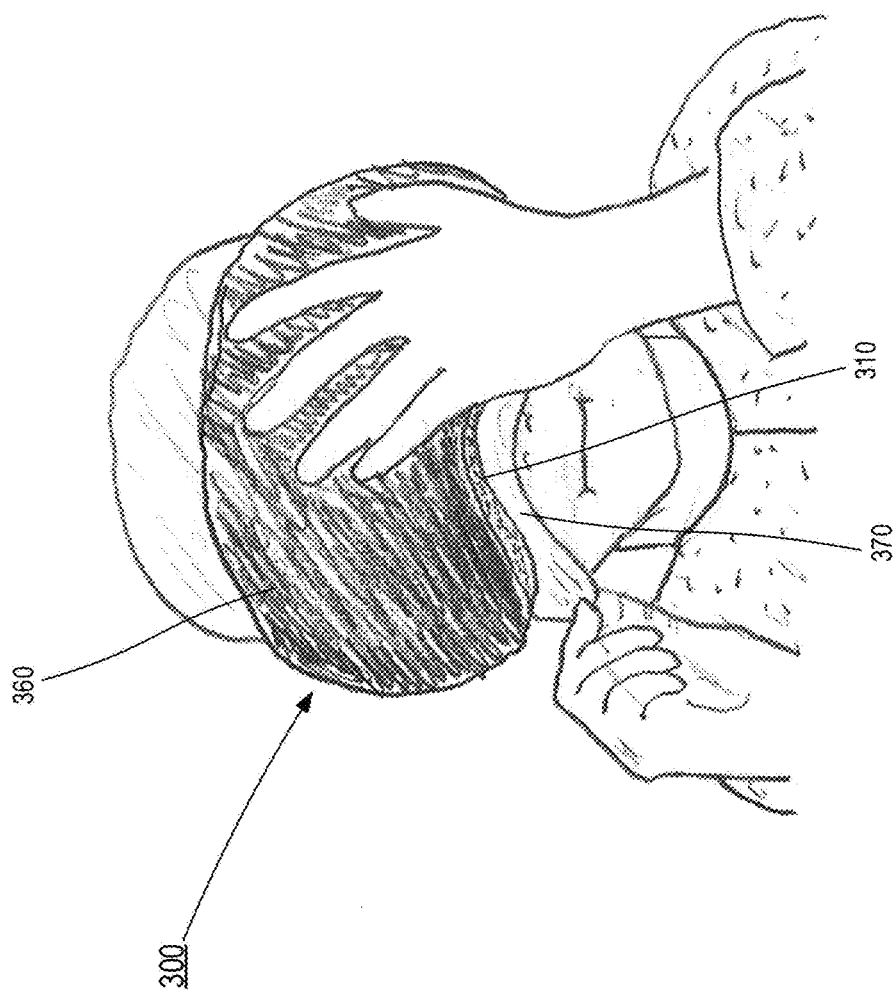
FIG. 44 is an illustration of a method for removing the second insulating member of FIG. 33 from the therapeutic device of FIGS. 5 and 6 when the therapeutic device is coupled to the head of the user.

As shown in FIG. 44, in some instances, the user can remove the second insulating member 370 from the contact with the therapeutic device 300 and/or the ocular region of the user. Said another way, the user can remove the second insulating member 370 from a position in which insulating member 370 is interposed or sandwiched between therapeutic member 305 and the user's ocular region while therapeutic device 300 is applied to the user's face in a position of use. For example, the user can grasp a portion of the second insulating member 370 and pull the second insulating member 370 from its position between the user and the therapeutic member 305. Thus, the thermal insulation that was provided by the second insulating member 370 is removed, which can result in an increase in thermal energy transfer between the ocular region of the user and the therapeutic member 305. Such a method can be used, for example, once a user has determined that the temperature of treatment has been reduced below a subjective threshold that would ordinarily prompt a user to re-heat the therapeutic member 305. Thus, the removal of the second insulating member 370 can, for example, prolong the thermal therapy to the eye region of the user, during a treatment. In some instances, following further thermal energy transfer from therapeutic device 305 to the user and/or the surrounding environment, the user may again apply a pressure in an alternating manner upon the therapeutic device 300, as discussed above. Once the desired amount of thermal energy is transferred between the ocular region of the user and the therapeutic member 305, the user can engage the coupling portion 340 of the therapeutic device 300 to remove the therapeutic device 300 from the head of the user. For example, the user can move the coupling portion 340 from the second configuration to the first configuration by decoupling the first strap 341 from the second strap 346.

Although the therapeutic device 300 is particularly shown in FIGS. 5-44, a therapeutic device can be any suitable configuration and can include any combination of components that can be similar to components of the therapeutic device 300. For example, FIGS. 45-60 illustrate various configurations of flexible frames that can be included in, for example, the therapeutic device 300 or the like, according to specific embodiments. As described in further detail herein, portions of the flexible frames can be changed, modified, altered, etc. to result in a desired set of characteristics when used in a therapeutic device.

Figure 45:
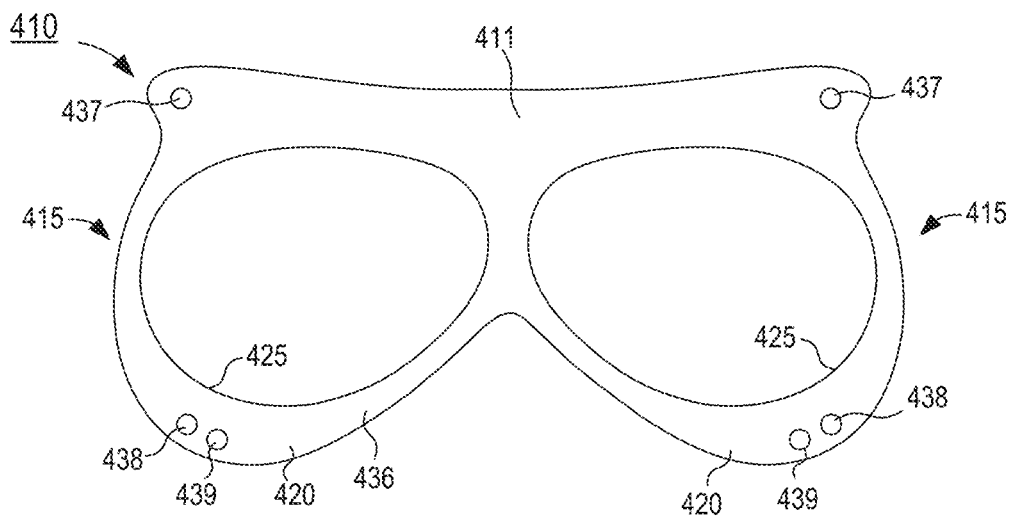
FIGS. 45-49 are front views of a flexible frame included in a therapeutic device according to other embodiments.

For example, FIG. 45 illustrates a flexible frame 410 that defines a set of apertures 425. The flexible frame 410 includes a top portion 411, a side portion 415, and an inferior portion 420. The flexible frame 410 can be substantially similar to the flexible frame 310 in function. For example, the flexible frame 410 can be configured to support a therapeutic member (e.g., the therapeutic member 305) that can be applied, for example, to the ocular region of a user. The flexible frame 410 can differ from the flexible frame 310, however, in the arrangement of an anterior surface 436. For example, as shown in FIG. 45, the anterior surface 436 of the flexible frame 410 includes a first set of posts 437, a second set of posts 438, and a third set of posts 439 that can collectively couple an insulating member (e.g., the first insulating member 360) to the flexible frame 410. The first set of posts 437 can be substantially similar in form and function as the first set of posts 337 included in the flexible frame 310. The arrangement of the second set of posts 438 and the third set of posts 439, however, can differ in form and function from the second set of posts 338 of the flexible frame 310. For example, while the second set of posts 338 of the flexible frame 310 are configured to be inserted into the opening 364 defined by the first leaflet 365 and the opening 364 defined by the second leaflet 366 (see e.g., FIGS. 29-30), the second set of posts 438 and the third set of posts 439 can each be coupled independently to a first leaflet and a second leaflet, respectively. Such an arrangement can, for example, reduce and/or eliminate an overlapping portion of an insulating member when coupled thereto (see e.g., FIGS. 29 and 30 with reference to the first insulating member 360). In some embodiments, the reduction and/or elimination of the overlapping portion can result in, for example, an increase in flexibility of at least a portion of the insulating member, which in turn, can reduce rearward pressure against the therapeutic member, and hence against the eyes of the user.

Figure 46:
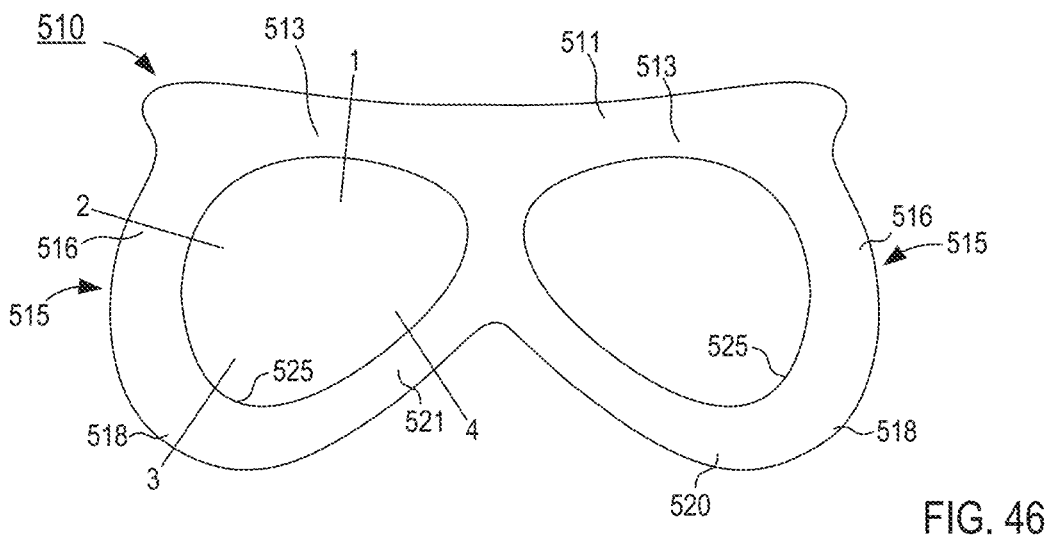

FIG. 46 illustrates a flexible frame 510 that defines a set of apertures 525, according to another embodiment. The flexible frame 510 includes a top portion 511 having a superior region 513 disposed above each aperture 525; a side portion 515 having a superotemporal region 516 and an inferotemporal region 518; and an inferior portion 520 having an inferomedial region 521. The flexible frame 510 can be substantially similar to the flexible frame 310 in function. For example, the flexible frame 510 can be configured to support a therapeutic member (e.g., the therapeutic member 305) that can be applied, for example, to the ocular region of a user. The flexible frame 510 can differ from the flexible frame 310, however, in that the superior region 513, the side portion 515, and the inferior portion 520 have a substantially similar width. Similarly stated, the superotemporal region 516 and/or the inferomedial regions 521 are not narrowed as described above with reference to the flexible frame 310.

The flexible frame 510 can be formed from a substantially flexible material such as those described above. In some embodiments, the flexible frame 510 can have a thickness that can, for example, provide a suitable level of flexibility. For example, the flexible frame 510 can have a thickness that is less than a thickness of the flexible frame 310. More specifically, in some embodiments, the flexible frame 510 can be formed using a manufacturing process that can result in the thickness of the flexible frame 510 that is less than the thickness resulting from the manufacturing process used to form the flexible frame 310 (e.g., injection molding). As such, at least a part of the side portion 515 can bend, flex, and/or deform in a convex manner (as described above) that would otherwise be limited if the thickness of the flexible frame 510 was similar to the thickness of the flexible frame 310. Thus, a region disposed between a set of attachment points (not shown in FIG. 46) can outwardly bend in the anterior direction as described above with reference to the centrolateral region 317 of the frame 310. In this manner, the bending of the side portion 515 can be operable in reducing rearward pressure against the therapeutic member, and hence against the user's eyes, as described in detail above with reference to the frame 310.

Although the flexible frame 510 is described above as having a desired level of flexibility by having a thickness that is less than the thickness of the flexible frame 310, in other embodiments, the flexibility of a flexible frame can be increased or decreased by selectively narrowing or widening, respectively, one or more portions of the flexible frame.

Figure 47:
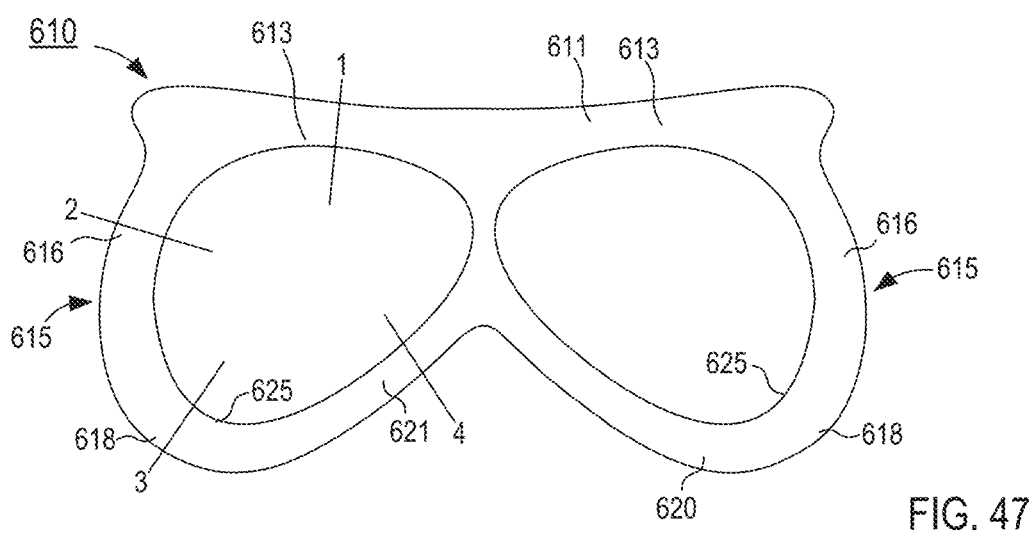

For example, FIG. 47 illustrates a flexible frame 610 that defines a set of apertures 625 according to another embodiment. The flexible frame 610 includes a top portion 611 having a superior region 613 disposed above each aperture 625; a side portion 615 having a superotemporal region 616 and an inferotemporal region 618; and an inferior portion 620 having an inferomedial region 621. The flexible frame 610 can be substantially similar to the flexible frame 310 in function. Moreover, the flexible frame 610 can be formed from a relatively flexible material with a thickness that is substantially similar to the thickness of the flexible frame 310. In this manner, the flexible frame 610 can be configured to support a therapeutic member (e.g., the therapeutic member 305) that can be applied to an ocular region of a user, as described above.

The flexible frame 610 can differ from the flexible frame 310, however, in the width of the superior region 613, the side portion 615, and the inferomedial portion 621. For example, as shown in FIG. 47, the top portion 611, the side portion 615, and the inferomedial portion 621 are narrowed relative to the flexible frame 510 yet the side portion 615 and the inferomedial portion 621 are not as narrow as the flexible frame 310. In this manner, at least a part of the side portion 615 can bend, flex, and/or deform in a convex manner (as described above) that would otherwise be limited if the flexible frame 610 was not narrowed. With the flexible frame 610 having a similar thickness as the thickness of the flexible frame 310, however, the flexible frame 610 can be more rigid (e.g., less flexible) than the flexible frame 310. Thus, the flexible frame 610 can be configured to increase a rearward pressure against the therapeutic member, and hence against the user's eye, relative to the flexible frame 310.

Figure 48:
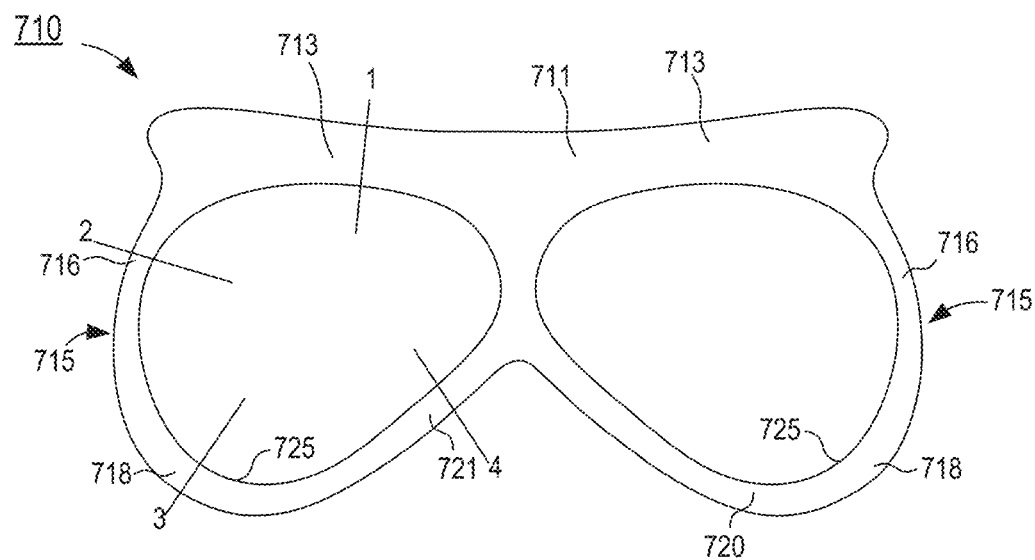

FIG. 48 illustrates a flexible frame 710 that defines a set of apertures 725 according to another embodiment. The flexible frame 710 includes a top portion 711 having a superior region 713 disposed above each aperture 725; a side portion 715 having a superotemporal region 716 and an inferotemporal region 718; and an inferior portion 720 having an inferomedial region 721. The flexible frame 710 can be substantially similar to the flexible frame 310 in function. Moreover, the flexible frame 710 can be formed from a relatively flexible material with a thickness that is substantially similar to the thickness of the flexible frame 310. In this manner, the flexible frame 710 can be configured to support a therapeutic member (e.g., the therapeutic member 305) that can be applied to an ocular region of a user, as described above.

The flexible frame 710 can differ from the flexible frame 310 however, in the width of the superior region 713, the side portion 715, and the inferior portion 720. For example, as shown in FIG. 48, the top portion 711, the side portion 715, and the inferior portion 720 are narrower than the flexible frame 310. Moreover, the narrowing is substantially consistent around the periphery (e.g., a substantially equal narrowing of the side portion 715 and the inferior portion 720). In this manner, at least a part of the side portion 715 can bend, flex, and/or deform in a convex manner (as described above) that would otherwise be limited if the flexible frame 710 was not narrowed. With the flexible frame 710 having a similar thickness as the thickness of the flexible frame 310, however, the flexible frame 710 can be more flexible (e.g., less rigid) than the flexible frame 310. Thus, the flexible frame 710 can be configured to decrease a rearward pressure against the therapeutic member, and hence against the eye region of the user, relative to the flexible frame 310. Moreover, by narrowing the inferotemporal region 718, a force exerted by the inferotemporal region 718 that supports and/or pushes a portion of the therapeutic member towards the ocular region can be reduced relative to the flexible frame 310. In addition, by narrowing the inferotemporal region 718, for example, a surface area of a region of flexible frame 710 can be reduced relative to a flexible frame with less narrowing, such as flexible frame 310. The reduction of a surface area of a region of the flexible frame 710 can result in a lower total displacement of the volume of the contents of a therapeutic member such as therapeutic member 305. Thus, for example, the flexible frame 710 having the inferotemporal region 718 that is not as wide as the inferotemporal region 318 of the flexible frame 310, displaces a lesser volume of the contents of therapeutic member 305 even when, for example, equal amounts of force are applied to both the flexible frames 310 and 710 (e.g., from coupling members, such as the coupling members 340, coupled thereto).

Table 2 illustrates a comparison of the superior region (identified by the line segment 1), the superotemporal region (identified by the line segment 2), the inferotemporal temporal region (identified by the line segment 3), and the inferomedial region (identified by the line segment 4) of the flexible frames 310, 510, 610, and 710. In Table 2, the width in millimeters of the identified regions is shown and is also presented as a percentage of the superior region 1.

TABLE 2

| | Flexible Frame 310 (FIG. 9) | | Flexible Frame 510 (FIG. 46) | | Flexible Frame 610 (FIG. 47) | | Flexible Frame 710 (FIG. 48) | |
|---|---|---|---|---|---|---|---|---|
| | Width | % | Width | % | Width | % | Width | % |
| 1 | 18.0 mm | 100% | 18.5 mm | 100% | 13.3 mm | 100% | 18.0 mm | 100% |
| 2 | 6.2 mm | 34% | 20.0 mm | 108% | 14.8 mm | 111% | 7.0 mm | 39% |
| 3 | 19.2 mm | 107% | 22.2 mm | 120% | 17.0 mm | 128% | 8.5 mm | 47% |
| 4 | 7.0 mm | 39% | 12.4 mm | 67% | 9.0 mm | 68% | 6.3 mm | 35% |

As described above, in some embodiments, the inferotemporal region (identified by the line segment 3) can exert a force on a therapeutic member (e.g., the therapeutic member 305), and can also displace a volume of the contents of a therapeutic member, that can push and/or direct a portion, or a volume of the contents, of the therapeutic member toward the ocular region of the user. As such, an increase or decrease in the width of the inferotemporal region can, for example, increase or decrease, respectively, the force exerted on the therapeutic member as well as increase or decrease, respectively, the volume of displacement of the contents of the therapeutic member. Accordingly, Table 3 below presents the width of the identified regions and a percentage of the region relative to the inferotemporal region (identified by the line segment 3).

TABLE 3

| | Flexible Frame 310 (FIG. 9) | | Flexible Frame 510 (FIG. 46) | | Flexible Frame 610 (FIG. 47) | | Flexible Frame 710 (FIG. 48) | |
|---|---|---|---|---|---|---|---|---|
| | Width | % | Width | % | Width | % | Width | % |
| 1 | 18.0 mm | 94% | 18.5 mm | 83% | 13.3 mm | 78% | 18.0 mm | 212% |
| 2 | 6.2 mm | 32% | 20.0 mm | 90% | 14.8 mm | 87% | 7.0 mm | 82% |
| 3 | 19.2 mm | 100% | 22.2 mm | 100% | 17.0 mm | 100% | 8.5 mm | 100% |
| 4 | 7.0 mm | 36% | 12.4 mm | 56% | 9.0 mm | 53% | 6.3 mm | 74% |

Although Tables 2 and 3 illustrate specific values and/or relationships of the regions of the superior regions, the superotemporal regions, the inferotemporal temporal regions, and the inferomedial regions of the flexible frames 310, 510, 610, and 710, in other embodiments, a flexible frame can include regions of any suitable width and/or relative width (e.g., relative to the superior region and/or the inferotemporal region).

Figure 49:
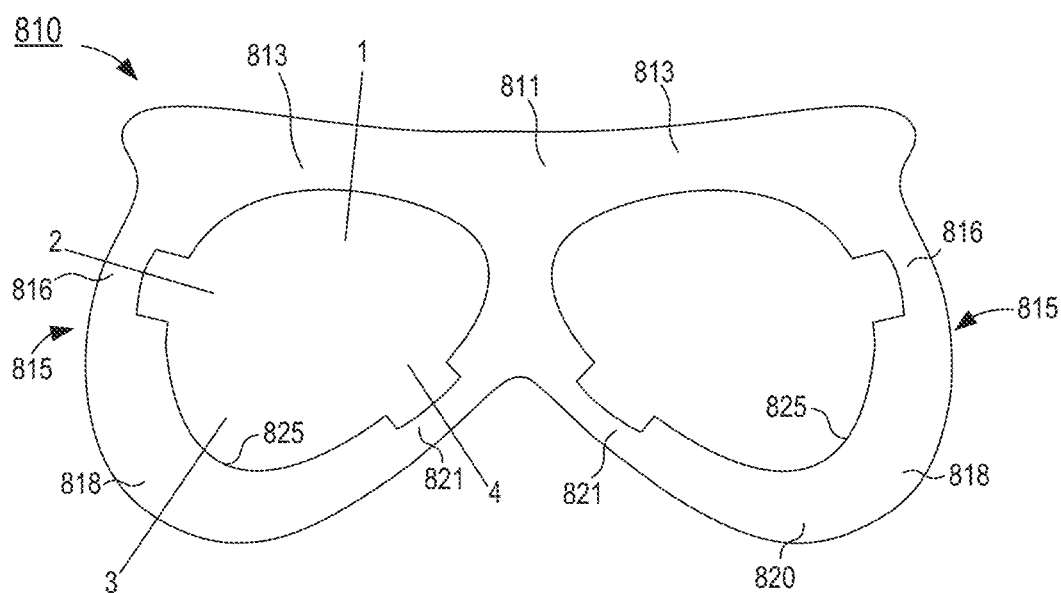
Figure 50:
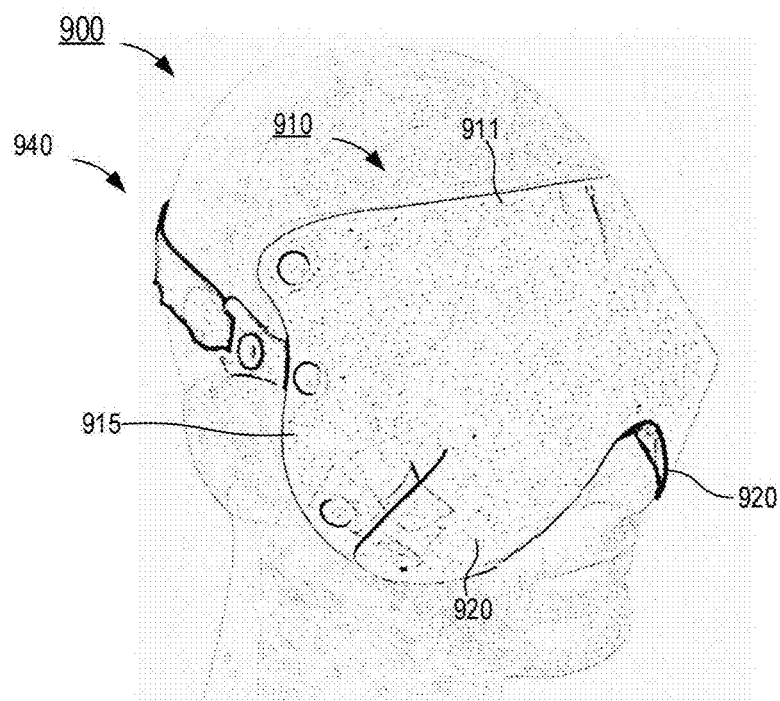
FIG. 50 is a perspective view of a therapeutic device coupled to a portion of the body according to another embodiment.

Although the flexible frames 310, 410, 510, 610, and 710 are shown and described as having a width that forms a substantially gradual transition from a region with a smaller width to a region with a larger width, in other embodiments, a flexible frame can include selective narrowing of one or more regions of the flexible frame that can have a relatively abrupt transition. For example, FIG. 49 illustrates a flexible frame 810 that defines a set of apertures 825 according to another embodiment. The flexible frame 810 includes a top portion 811 having a superior region 813 disposed above each aperture 825; a side portion 815 having a superotemporal region 816 and an inferotemporal region 818; and an inferior portion 820 having an inferomedial region 821. The flexible frame 810 can be substantially similar to the flexible frame 310 in function. Moreover, the flexible frame 810 can be formed from a relatively flexible material with a thickness that is substantially similar to the thickness of the flexible frame 310. In this manner, the flexible frame 810 can be configured to support a therapeutic member (e.g., the therapeutic member 305) that can be applied to an ocular region of a user, as described above.

As described above, the superotemporal region 816 and the inferomedial region 821 can be narrowed to increase the flexibility of the flexible frame 810. The flexible frame 810 can differ from the flexible frame 310 however, in that the superotemporal region 816 and the inferomedial region 821 include a relatively abrupt narrowing. In such embodiments, the relatively abrupt narrowing of the superotemporal region 816 and the inferomedial region 821 can be sufficient to provide a desired flexibility of the superotemporal region 816 and the inferomedial region 821. In this manner, at least a part of the side portion 815 can bend, flex, and/or deform in a convex manner (as described above) that would otherwise be limited if the flexible frame 810 was not narrowed. Moreover, the relatively abrupt narrowing of the superotemporal region 816 and the inferomedial region 821 can form, for example, a stress concentration riser or the like that can form a point or axis about which the superotemporal region 816 and the inferomedial region 821 can deform. Thus, the flexible frame 810 can be configured to decrease a rearward pressure against the therapeutic member, and hence against the user's eye, than would otherwise result from a smaller amount of narrowing and/or no narrowing of the superotemporal region 816 and the inferomedial region 821. Moreover, by selectively narrowing the superotemporal region 816 and the inferomedial region 821, the inferotemporal region 818 can have a width that is sufficient to exert a force on the therapeutic member to support and/or push a portion of the therapeutic member toward the ocular region of the user, as described above with reference to the flexible frame 310.

Although the flexible frames 310, 410, 510, 610, 710, and 810 are shown and described as defining the apertures 325, 425, 525, 625, 725, and 825, respectively, that substantially correspond to the ocular regions (e.g., the left eye and the right eye) of the user, in some embodiments, a therapeutic device can include a frame that does not include apertures. For example, FIGS. 50-54 illustrate a therapeutic device 900 according to another embodiment. The therapeutic device 900 can be used to place a therapeutic member 905 (see e.g., FIG. 54) in contact with a target region of the body of a user such as, for example, the ocular region of the face of the user. The therapeutic device 900 includes a frame 910 and a coupling portion 940. The coupling portion 940 can be substantially similar to or the same as the coupling portion 340 described above with reference to FIGS. 12-24. In this manner, the coupling portion 940 can be coupled to the frame 910 and can be transitioned from a first configuration to a second configuration to couple the therapeutic device 900 to the head of the user (see e.g., FIG. 50), as described in detail above. Thus, the coupling portion 940 is not described in further detail herein.

Figure 51:
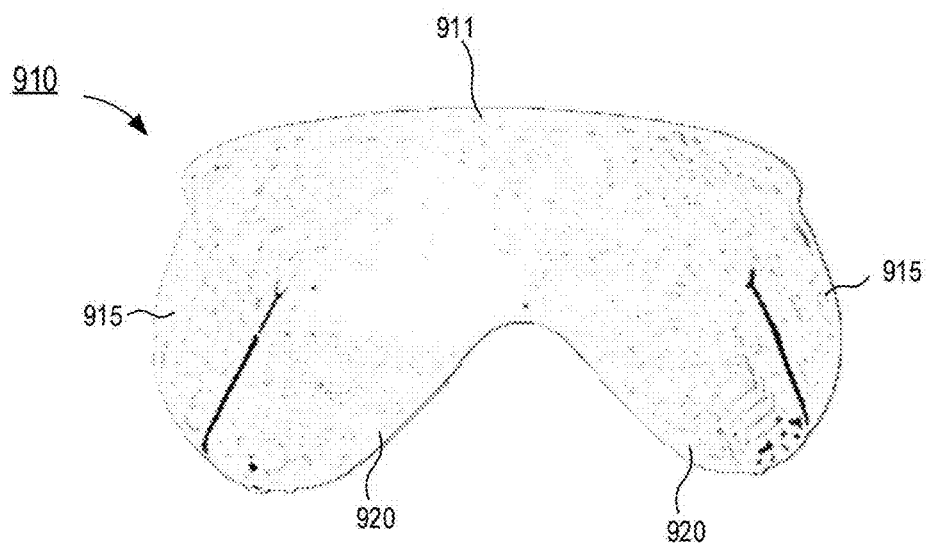
FIGS. 51-53 are a front perspective view, a front view, and a bottom perspective view, respectively, of a flexible frame included in a therapeutic device according to another embodiment.
Figure 52:
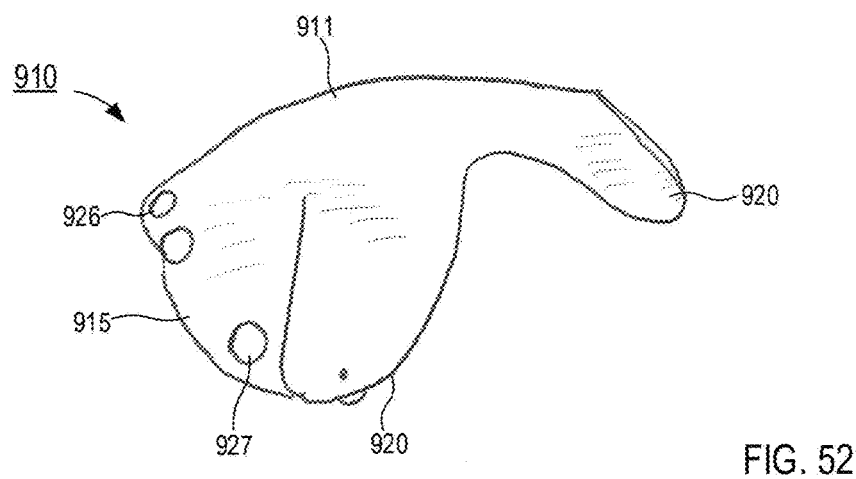
Figure 53:
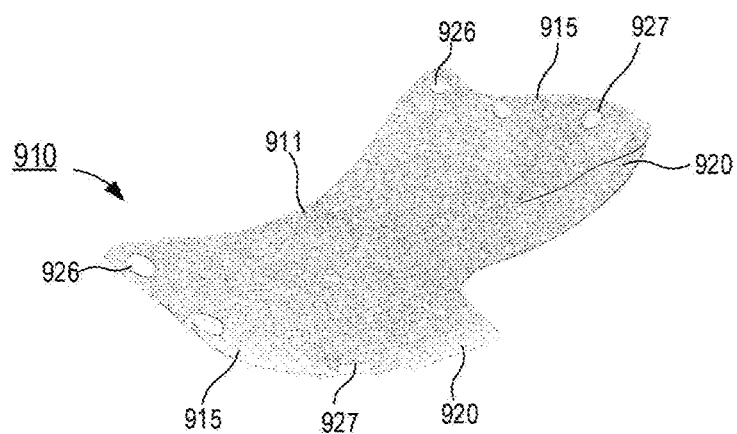

As shown in FIGS. 51-53, the frame 910 includes a top portion 911, side portions 915, and inferior portions 920. The frame 910 includes and/or forms a pair of convex and/or conical lobes with an apex that is substantially aligned with the globes of the eyes, when the therapeutic device 900 is coupled to the head of the user. In addition, the frame 910 is broadly convex in both a horizontal and a vertical axis. Similarly stated, in addition to the convex form of the lobes, the frame 910 can have a broad convex shape that extends across the full width and height of the eye region covered. As such, the convex form of the frame 910 can reduce direct rearward pressure exerted by the frame 910 on the therapeutic member 905, and hence the globes of the eyes. For example, in some embodiments, the frame 910 can distribute the rearward force on or to peripheral areas of the therapeutic member 905, which in turn, can transmit a rearward force on, for example, the orbital rim, rather than upon the globes of the eyes. In some embodiments, the convex and/or conical lobes diffuse the direct rearward pressure onto a relatively broad area of the orbital rim. In some embodiments, the convex and/or conical lobes diffuse and/or otherwise distribute the direct rearward pressure onto an area of the face of the user that is beyond or outside of the orbital rim. In this manner, the frame 910 can, for example, sandwich, clamp, pin, hold, or otherwise maintain a portion of the therapeutic member 905 between a peripheral portion of the frame 910 and a portion of the face outside of the orbital rim. Moreover, the arrangement of the frame 910 can be such that the rearward force is substantially non-orthogonal to the orbital rim. Similarly stated, the rearward force can be exerted at an angle other than 90° relative to an anterior surface of the orbital rim. In this manner, the rearward force exerted by the therapeutic device 900 on the ocular region can be reduced by, for example, including the frame 910 that forms one or more convex portions, rather than selectively forming the frame with one or more regions of greater flexibility, as described above.

Figure 54:
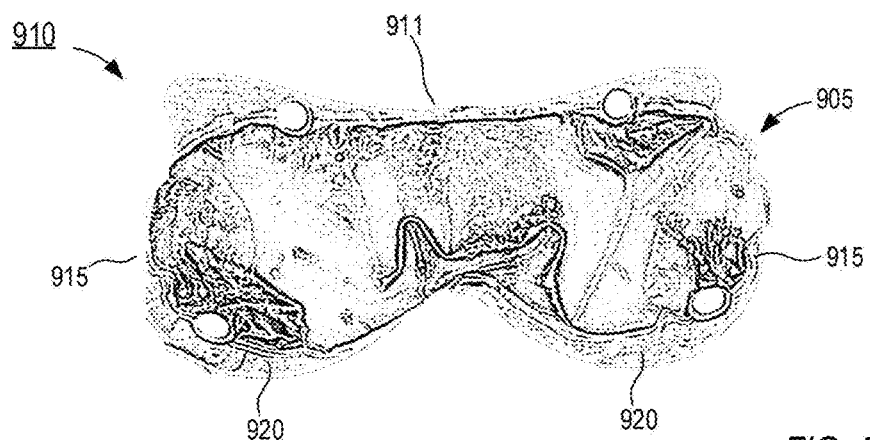
FIG. 54 is a rear perspective view of the flexible frame of FIGS. 51-53 coupled to a therapeutic member.
Figure 55:
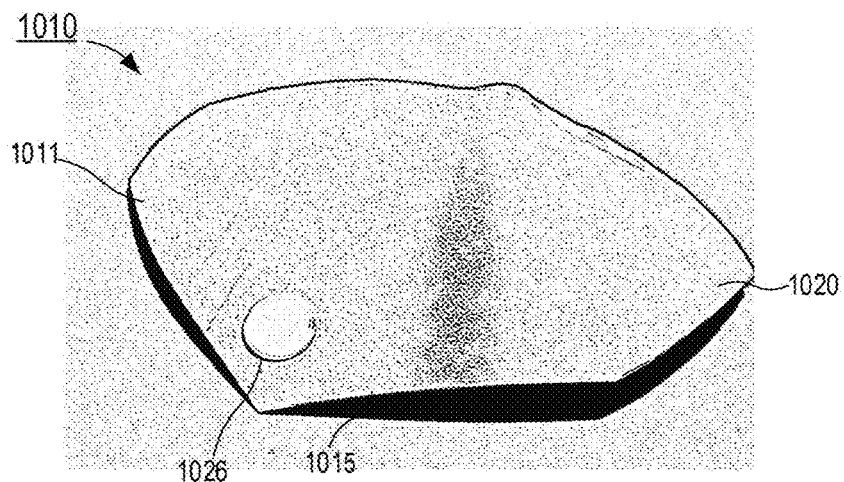
FIGS. 55 and 56 are a front perspective view and a rear perspective view, respectively, of a flexible frame included in a therapeutic device according to another embodiment.
Figure 56:
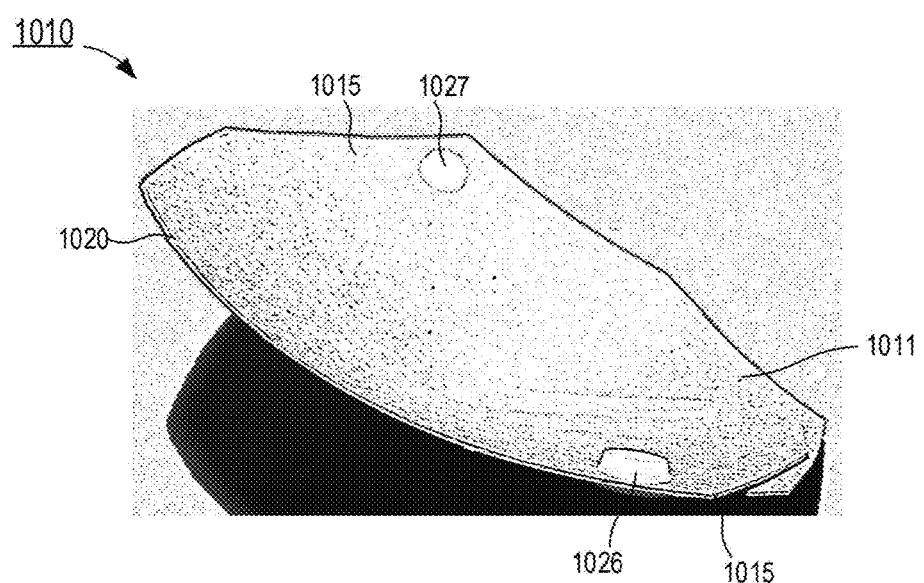
Figure 57:
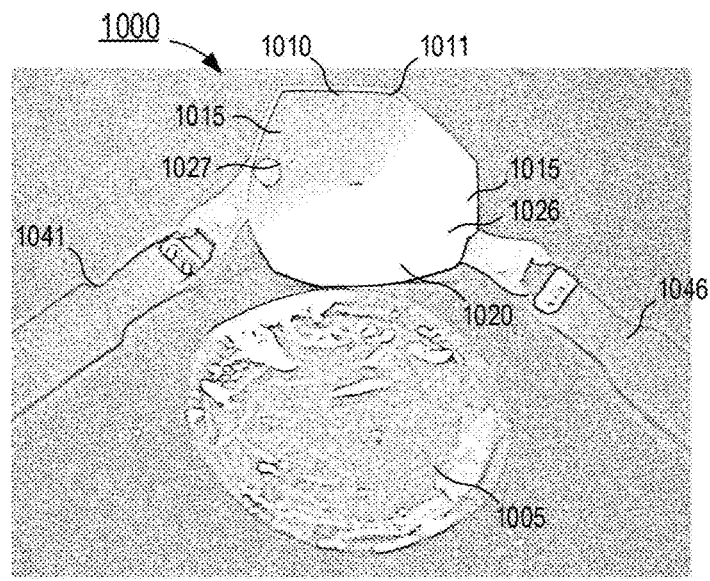
FIG. 57 is a rear view of the therapeutic device including the flexible frame of FIGS. 55 and 56 and a therapeutic member.

As shown in FIGS. 52 and 53, the frame 910 can include a first set of attachment points 926 and a second set of attachment points 927. As described above with reference to the frame 310, the first set of attachment points 926 and the second set of attachment points 927 can be coupled to, for example, a first strap and a second strap included in the coupling portion 940. Moreover, as shown in FIG. 54, the therapeutic member 905 can be configured to couple to a posterior surface of the frame 910 such that when the therapeutic device 900 is coupled to the head of the user, the therapeutic member 905 is placed in contact with the ocular region.

Although the frame 910 is shown and described above with reference to FIGS. 50-54 as including a set of two convex lobes, in other embodiments, a therapeutic device can include a frame with a single convex lobe. For example, FIGS. 55-58 illustrate a therapeutic device 1000 according to an embodiment. The therapeutic device 1000 can be used to place a therapeutic member 1005 (see e.g., FIGS. 57 and 58) in contact with a target region of the body of a user such as, for example, the ocular region of the face of the user. The therapeutic device 1000 includes a frame 1010 and a coupling portion 1040. The coupling portion 1040 can be substantially similar to the coupling portion 340 described above with reference to FIGS. 12-24. In this manner, the coupling portion 1040 can be coupled to the frame 1010 and can be transitioned from a first configuration to a second configuration to couple the therapeutic device 1000 to the head of the user (see e.g., FIG. 58), as described in detail above. Thus, the coupling portion 1040 is not described in further detail herein.

The frame 1010 includes a top portion 1011, side portions 1015, and an inferior portion 1020. The frame 1010 includes and/or forms a convex and/or conical lobe with an apex that is substantially aligned with the globe of an eye (e.g., the left or the right eye), when the therapeutic device 1000 is coupled to the head of the user. As such, the convex form of the frame 1010 can reduce direct rearward pressure exerted by the frame 1010 on the therapeutic member 1005, and hence the globe of the eye. For example, in some embodiments, the frame 1010 can distribute the rearward force on or to peripheral areas on the therapeutic member 1005, which in turn can transmit a rearward force on, for example, the orbital rim, rather than upon the globe of the eye. In some embodiments, the convex and/or conical lobe diffuses the direct rearward pressure onto a relatively broad area of the orbital rim. In some embodiments, the convex and/or conical lobe diffuses and/or otherwise distributes the direct rearward pressure onto an area of the face of the user that is beyond or outside of the orbital rim. In this manner, the frame 1010 can, for example, sandwich, clamp, pin, hold, or otherwise maintain a portion of the therapeutic member 1005 between a peripheral portion of the frame 1010 and a portion of the face outside of the orbital rim. Moreover, the arrangement of the frame 1010 can be such that the rearward force is substantially non-orthogonal to the orbital rim. Similarly stated, the rearward force can be exerted at an angle other than 90° relative to an anterior surface of the orbital rim.

Figure 58:
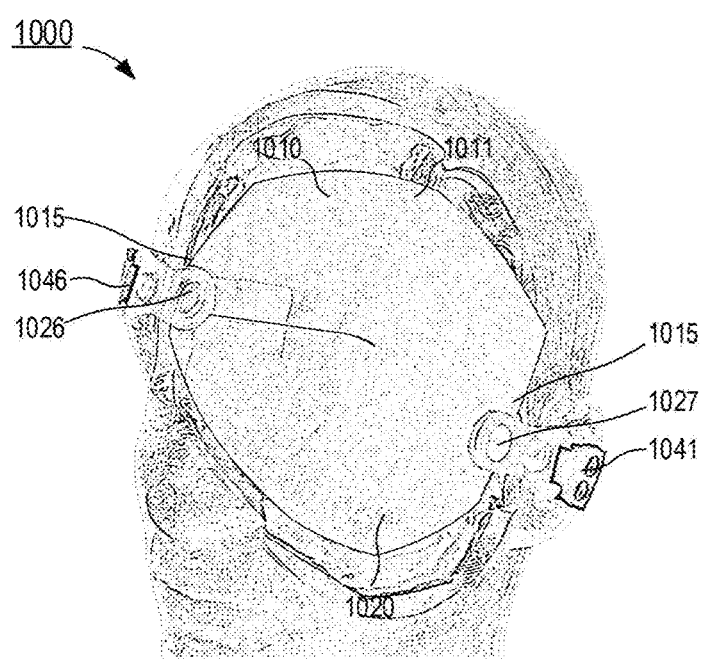
FIG. 58 is a perspective view of the therapeutic device of FIG. 57 coupled to a portion of the body.

As shown, the frame 1010 includes a first attachment point 1026 and a second attachment point 1027. The first attachment point 1026 and the second attachment point 1027 can be coupled to, for example, a first strap and a second strap included in the coupling portion 1040. Moreover, as shown in FIG. 58, the therapeutic member 1005 can be configured to couple to a posterior surface of the frame 1010 such that when the therapeutic device 1000 is coupled to the head of the user, the therapeutic member 1005 is placed in contact with the ocular region.

Figure 59:
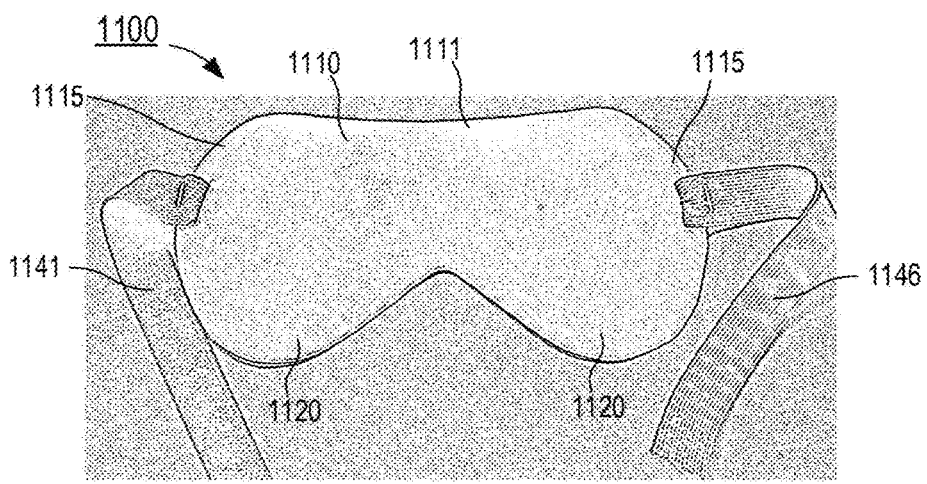
FIG. 59 is a rear view of a portion of a therapeutic device according to another embodiment.
Figure 60:
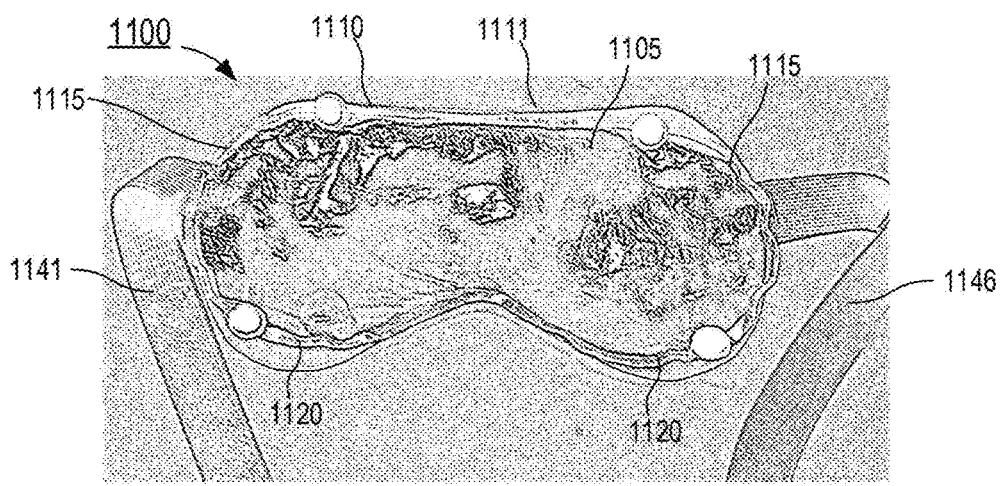
FIG. 60 is a rear view of the portion of the therapeutic device of FIG. 59 coupled to a therapeutic member.

Although the therapeutic devices 900 and 1000 include the frames 910 and 1010, respectively, that form one or more convex portions, in other embodiments, a therapeutic device can include a frame that is relatively planar prior to being coupled to the head of a user. For example, FIGS. 59 and 60 illustrate a therapeutic device 1100 according to an embodiment. The therapeutic device 1100 can be used to place a therapeutic member 1105 (FIG. 60) in contact with a target region of the body of a user such as, for example, the ocular region of the face of the user (not shown in FIGS. 59 and 60). The therapeutic device 1100 includes a frame 1110 and a coupling portion 1140. The coupling portion 1140 can be any suitable configuration. For example, in some embodiments, the coupling portion 1140 can be substantially similar to the coupling portion 340 described above with reference to FIGS. 12-24. In this manner, the coupling portion 1140 can be coupled to the frame 1110 and can be transitioned from a first configuration to a second configuration to couple the therapeutic device 1100 to the head of the user, as described in detail above. In other embodiments, the coupling portion 1140 can be any suitable arrangement.

As shown in FIG. 59, the frame 1110 includes a top portion 1111, side portions 1115, and inferior portions 1120. The frame 1110 can be formed from any suitable material that can be relatively flexible. For example, the frame 1110 can be formed from plastic, paper, rubber, silicone, foam, stiffened fabric, stiffened nonwoven material, wood, glass, and the like. In some embodiments, the frame 1110 can be made of a moderately resilient, shape-maintaining material or a relatively pliant or deformable material (e.g., under relatively low force such as when the therapeutic device 1100 is coupled to the head of the user). Moreover, the frame 1110 can have a shape that is associated with the ocular region of the user. As shown in FIG. 60, the therapeutic member 1105 can be coupled to a posterior surface of the frame 1110 such that when the therapeutic device 1100 is coupled to the head of the user, the therapeutic member 1105 is placed in contact with the ocular region of the user. Furthermore, by forming the frame 1110 from a relatively flexible material, the frame 1110 can bend, flex, and/or elastically deform such that a direct rearward pressure exerted by the frame 1110 on the therapeutic member 1105 is reduced and thus, a rearward force exerted on the globe of the eye is reduced.

Figure 61:
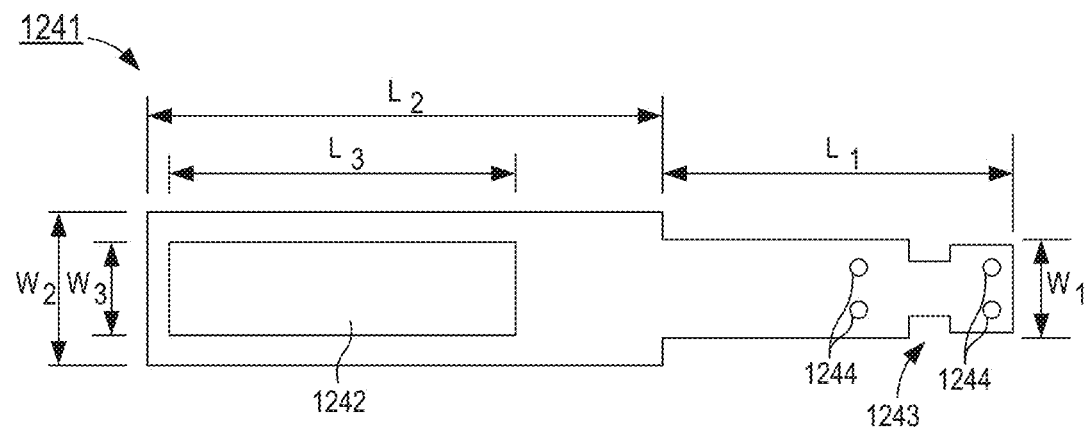
FIGS. 61 and 62 are schematic illustrations of a strap included in a coupling portion of a therapeutic device according to another embodiment.

Referring now to FIGS. 61-67, any of the therapeutic devices described above can include a coupling portion that can have any suitable arrangement. For example, FIG. 61 illustrates a strap 1241 that can be included in a coupling portion of a therapeutic device according to another embodiment. In some embodiments, the strap 1241 can be included in the coupling portion 340 of the therapeutic device 300. Portions of the strap 1241 can be substantially similar in form and function as the strap 341 shown, for example, in FIG. 13. For example, the strap 1241 includes a first coupling portion 1242 and a second coupling portion 1243. The first coupling portion 1242 can be configured to couple the strap 1241 to a second strap (not shown), as described above. For example, the first coupling portion 1242 can include a surface that defines a set of loop or a set of hooks configured to form a hook-and-loop coupling with the second strap. Moreover, the first coupling portion 1242 can have a length $L_3$ and a width $W_3$ that is substantially similar to the length $L_3$ and the width $W_3$ of the first strap 341 (see e.g., FIG. 14). The second coupling portion 1243 includes a set of openings 1244 that can receive a portion of a closure member, as described above with reference to the coupling portion 340.

The strap 1241 can have a size and shape that is similar to the first strap 341. For example, as described above, the strap 1241 can include a first portion having the first width $W_1$ the first length $L_1$, and a second portion having the second width $W_2$, and the second length $L_2$. The strap 1241 can differ from the first strap 341, however, by including substantially non-rounded corners. In some embodiments, the arrangement of the strap 1241 can, for example, increase manufacturing efficiency, increase ergonomics, and/or can provide a desired aesthetic profile.

Figure 62:
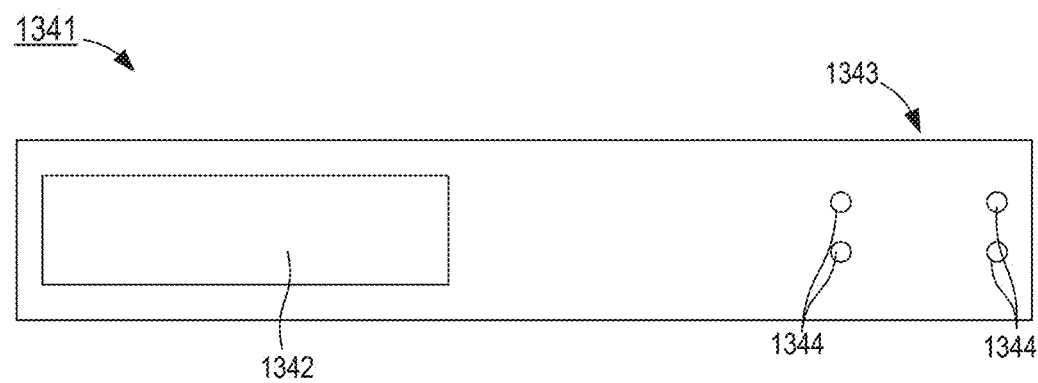

While the straps 341 and 1241 are shown and described as including portions of different widths, in some embodiments, a coupling portion can include one or more straps with a substantially constant width. For example, FIG. 62 illustrates a strap according to another embodiment. The strap 1341 includes a first coupling portion 1342 and a second coupling portion 1343. The first coupling portion 1342 can be substantially similar to the first coupling portion 342 of the first strap 341. In this manner, the first coupling portion 1342 can be coupled to a second strap (not shown) to, for example, couple a therapeutic device to the head of a user. The second coupling portion 1343 can include a set of openings 1344 that can receive a closure member or the like, as described above with reference to the second coupling portion 343 of the first strap 341. In this manner, the second coupling portion 1343 can be operable in coupling the strap 1341 to a frame of a therapeutic device. Although shown as including the openings 1344 in other embodiments, the second coupling portion 1343 can be configured without openings 1344, and/or can be coupled to a frame in any suitable manner (e.g., sewn in place, adhered, sonic welded, and/or the like). In some embodiments, forming the strap 1341 with a substantially constant width can, for example, increase manufacturing efficiency, decrease cost, decrease material usage, and/or the like.

Figure 63:
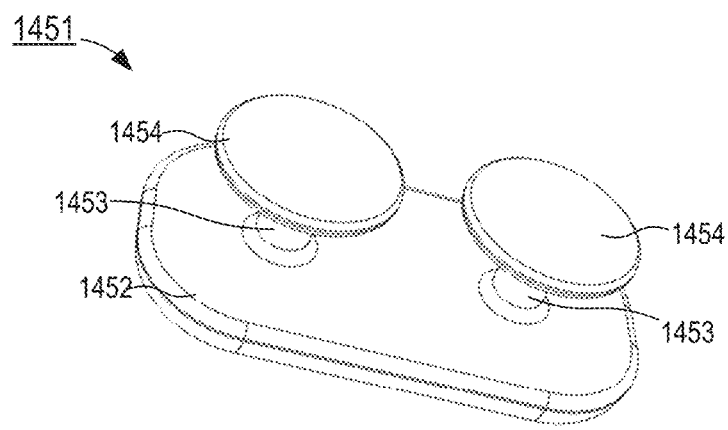
FIG. 63 is a perspective view of a closure member included in a coupling portion of a therapeutic device according to another embodiment.

FIG. 63 illustrates a closure member 1451 according to another embodiment. The closure member 1451 includes a base 1452 and a set of protrusions 1453. The protrusions 1453 each includes a flanged or flared end portion 1454. As described above, the closure member 1451 can be used to, for example, couple a strap to a coupling member and/or the frame. In some embodiments, the closure member 1451 can be substantially similar to the closure member 351. In some instances, the base 1452 can be rounded and/or otherwise shaped such as to increase the ergonomics of the closure member 1351 and/or to provide an aesthetic profile. Thus, the protrusions 1453 can be inserted into a set of openings defined by a coupling portion of a strap and can be arranged such that the flanged or flared ends 1454 and the base 1451 engage opposite surfaces to at least temporarily maintain the coupling portion in contact with a coupling member and/or a frame, as described above with reference to the closure member 351 of FIG. 16.

Figure 64:
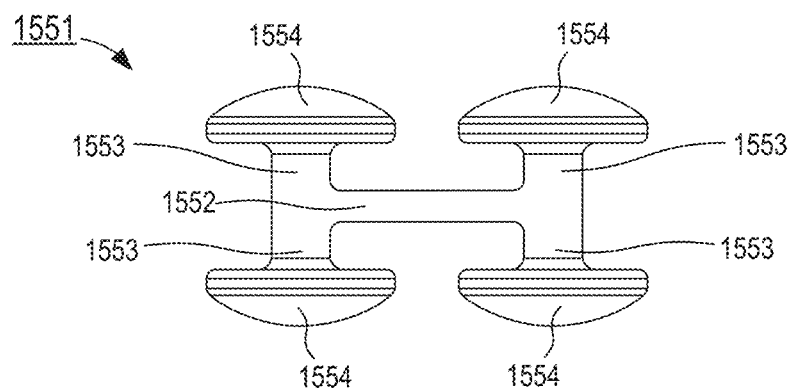
FIG. 64 is a side view of a closure member included in a coupling portion of a therapeutic device according to another embodiment.

Although the closure member 1451 is shown in FIG. 63 as having the protrusions 1453 extend from one side of the base 1452, in other embodiments, a closure member can include a set of protrusions that extend from two, opposite sides of a base. For example, FIG. 64 illustrates a closure member 1551 according to another embodiment. The closure member 1551 includes a base 1552 and a set of protrusions 1553 that extend from opposite sides of the base 1552. The protrusions 1553 each includes a flanged or flared end portion 1554, as described above with reference to the closure member 351. In use, the protrusions 1553 can be inserted into a set of openings defined by a coupling portion of a strap to maintain a coupling therebetween. More specifically, the closure member 1551 can be disposed between a first side and a second side of a coupling portion of a strap. For example, a strap can be inserted into a slot defined by a coupling member and/or a frame (not shown in FIG. 64) and an end portion can be folded back onto itself. As such, the closure member 1551 can be disposed between the two sides of the strap and the protrusions 1553 on a first side of the base 1552 can be inserted into a set of openings defined by a first side of the strap, while the protrusions 1553 on a second, opposite side of the base 1552 can be inserted into a set of openings defined by a second side of the strap. Thus, the base 1552 and the flanged or flared ends 1554 can engage the strap to maintain the coupling between the strap and the coupling member and/or frame. Furthermore, although shown as a single unit, in other embodiments, a closure member can comprise multiple independent units. Thus, for example, the closure member 1551 could be divided into two discrete units (not shown), each unit having two protrusions facing in opposite directions, and each protrusion terminating in a flanged or flared end portion 1554. In some such embodiments, a closure member need not include a base portion or the like. The use of such multiple closure units would be similar to the use of the single closure member 1551 described above.

Figure 65:
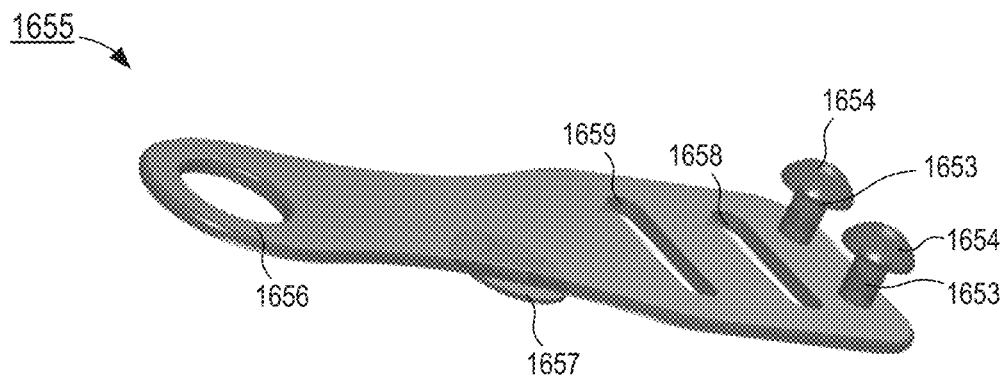
FIG. 65 is a perspective view of a closure member included in a coupling portion of a therapeutic device according to another embodiment.
Figure 66:
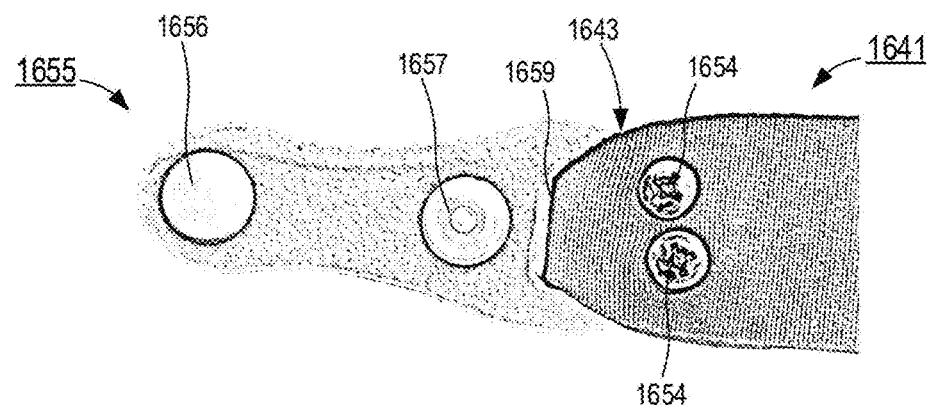
FIGS. 66 and 67 are a back view and a front view, respectively, of a portion of a strap coupled to the coupling member of FIG. 65.
Figure 67:
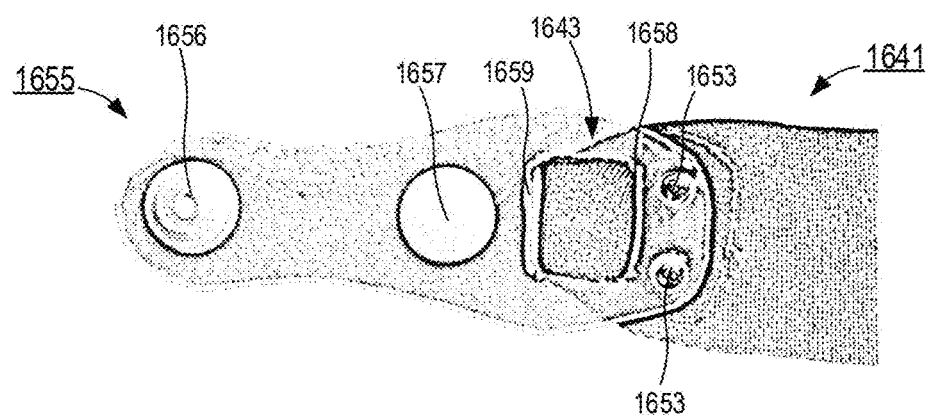

Although the closure member 351 and the coupling member 355 are shown and described above as being formed independently (i.e., two separate components), in other embodiments, a closure member and a coupling member can be unitarily formed (i.e., monolithically formed and/or forming a single component). For example, FIGS. 65-67 illustrate a coupling member 1655 that integrally includes a set of protrusions 1653 similar to the protrusions 353 included in the closure member 351 described above. As shown in FIG. 65, the coupling member 1655 also includes a first attachment portion 1656 and a second attachment portion 1657, and defines a first slot 1658 and a second slot 1659. The first attachment portion 1656 can be coupled to a first attachment point on a frame, as described above. The second attachment portion 1567 can be coupled to an inferior member such as those described above.

In use, a coupling portion 1643 of a strap 1641 (e.g., substantially similar to the second coupling portion 343 of the first strap 341 described above) can be inserted into the first slot 1658 and the protrusions 1653 can be inserted into a first set of openings (not shown in FIGS. 66 and 67)

defined by the strap 1641. As shown in FIGS. 66 and 67, the coupling portion 1643 of the strap 1641 can be threaded through the first slot 1658 and the second slot 1659 in such a manner as to allow the protrusions 1653 to be inserted into a second set of openings defined by the strap 1641 (FIG. 66). Thus, the strap 1641 can be coupled to the coupling member 1655 to be operably coupled to a frame.

Figure 68:
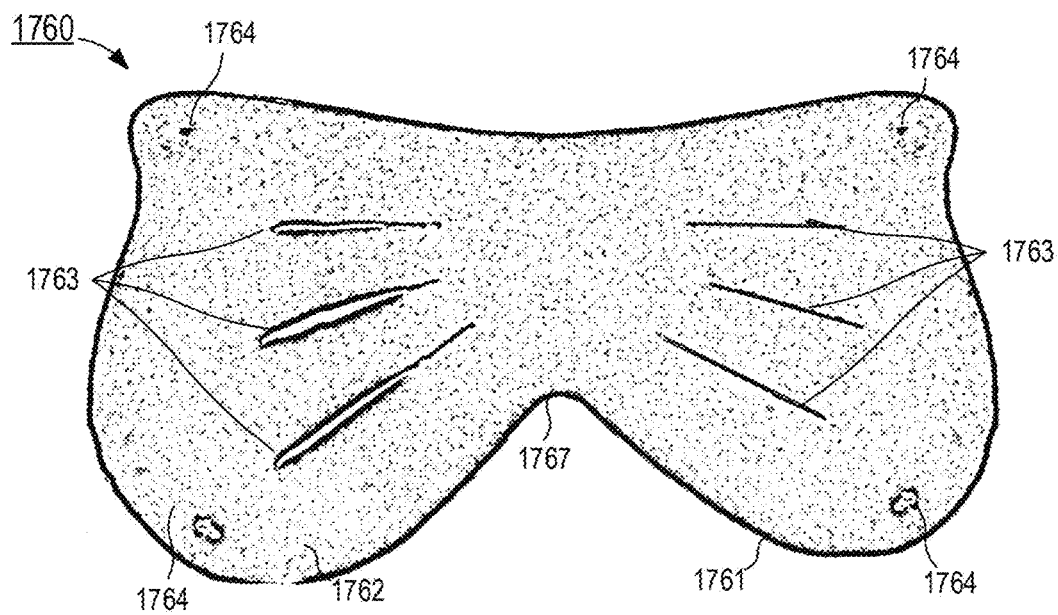
FIG. 68 is a front view of a first insulating member included in a therapeutic device according to another embodiment.

Referring now to FIGS. 68-90 any of the therapeutic devices described above can include an insulating portion and/or insulating member that can have any suitable arrangement. For example, FIG. 68 illustrates a first insulating member 1760 according to another embodiment. The first insulating member 1760 can be similar in function to the first insulating member 360 described above with reference to FIGS. 23-32. For example, the first insulating member 1760 can have a shape and size that is associated with a flexible frame such as the flexible frame 310 described above. Moreover, the first insulating member 1760 defines a set of openings 1764 that can each receive a post that extends from an anterior surface of a frame to at least temporarily couple the first insulating member 1760 to the frame, as described above. The first insulating member 1760 includes a first lobe 1761 and a second lobe 1772 that are separated and/or at least partially defined by a nasal region 1767. The arrangement of the first insulating member 1760 is such that when a therapeutic device is coupled to the head of a user, the first lobe 1761 and the second lobe 1762 are at least partially aligned with the ocular region of the user (e.g., disposed in an anterior position relative to the ocular region).

The first insulating member 1760 can differ from the first insulating member 360, however, in the arrangement of a set of slits 1763. More specifically, the insulating portion 1760 defines a set of slits 1763 along a portion of the first lobe 1761 and a portion of the second lobe 1762. The slits 1763 can be configured to increase the flexibility of at least a portion of the first insulating member 1760. In this manner, a portion of the first insulating member 1760 can be configured to elastically deform, bend, flex, etc. when exposed to an external force. For example, in some embodiments, the first insulating member 1760 can be coupled to a frame (e.g., the frame 310) of a therapeutic device and the therapeutic device can be coupled to the head of a user. As described above, in some instances, an anterior surface of a therapeutic member can be configured to extend through a set of apertures defined by the frame and as a result, can contact a posterior surface of the first insulating member 1760 and exert a force that is sufficient to deform a portion of the first insulating member 1760. In this manner, the slits 1763 can increase the flexibility of at least a portion of the first insulating member 1760, thereby allowing the first insulating member 1760 to flex when exposed to the force exerted by the therapeutic member. Thus, a force exerted in an opposite direction (e.g., a reaction force) on the ocular region of the user can be reduced.

Figure 69:
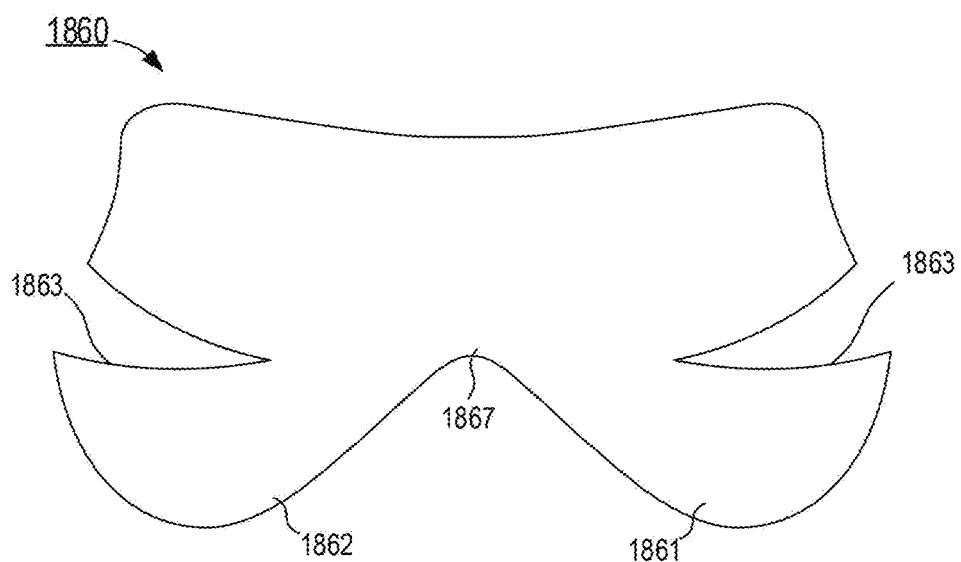
FIG. 69 is a front view of a first insulating member included in a therapeutic device according to another embodiment, in a first configuration.
Figure 70:
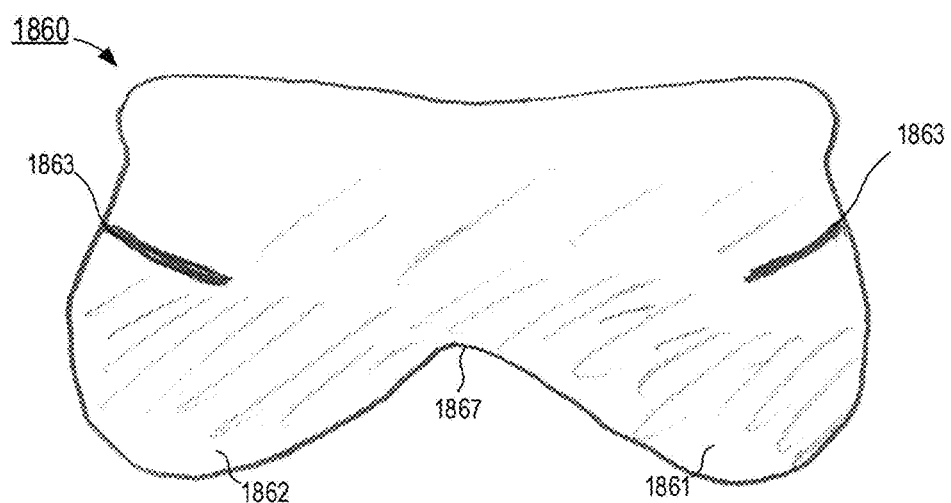
FIGS. 70 and 71 are a front view and a bottom view, respectively, of the first insulating member of FIG. 69 in a second configuration.
Figure 71:
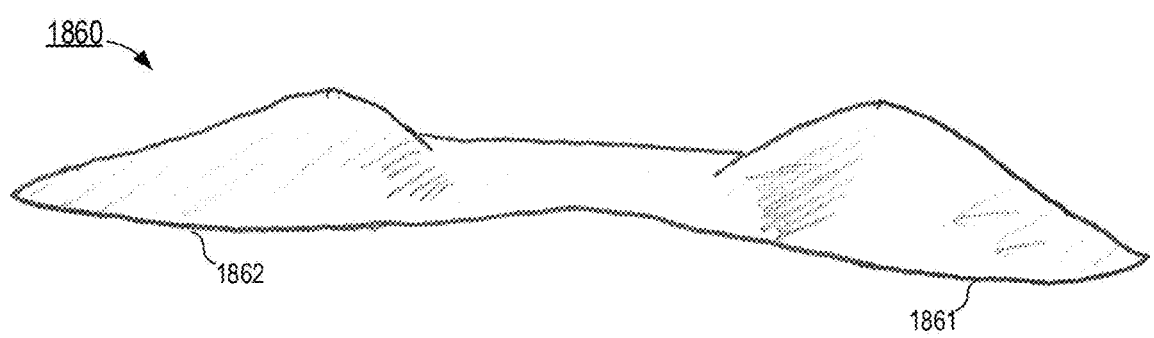

FIGS. 69-71 illustrate a first insulating member 1860 according to another embodiment. The first insulating member 1860 can be similar in function to the first insulating member 360 described above with reference to FIGS. 23-32. For example, the first insulating member 1860 can have a shape and size that is associated with a flexible frame such as those described herein. Moreover, the first insulating member 1860 can be at least temporarily coupled to a flexible frame as described above. The first insulating member 1860 includes a first lobe 1861 and a second lobe 1672 that are separated and/or at least partially defined by a nasal region 1867. The arrangement of the first insulating member 1860 is such that when a therapeutic device is coupled to the head of a user, the first lobe 1861 and the second lobe 1862 are at least partially aligned with the ocular region of the user (e.g., disposed in an anterior position relative to the ocular region).

The first insulating member 1860 can differ from the first insulating member 360, however, in the arrangement of a set of slits 1863. More specifically, the slits 1863 of the first insulating member 1860 can be arranged in a substantially lateral orientation relative to the first insulating member 1860. As shown in FIGS. 70 and 71, the first insulating member 1860 can be transitioned from a first, substantially planar configuration to a second non-planar configuration. In some embodiments, the first insulating member 1860 can be transitioned to the second configuration in a substantially similar manner as described above with reference to the first insulating member 360. Thus, the first insulating member 1860 can be coupled to a flexible frame of a therapeutic device to provide, for example, thermal insulation in an anterior direction relative to the face of the user. Although the first insulating member 1860 is shown in FIGS. 70 and 71 as defining the slits 1863, in other embodiments, the first insulating member 1860 can have a configuration or shape without such slits.

While the first insulating member 360 was shown and described as being transitioned to a second configuration in which portions of the first insulating member 360 are overlapping (see e.g., FIGS. 29 and 30), in other embodiments, an insulating member can be transitioned to a second configuration in which portions of the insulating member do not overlap. For example, FIGS. 72-75 illustrate a first insulating member 1960 according to another embodiment. The first insulating member 1960 can be similar in function as the first insulating member 360 described above with reference to FIGS. 23-32. For example, the first insulating member 1960 can have a shape and size that is associated with a flexible frame and can define a set of openings 1964 that can each receive a post that extends from an anterior surface of a frame to at least temporarily couple the first insulating member 1960 thereto, as described above. The first insulating member 1960 includes a first lobe 1961 and a second lobe 1962 that are separated and/or at least partially defined by a nasal region 1967. The arrangement of the first insulating member 1960 is such that when a therapeutic device is coupled to the head of a user, the first lobe 1961 and the second lobe 1962 are at least partially aligned with the ocular region of the user (e.g., disposed in an anterior position relative to the ocular region).

Figure 72:
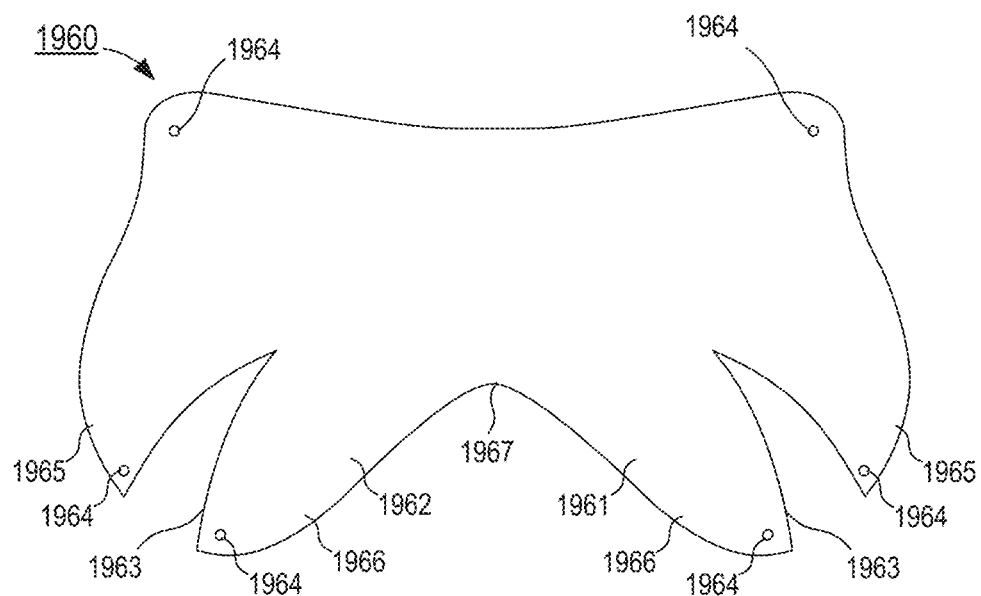
FIG. 72 is a front view of a first insulating member included in a therapeutic device according to another embodiment, in a first configuration.
Figure 73:
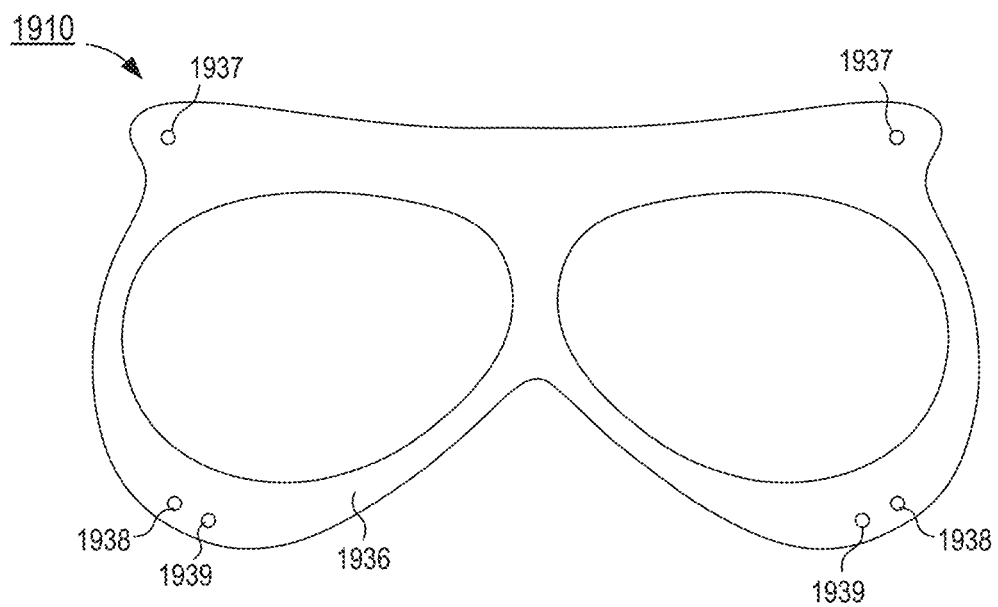
FIG. 73 is a front view of a flexible frame include the therapeutic device according to another embodiment.
Figure 74:
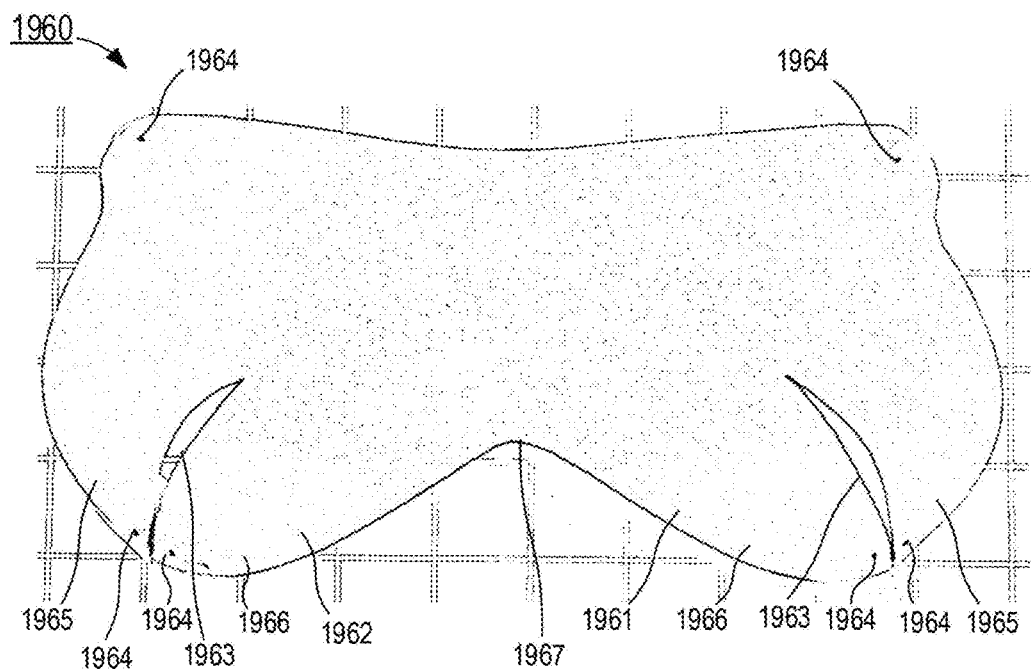
FIGS. 74 and 75 are a front view and a bottom view, respectively, of the first insulating member of FIG. 72 in a second configuration coupled to the flexible frame of FIG. 73.
Figure 75:
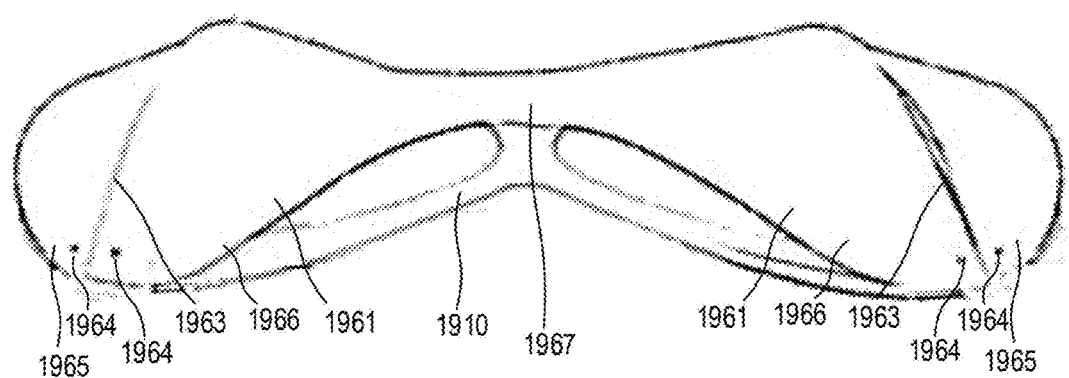

As shown in FIG. 72, the first insulating member 1960 defines a pair of slits 1963 that extend in a substantially inferior direction toward a peripheral edge of the first insulating member 1960. The first lobe 1961 and the second lobe 1962 each include a first leaflet 1965 and a second leaflet 1966 disposed on opposite sides of the slits 1963. As described above, the first insulating member 1960 can be transitioned from a first configuration to a second configuration to be coupled to a flexible frame. More specifically, FIG. 73 illustrates a flexible frame 1910 according to an embodiment. The flexible frame 1910 can be substantially similar to or the same as the flexible frame 410 described above with reference to FIG. 45. In this manner, the flexible frame 1910 includes an anterior surface 1936 from which a first set of posts 1937, a second set of posts 1938, and a third set of posts 1939 extend. The first set of posts 1937 can be substantially similar in form and function as the first set of posts 337 included in the flexible frame 310. The arrangement of the second set of posts 1938 and the third set of posts 1939, however, can differ in form and function from the second set of posts 338 of the flexible frame 310. For example, while the second set of posts 338 of the flexible frame 310 are configured to be inserted into the opening 364 defined by the first leaflet 365 and the opening 364 defined by the second leaflet 366 (see e.g., FIGS. 29-30), the second set of posts 1938 can be inserted into the opening 1964 defined by the first leaflets 1965 and the third set of posts 1939 can be inserted into the opening 1964 defined by the second leaflets 1966, as shown in FIGS. 74 and 75. Such an arrangement can, for example, reduce and/or eliminate an overlapping portion of the first leaflets 1965 and the second leaflets 1966. In some embodiments, the reduction and/or elimination of the overlapping portion can result in, for example, an increase in flexibility of at least a portion of the first insulating member 1960, which in turn, can reduce rearward pressure against the therapeutic member, and hence against the eyes of the user.

Figure 76:
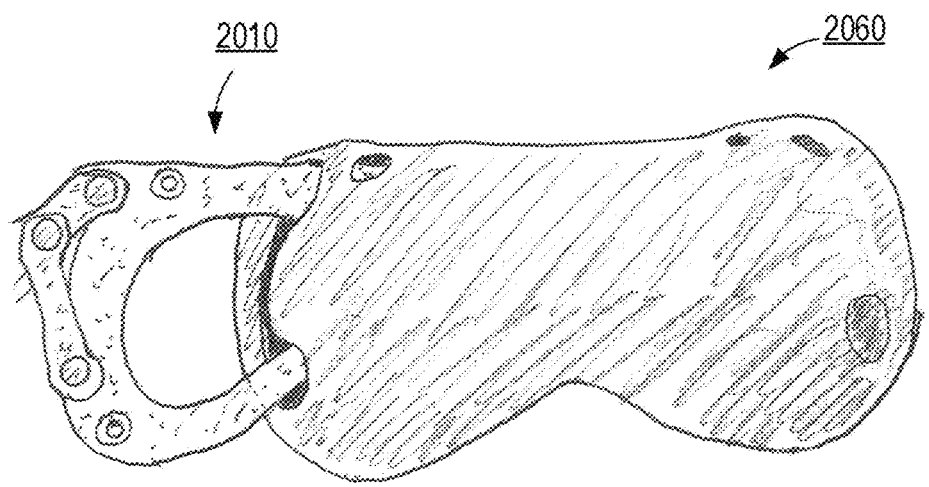
FIGS. 76 and 77 are rear views of a first insulating member included in a therapeutic device according to another embodiment.
Figure 77:
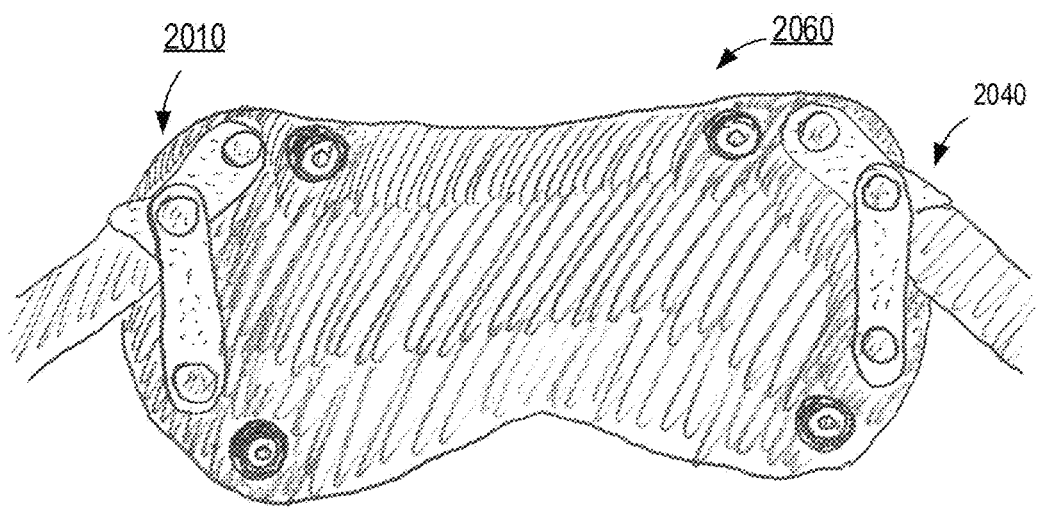

Although the first insulating members 360, 1760, 1860, and 1960 are shown and described as being coupled to an anterior surface of a flexible frame, in other embodiments, a flexible frame can be disposed between two sides of an insulating member. For example, FIGS. 76 and 77 illustrate a first insulating member 2060 configured to receive and/or surround a flexible frame 2010. More specifically, in some embodiments, the first insulating member 2060 can include a first side and a second side that are coupled together to collectively define an inner volume therebetween (i.e., the first side and second side form a pouch or the like). As such, the flexible frame 2010 can be inserted into the inner volume such that at least a portion of the flexible frame 2010 is surrounded by the first insulating member 2060. As shown in FIG. 77, the first insulating member 2060 can be arranged to allow a portion of the flexible frame 2010 and/or a coupling portion 2040 coupled to the flexible frame 2010 to extend through the first insulating member 2060. Similarly stated, when disposed in the inner volume of the first insulating member 2060, at least a portion of the flexible frame 2010 and/or the coupling portion 2040 is disposed outside of the inner volume, thereby allowing more versatile operation of the coupling portion 2040 as well as more efficient coupling of a therapeutic member (not shown in FIGS. 76 and 77) to the flexible frame 2010.

Figure 78:
FIGS. 78 and 79 are schematic illustrations of a second insulating member included in a therapeutic device each according to another embodiment.
Figure 79:
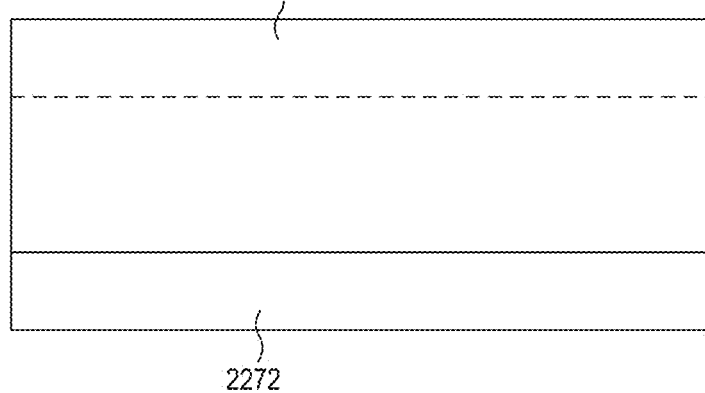
Figure 80:
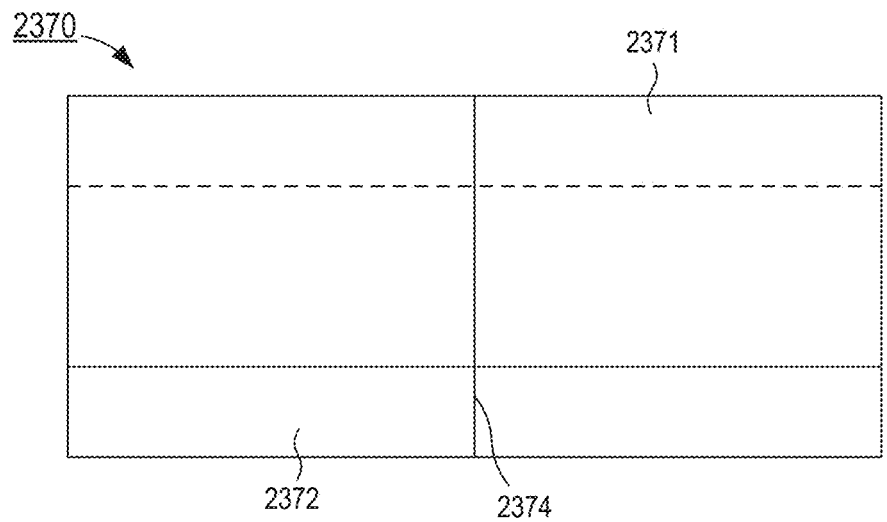
FIGS. 80 and 81 are front views of a second insulating member included in a therapeutic device in a first configuration and a second configuration, respectively, according to another embodiment.
Figure 81:
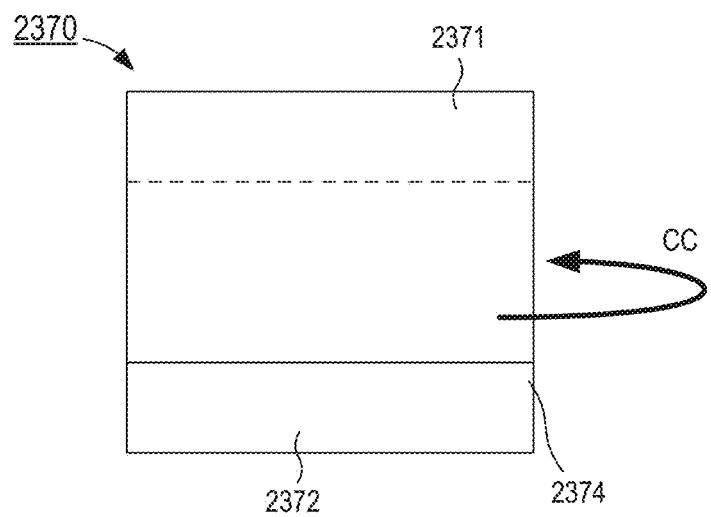

While the therapeutic device 300 is shown and described above as including the second insulating member 370 having the first folded region 371 and the second folded region 372 in a particular configuration, in other embodiments, a therapeutic device can include a second insulating member having any suitable shape, size, or configuration. For example, FIG. 78 illustrates a second insulating member 2170 according to another embodiment. As shown, the second insulating member 2170 is in a substantially planar configuration (e.g., does not include folded regions). Alternatively, as shown in FIG. 79, a second insulating member 2270 can include a first folded region 2271 and a second folded region 2272 that are disposed on opposite sides of the second insulating member 2270. Said another way, the first folded region 2271 is folded in a first direction to be disposed on a first side of the second insulating member 2270 and the second folded region 2272 is folded in a second direction, opposite the first direction, to be disposed on a second side, opposite the first side, of the second insulating member 2270.

In some embodiments, a second insulating member can be transitioned between a first configuration and a second configuration. For example, FIGS. 80-83 illustrate a second insulating member 2370 according to another embodiment. The second insulating member 2370 includes a first folded region 2371 and a second folded region 2372, as described above with reference to the second insulating member 2270. The second insulating member 2370 further includes a medial region 2374 about which the second insulating member 2370 can be folded to transition the second insulating member 2370 between a first configuration (FIG. 80) and a second configuration, as indicated by the arrow CC in FIG. 81. In some embodiments, the second insulating member 2370 can be folded substantially in half. In other embodiments, the second insulating member 2370 can be folded in an asymmetric manner.

Figure 82:
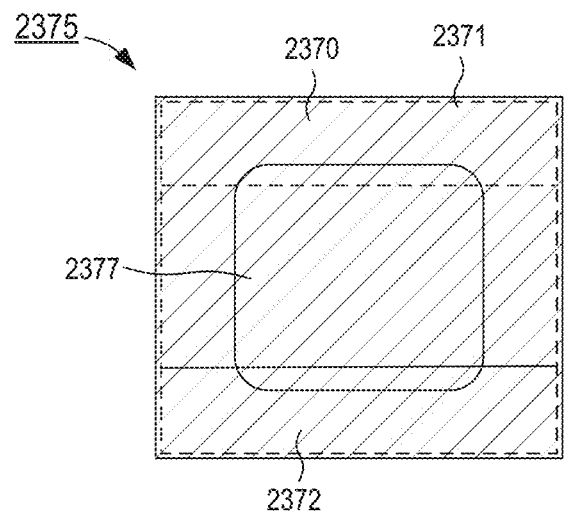
FIGS. 82 and 83 are top views of the second insulating member of FIGS. 80 and 81 disposed in a sealable package in a first configuration and a second configuration, respectively, according to another embodiment.
Figure 83:
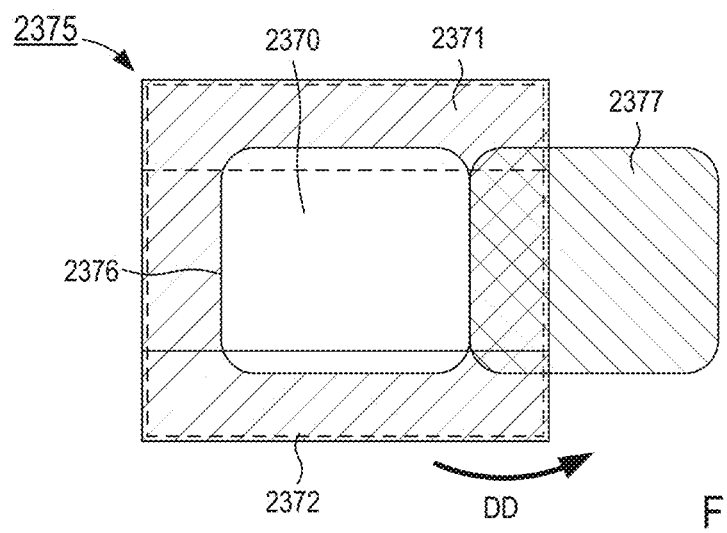

In some embodiments, the second configuration can be associated with, for example, a storage configuration or the like. For example, as shown in FIGS. 82 and 83, the second insulating member 2370 can be disposed in a sealable package 2375. The sealable package 2375 can define an inner volume that is configured to receive one or more second insulating members 2370 in the second configuration. The sealable package 2375 includes a seal member 2377 that is configured to selectively cover or seal an opening 2376 defined by the sealable package 2375, as described above. In some embodiments, the seal member 2377 can be configured to form a substantially fluid tight seal with a surface of the sealable package 2375 that can fluidically isolate the inner volume from a volume outside of the sealable package 2375. As such, the sealable package 2375 can be configured to, for example, maintain the second insulating members 2370 disposed therein with a desired moisture content (e.g., prevent evaporation of a fluid suspended in the second insulating members 2370). In use, a user can manipulate the sealable package 2375 by moving the seal member 2377 relative to the opening 2376, as indicated by the arrow DD in FIG. 83. In this manner, the user can access the second insulating members 2370 disposed therein and can, for example, remove the second insulating member 2370 disposed adjacent to the opening 2376 by engaging a pick point or the like. In some embodiments, an edge of the first folded region 2371 and/or the second folded region 2372 can form the pick point, as described above.

Figure 84:
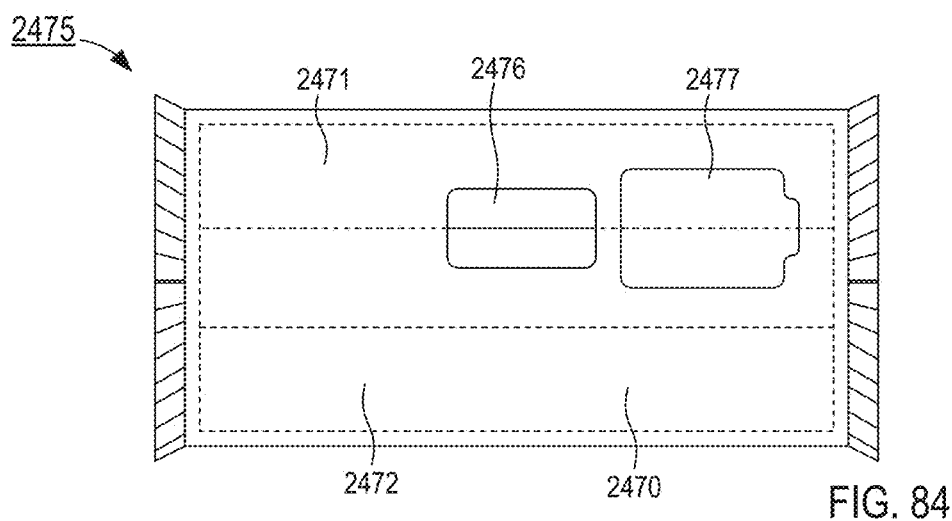
FIG. 84 is a top view of a package configured to house one or more second insulating members according to another embodiment.

Although the second insulating member 2370 is shown and described as being folded about a medial portion 2374 to be disposed in the sealable package 2375, in other embodiments, a sealable package can be configured to store one or more second insulating members 2370 that are not folded about a medial portion. For example, as shown in FIG. 84, a sealable packaging 2475 can be configured to store one or more insulating members 2470 which are not folded about a medial portion. The sealable packaging 2475 defines an opening 2476 and includes a seal member 2477 configured to be selectively positioned about the opening to isolate the second insulating members 2470 disposed therein. As shown, the opening 2476 can be substantially offset from the center of the sealable package 2475. In this manner, the first folded region 2471 or the second folded region 2472 can include an edge portion that can be, for example, a pick point that can allow a user to access and remove one of the second insulating members 2470 from the sealable package 2475. Although shown in FIG. 84 in a substantially open configuration, the seal member 2477 can be moved relative to the opening 2476 to substantially fluidically isolate an inner volume defined by the sealable package 2475 from a volume outside of the sealable package 2475. For example, in some embodiments, the seal member 3772477 can include an adhesive or the like that can form the substantially fluidic seal. In other embodiments, the seal member 2477 can engage a surface of the sealable package 2475 to form a friction or snap fit that can form the substantially fluidic seal. Thus, the second insulating members 2470 can be maintained in an environment having suitable moisture content, as described above.

Figure 85:
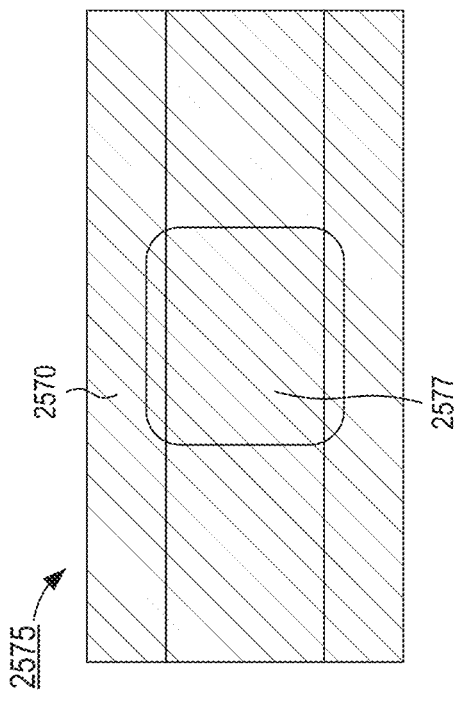
FIGS. 85 and 86 are top views of a package storing one or more second insulating members in a first configuration and a second configuration, respectively, according to another embodiment.
Figure 86:
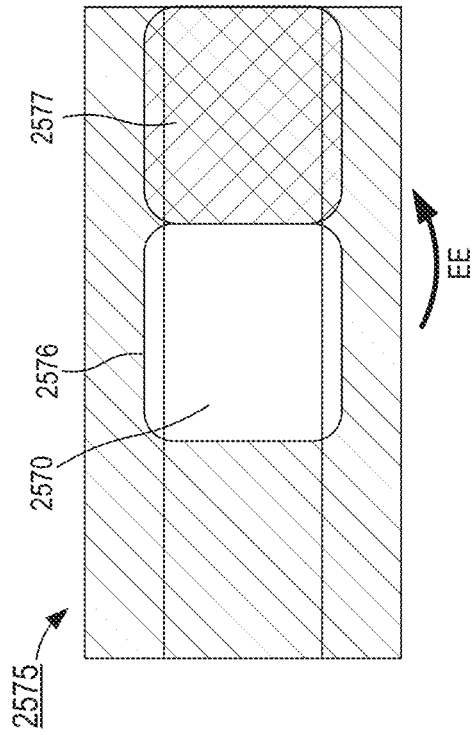

Although the sealable packaging 2475 is shown and described as defining the opening 2476 in a substantially offset position, in other embodiments, a sealable packaging can define an opening in any suitable position and/or arrangement. For example, FIGS. 85 and 86 illustrate a sealable package 2575 according to another embodiment. As shown, the sealable package 2575 can have a size that is associated with the size of a second insulating member 2570 disposed therein. As described above, the sealable package 2575 includes a seal member 2577 that selectively covers an opening 2576. In some embodiments, the size and/or configuration of the opening 2576 can be substantially similar to or the same as the size and/or configuration of the opening 376 defined by the package 375 described above with reference to FIG. 37. In this manner, a user can manipulate the sealable package 2575 by moving the seal member 2577 relative to the opening 2576, as indicated by the arrow EE in FIG. 86. Thus, the user can remove the second insulating member 2370 by engaging a pick point or the like formed by a folded region, as described above.

Figure 87:
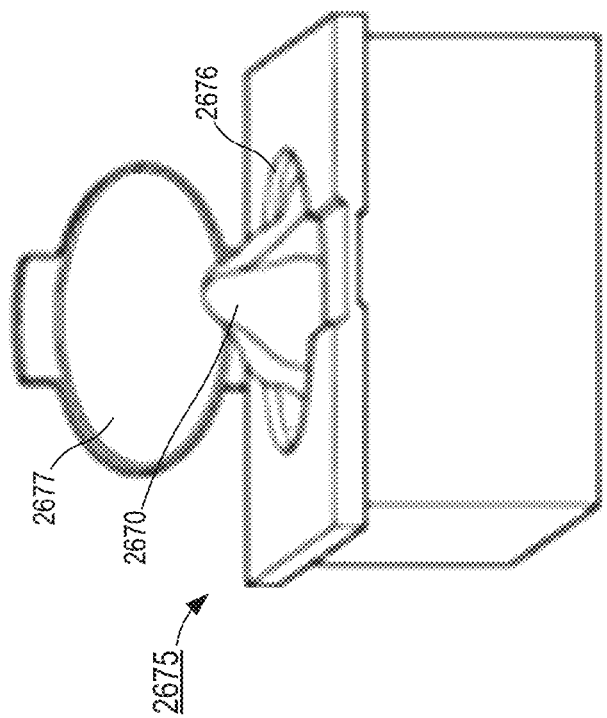
FIG. 87 is a perspective view of a package storing one or more second insulating members according to another embodiment.

Although the second insulating members 2370 and 2570 are described above as being removed from the sealable packages 2375 and 2575, respectively, by engaging a pick point defined by one or more folded regions, in other embodiments, any portion of a second insulating member can be used as a pick point. For example, FIG. 87 illustrates a second insulating member 2670 disposed in a sealable package 2675. As shown, sealable package 2675 includes a seal member 2677 configured to selectively cover an opening 2676. In this manner, a user can manipulate the sealable package 2675 by moving the seal member 2677 relative to the opening 2676 to gain access to the second insulating member 2670 disposed therein. In some embodiments, the user can remove the second insulating member 2670 by engaging a pick point formed, for example, by a medial portion of the second insulating member 2670 (i.e., a portion other than an edge of a folded region).

Figure 88:
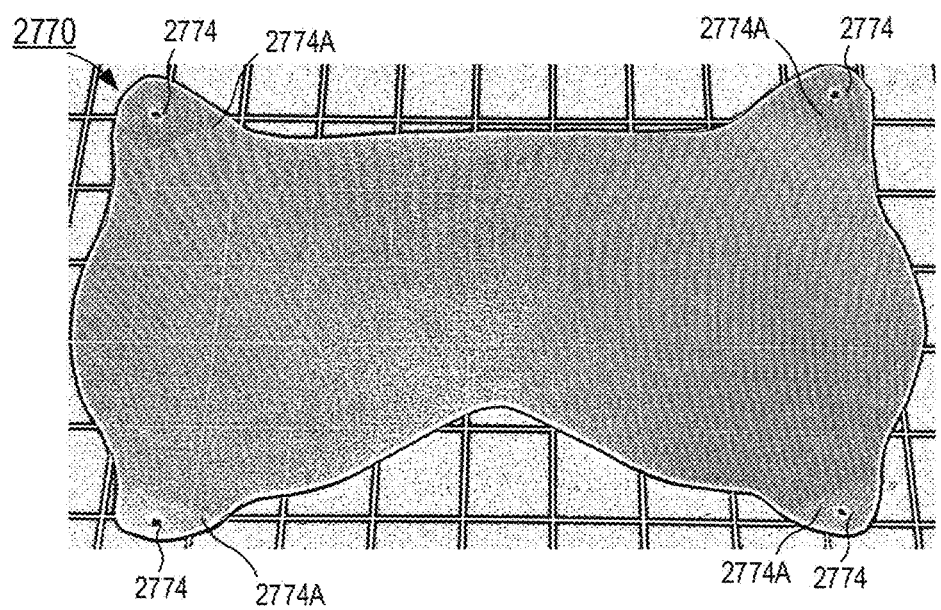
FIG. 88 is a front view of a second insulating member according to an embodiment.
Figure 89:
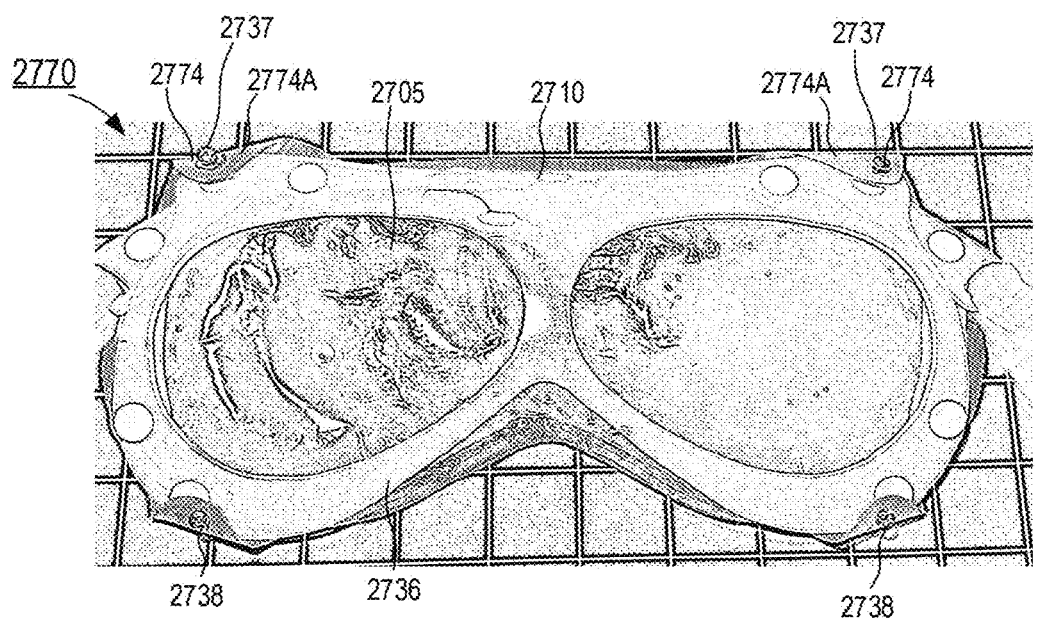
FIG. 89 is a front view of the second insulating member of FIG. 88 coupled to a flexible frame, according to an embodiment.

FIGS. 88 and 89 illustrate a second insulating member 2770 according to another embodiment. As described in detail below, the second insulating member 2770 is configured to be coupled to a posterior surface of a flexible frame 2710 and/or a therapeutic member 2705 (FIG. 89). More specifically, the flexible frame 2710 can be substantially similar to or the same as the flexible frame 310 described above. In this manner, an anterior surface 2736 of the flexible frame 2737 can include a set of posts 2737 that can be operable in coupling the second insulating member 2770 to the flexible frame 2710. For example, as shown in FIGS. 88 and 89, the second insulating member 2770 includes a set of coupling portions 2774A that each defines an opening 2774. As shown in FIG. 89, the coupling portions 2774A can be wrapped around the flexible frame 2710 when the second insulating member 2770 is disposed adjacent to the posterior surface of the therapeutic member 2705. In this manner, the posts 2737 can be inserted into the corresponding opening 2774 defined by the coupling portions 2774A to at least temporarily couple the second insulating member 2770 to the flexible frame 2710. In some embodiments, the posts 2737 can be substantially similar to, for example, posts 337 and 338 of flexible frame 310. As such, in some embodiments, a first insulating member such as the first insulating member 370 and the second insulating member 2770 can be coupled to posts 2737 and 2738.

Figure 90:
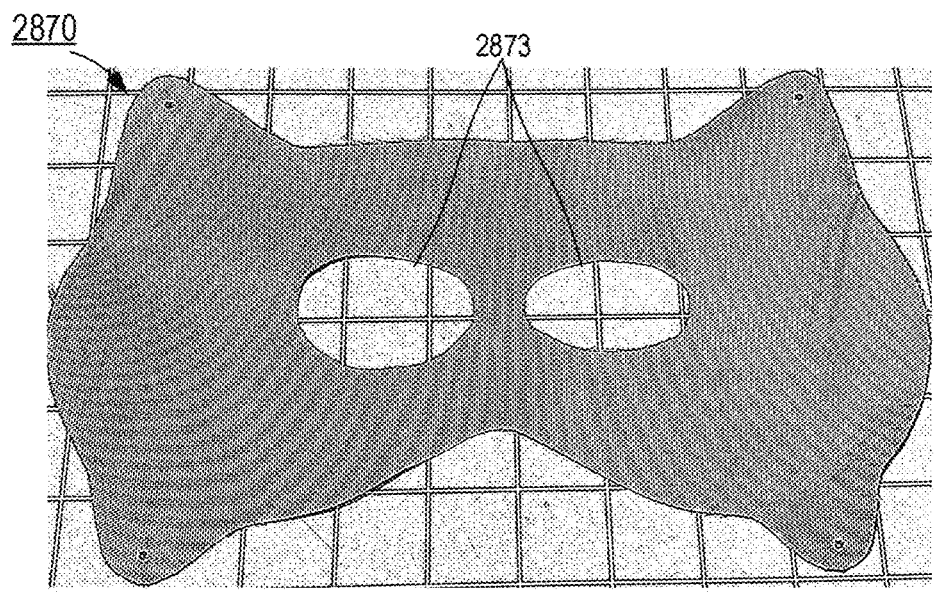
FIG. 90 is a front view of a second insulating member according to an embodiment.

In some embodiments, a second insulating member can be arranged so as not to cover, obscure, or conceal a patient's eyes, from an anterior anatomic perspective, when the second insulating member is positioned adjacent to the face of the user. For example, as shown in FIG. 90 a second insulating member 2870, which is otherwise similar to the second insulating member 2770, can define a set of apertures 2873. The arrangement of the second insulating member 2870 is such that the apertures 2873 are substantially aligned with, for example, the eyes of a user when the second insulating member 2870 is disposed adjacent to the face of the user. Thus, the user's eyes are unobstructed from an anterior anatomic perspective by the second insulating member 2870. Said another way, the apertures 2873 defined by the second insulating member 2870 can be such that an edge of the second insulating member 2870 defining each aperture 2873 circumscribes at least a portion of an eye of the user, from an anatomic perspective, when the second insulating member 2870 is disposed adjacent to the face of the user.

Figure 91:
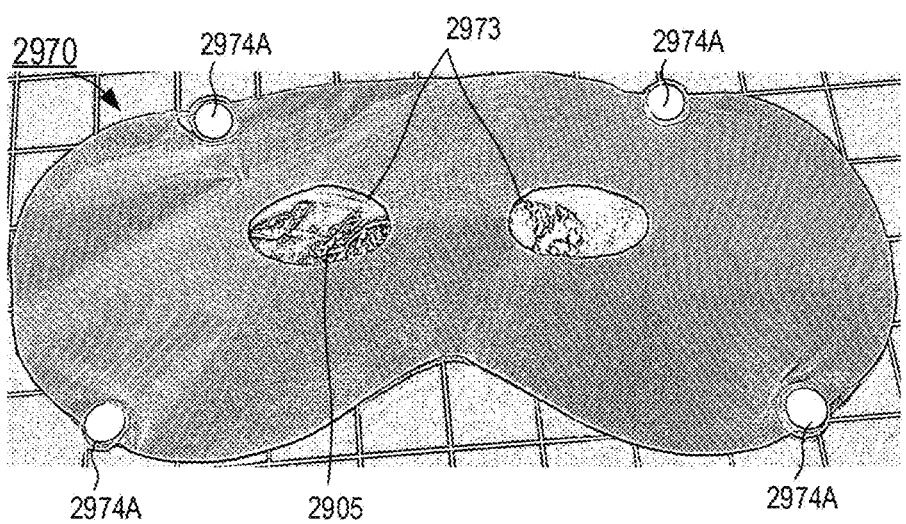
FIG. 91 is a rear view of a second insulating member coupled to a therapeutic member, according to an embodiment.

Although the coupling portions 2774A of the second insulating member 2770 are shown and described as wrapping around a portion of the flexible frame 2710 to be coupled to the anterior surface 2736, in other embodiments, a second insulating member 2770 can include any suitable coupling portion or mechanism. For example, FIG. 91 illustrates a second insulating member 2970 coupled to a therapeutic member 2905 according to another embodiment. The second insulating member 2970 can have a shape that is associated with and/or substantially corresponds to a shape of the therapeutic member 2905. As shown, the second insulating member 2905 includes a set of couplers 2974A that are configured to couple the second insulating member 2970 to the therapeutic member 2905. In some embodiments, the couplers 2974A can be, for example, snaps or the like that can form a snap fit with a corresponding portion of the therapeutic member 2905. In this manner, the second insulating member 2970 can be removably coupled to the therapeutic member 2905.

In other embodiments, the therapeutic member 2905 and the second insulating member 2970 can be fixedly coupled together via, for example, the couplers 2974A. For example, the couplers 2974A can be snaps that each include a snap cap and a male or female portion of a snap fixture. In this manner, a portion of therapeutic member 2905 and a portion of second insulating member 2970 can be disposed (e.g., sandwiched) between the snap cap and the male or female (stud or socket, respectively) portion of the snap fixture. Such a structure can be assembled using a snap press operation wherein a protruding portion of the snap cap passes through the portion of the second insulating member 2970, the portion of the therapeutic member 2905, and the stud or socket portion in order to secure the assembly in place. In some embodiments, such sandwiching allows the exposed male or female portions (which appear on the side of the therapeutic member which is not covered by the second insulating member 2970) to be coupled to a corresponding female or male snap fixture on flexible frame 2710 (as described above with reference to the therapeutic member 305 and the flexible frame 310). Thus, the second insulating member 2970 can be at least temporarily retained in a fixed position relative to the therapeutic member 2905. Moreover, the second insulating member 2970 can define a set of apertures 2973 that can be substantially aligned with the eyes of a user when the second insulating member 2970 is disposed adjacent to the face of the user, as described above.

In some instances, the arrangement of the second insulating members 2770, 2870, and 2970 can be such that, when coupled to the therapeutic a corresponding therapeutic device (as described above), a user can use the therapeutic devices without manually affixing a different second insulating member to the therapeutic device prior to use (e.g., after an initial coupling associated with, for example, a first use). The second insulating members 2770, 2870, and/or 2970, either by themselves or coupled to a therapeutic member, can be provided to and used by a user who, for example, already owns and/or already has access to a flexible frame, without the need for purchasing an additional corresponding flexible frame. That is to say, the second insulating members 2770, 2870, and/or 2970 can be manufactured, shipped, purchased, and/or obtained independently of the flexible frame and/or other portions of a therapeutic device.

While referred to herein as the second insulating members 370, 2170, 2270, 2370, 2770, 2870, and 297 are specifically described herein, in other embodiments, the second insulating members and/or portions thereof can serve different functions. In addition, in some embodiments, a moist sheet structure such as, for example, the secondary insulating member 370 can be disposed on the rear surface (facing the user) of, for example, the second insulating member 2870. In some instances, the second insulating member 370 can be disposed between a second insulating member such as, for example, the second insulating member 2870 and a therapeutic member such as, for example, the therapeutic member 305, 2705 and/or 2905. In such instances, a relatively moist heat can be applied, for example, specifically to the periocular region (e.g., via the apertures 2873), while avoiding the application of moisture to areas surrounding the periocular region. While the secondary insulating members 2870 and 2970 are each shown in FIGS. 90 and 91, as having two apertures 2873 and 2973, respectively, that correspond to a first and a second eye of a user, in other embodiments, a second insulating member can have a single aperture corresponding to a single eye of a user. As a particular example, such a second insulating member can be so configured even when the secondary insulating member is configured to span over both a first and a second eye of a user. In such embodiments, the second insulating member having a single aperture can be used, for example, when treating a primarily or entirely unilateral eye condition, such as an acute chalazion, hordeolum, or the like. In some embodiments, a second insulating member such as for example 2870 could be configured to be used alternatively for either a left eye or a right eye, thus reducing inconvenience and cost for the user.

Figure 92:
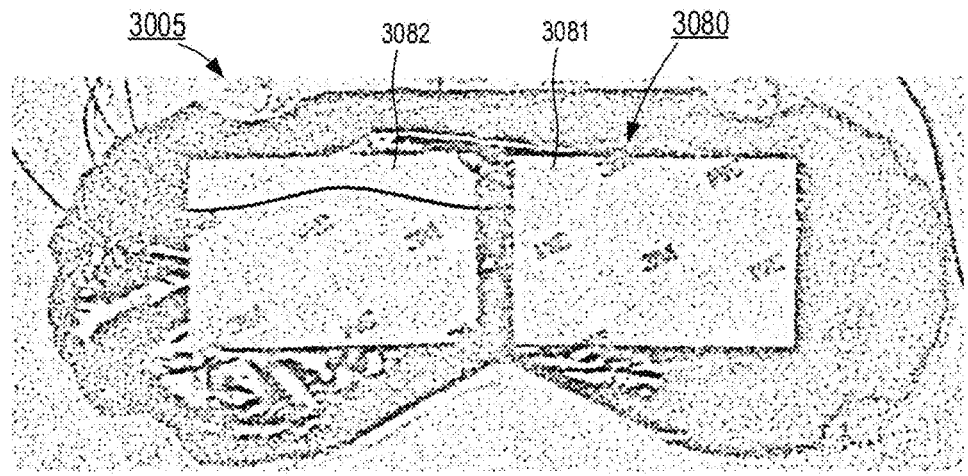
FIG. 92 is a front view of a heating member coupled to a therapeutic member according to an embodiment.

Any of the therapeutic devices and/or components thereof can be used with any suitable device, mechanism, system, circuit, and/or the like that is configured to transfer energy to a therapeutic member included therein. For example, while the therapeutic device 300 is shown and described as being placed in a microwave to increase the energy potential of the therapeutic member 305 (e.g., increase a temperature of a thermal gel or the like include therein), the therapeutic member 305 can receive energy from any suitable source. By way of example, FIG. 92 illustrates a heating mechanism 3080 in contact with a therapeutic member 3050 according to an embodiment. A heating mechanism can have any number of components. As shown, for example, the heating mechanism 3080 includes a first heating member 3081 and a second heating member 3082. Each heating member 3081 and 3082 can be electrically coupled to a current source (e.g., a battery, wall outlet, and/or other electrical source). In this manner, the first heating member 3081 and the second heating member 3082 can receive a flow of current that can be operable in increasing a temperature of at least a portion of the heating members 3081 and 3082. The arrangement of the heating mechanism 3080 is such that the first heating member 3081 and the second heating member 3082 can each independently heat a portion of the therapeutic member 3005. Similarly stated, the first heating member 3081 and the second heating member 3082 transfer thermal energy to independent and/or targeted portions of the therapeutic member 3005. In some embodiments, the portions of the therapeutic member 3005 can substantially correspond to, for example, portions of the ocular region of a user. Moreover, with the therapeutic member 3005 defining a single inner volume (as described above), the therapeutic member 3005 can diffuse and/or distribute the thermal energy to areas and/or portions having a lower thermal energy. Thus, thermal energy can be transferred to the therapeutic member 3005 which, in turn, can transfer the thermal energy to, for example, the ocular region of the user. In some embodiments, the heating mechanism 3080 can be configured to remain in contact with the therapeutic member 3005 during a therapeutic treatment of a user. Therefore, the heating mechanism 3080 can supply thermal energy substantially continuously during the therapeutic treatment. In some embodiments, the heating mechanism 3080 can be manipulated to adjust the amount of thermal energy transferred to the therapeutic member 3005 (e.g., increase or decrease a temperature).

The heating members 3081 and 3082 can be activated according to similar or dissimilar mechanisms or algorithms, such that the thermal energy delivered by each heating member 3081 and 3082 at a given point can be equivalent or inequivalent. Similarly, the target or "set-point" temperature for each heating element 3081 and 3082 can be equivalent or inequivalent at any given point in time. As such, the heating mechanism 3080 can be used, for example, to deliver a different thermal application to each eye region of a user. In some embodiments, the heating members 3081 and 3082 can be, for example, flexible heaters, such as flexible polyimide heating elements and/or the like. The heating members 3081 and 3082 can be coupled to an outer surface of the therapeutic member 3005 that faces away from the eye region of a user when therapeutic member 3005 is positioned against the eye region of the user (i.e., positioned on a surface of the therapeutic member 3005 that is substantially opposite the surface in contact with the eye region).

The heating mechanism 3080 can have any suitable surface area formed from, for example, the sum of the surface areas of the heating members 3081 and 3082. For example, in some embodiments, the heating members 3081 and 3082 can each have a surface area of, for example, about 3.5 sq. in., 4.0 sq. in., 4.5 sq. in., 5.0 sq. in., 5.5 sq. in., 6.0 sq. in., 6.5 sq. in., 7.0 sq. in., 7.5 sq. in., 8.0 sq. in., 8.5 sq. in., 9.0 sq. in., or any surface area or fraction of a surface area therebetween. In other embodiments, the heating members 3081 and 3082 can each have a surface area less 3.5 sq. in. or greater than 9.0 sq. in. Moreover, the heating members 3081 and 3082 can have substantially equivalent or inequivalent surface areas.

In some embodiments, the surface area of the heating mechanism 3080 (i.e., the sum of the surface areas of the heating members 3081 and 3082) can be based at least partially on a surface area of a side (i.e., surface) of the therapeutic member 3005 that is placed in contact with the user. For example, in some embodiments, the surface area of heating mechanism 3080 can be a percentage of the surface area of the side such as, for example, about 10%, about 20%, about 30%, about 35%, about 40%, about 50%, or any percent or fraction of a percent therebetween. In other embodiments, the surface area of the heating mechanism 3080 can be less than about 10% of the surface area of the side or greater than about 50% of the surface area of the surface of the therapeutic member 3005. In one embodiment, the surface area of heating mechanism 3080 can be about 35% of the surface area of the side of therapeutic member 3005.

In some instances, the surface area of the heating mechanism 3080 can be at least partially based on, for example, a surface area-to-volume ratio, where the volume is a volume of the contents of therapeutic member 3005 (in cubic centimeters (cc)). For example, in some embodiments, the surface area-to-volume ratio can be about 0.05 sq. in. per cc, about 0.10 sq. in. per cc, about 0.15 sq. in. per cc, about 0.175 sq. in. per cc, about 0.180 sq. in. per cc, about 0.185 sq. in. per cc, about 0.190 sq. in. per cc, about 0.195 sq. in. per cc, about 0.200 sq. in. per cc, or about 0.250 sq. in. per cc, or any ratio or fraction of a ratio therebetween. In other embodiments, the surface area-to-volume ratio can be less than about 0.05 sq. in. per cc or greater than about 0.250 sq. in. per cc. In one embodiment, the surface area-to-volume ratio can be about 0.195 sq. in. per cc.

Similarly, the heating mechanism 3080 can be configured to have, for example, a wattage-to-volume ratio, wherein the wattage of heating mechanism 3080 can be the sum of the products of the wattage rating and the surface area of each heating element 3081 and 3082 and the volume is the volume of the therapeutic member 3005. For example, in some embodiments, the wattage-to-volume ratio of heating mechanism 3080 can be about 0.1 watt per cc, about 0.2 watt per cc, about 0.25 watt per cc, about 0.3 watt per cc, about 0.35 watt per cc, about 0.4 watt per cc, about 0.45 watt per cc, about 0.5 watts per cc, or any ratio or fraction of a ratio therebetween. In other embodiments, the wattage-to-volume ratio can be less than about 0.1 watt per cc or greater than about 0.5 watt per cc. In one embodiment, the wattage-to-volume ratio can be about 0.3 watts per cc.

While the heating mechanism 3080 is shown in FIG. 92 as being applied to therapeutic member 3005 without the presence of a surrounding enclosure, in other embodiments, a heating mechanism can be activated while a therapeutic member is enclosed in a surrounding enclosure such as, for example, an insulated container. In such embodiments, disposing a therapeutic member (e.g., the therapeutic member 3005) in an insulated container can, for example, limit and/or minimize convective or conductive heat loss, which can improve heating efficiency and/or reduce a time of heating. In some instances, once a desired amount of thermal energy has been transferred to the therapeutic member 3005, therapeutic member 3005 can be removed from the container and applied to the eye region of a user (as described above). In some instances, the heating mechanism 3080 can continue to supply thermal energy to the therapeutic member 3005 during use (e.g., after the therapeutic member 3005 is removed from the insulated container and applied to the eye region of the user to, for example, substantially maintain a desired temperature.

Figure 93:
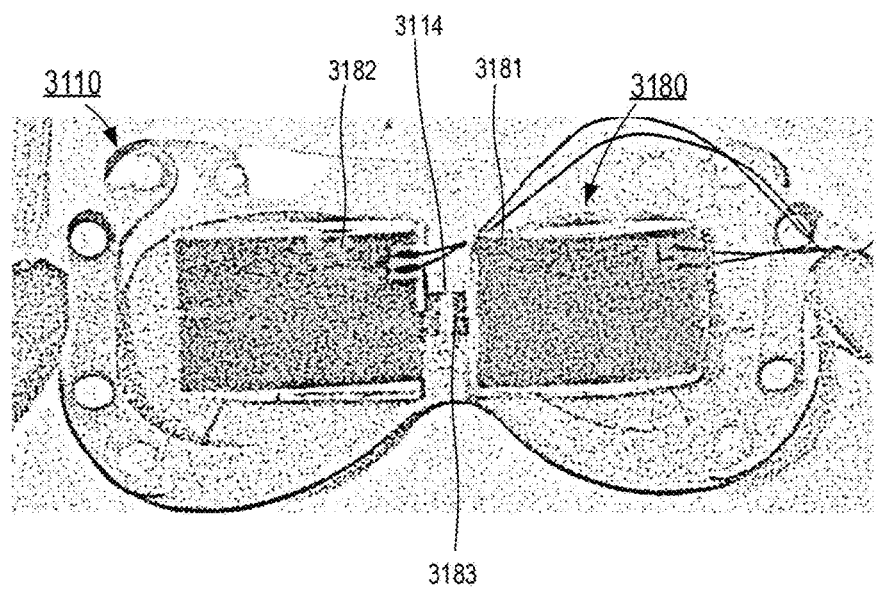
FIG. 93 is a rear view of a heating member coupled to a therapeutic device according to another embodiment.

While the heating mechanism is shown in FIG. 92 as being directly coupled to the therapeutic member, in other embodiments, a heating mechanism can be coupled to a flexible frame of a therapeutic device. For example, FIG. 93 illustrates a heating mechanism 3180 that is coupled to a flexible frame 3110 according to another embodiment. The heating mechanism 3180 includes a first heating member 3181 and a second heating member 3182 that can be substantially similar to the first heating member 3081 and the second heating member 3082 described above. Furthermore, the heating mechanism 3180 includes a coupling portion 3183 that can engage a coupling portion 3114 of the flexible frame 3110. The arrangement of the coupling portions 3114 and 3183 can be such that the first heating member 3181 and the second heating member 3182 are at least temporarily maintained in contact with a therapeutic member (not shown in FIG. 93) coupled to the flexible frame 3110. Thus, thermal energy can be transferred to the therapeutic member, as described above.

Figure 94:
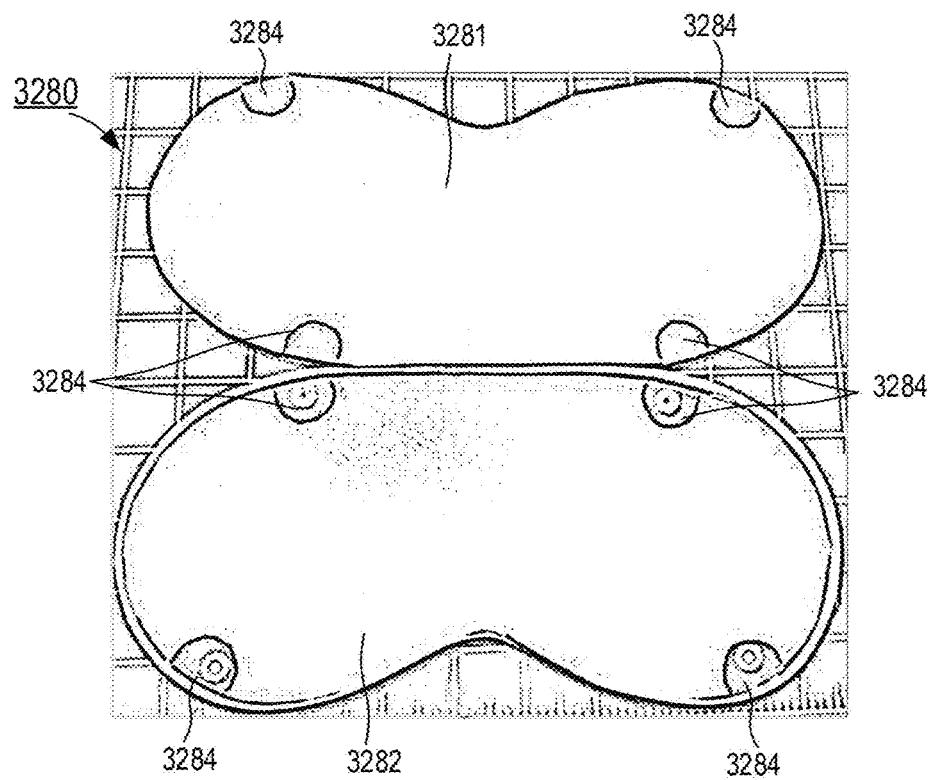
FIG. 94 is a front view of a heating device according to an embodiment.
Figure 95:
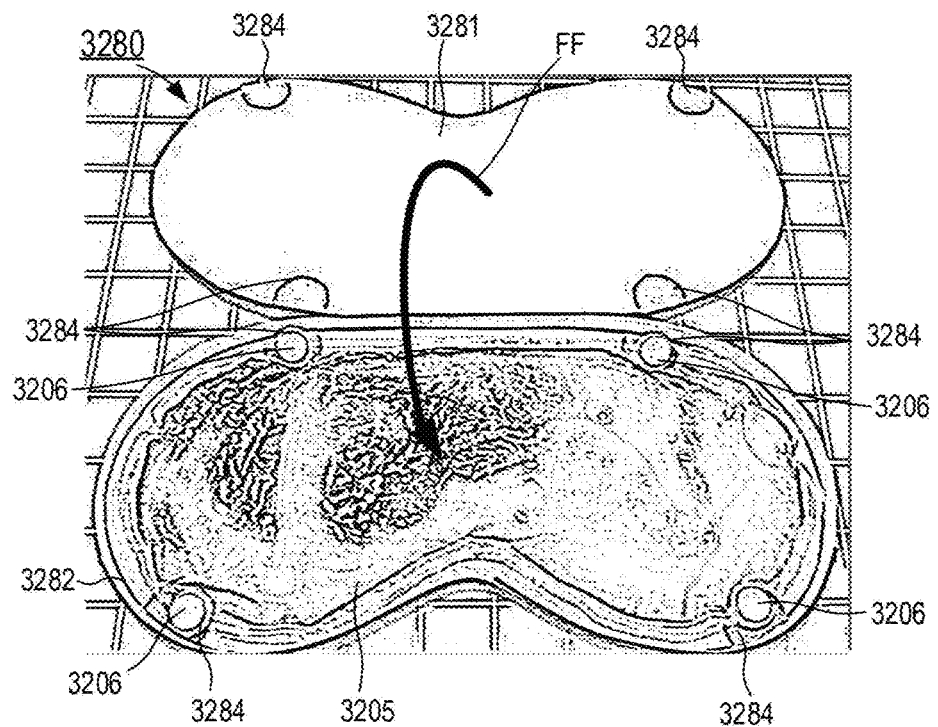
FIG. 95 is a front view of a therapeutic member disposed in the heating device of FIG. 94.

Although the first heating members 3081 and 3181 and the second heating members 3082 and 3182 are shown as being disposed on the same side of a therapeutic device, in other embodiments, a heating mechanism can be configured to substantially surround a therapeutic member. For example, FIGS. 94 and 95 illustrate a heating mechanism 3280 according to an embodiment. The heating mechanism 3280 includes a first heating member 3281 and a second heating member 3282 that can be moved relative to one another to define an inner volume configured to receive a therapeutic member 3205. For example, a first surface of the therapeutic member 3205 can be placed in contact with the second heating member 3282 and the first heating mechanism 3281 can be moved relative to the second heating member 3282 to contact a second surface of the therapeutic member 3205, opposite the first surface, as indicated by the arrow FF in FIG. 95. In this manner, the heating mechanism 3280 can receive a flow of current that is operable in increasing a temperature of at least a portion of the heating members 3281 and 3282, and thus, the therapeutic member 3205 disposed therebetween. Moreover, as shown the first heating member 3281 and the second heating member 3282 can include a set of insulators 3284 that are configured to insulate a portion of the heating members 3281 and 3282, thereby reducing the amount of thermal energy transferred thereto. As shown in FIG. 95, in some embodiments, the heating mechanism 3280 can be arranged such that the insulators 3284 are substantially aligned with a set of couplers 3206 (e.g., similar to the couplers 306 of the therapeutic member 305) included in the therapeutic member 3205. Thus, the insulators 3284 can reduce the amount of thermal energy transferred to the couplers 3206 that can otherwise result in discomfort when in contact with the user. In some embodiments, insulators 3284 can be configured to matingly couple with couplers 3206 in order to, for example, form a more stable positioning of therapeutic member 3205 relative to the heating members 3281 and 3282.

In other embodiments, a heating mechanism configured to substantially surround a therapeutic member can have a single heating member, or can have heating members with substantially dissimilar heating profiles. For example, in some embodiments, the heating member 3281 can be an insulating member or a heating member with a low thermal energy output, whereas the heating member 3282 can be a heating member with, for example, a relatively large thermal energy output, such that heating of the therapeutic member 3005 is primarily or exclusively via the heating member 3282. In this manner, thermal energy can be transferred to the therapeutic member 3005 by the heating member 3282, while the thermocouple can determine and/or sense a temperature associated with the therapeutic member 3005. In some instances, the thermocouple can be configured to send a signal to the heating member 3282, for example, when a desired temperature or "set-point" has been reached and, upon receipt, the heating member 3283 can be configured to substantially stop the transfer of thermal energy to the therapeutic member 3005. In some instances, disposing the thermocouple on a side of the therapeutic member 3005 that is opposite a side in contact with the heating mechanism 3280 can ensure a heating throughout substantially the entire volume of the therapeutic member 3005.

Figure 96:
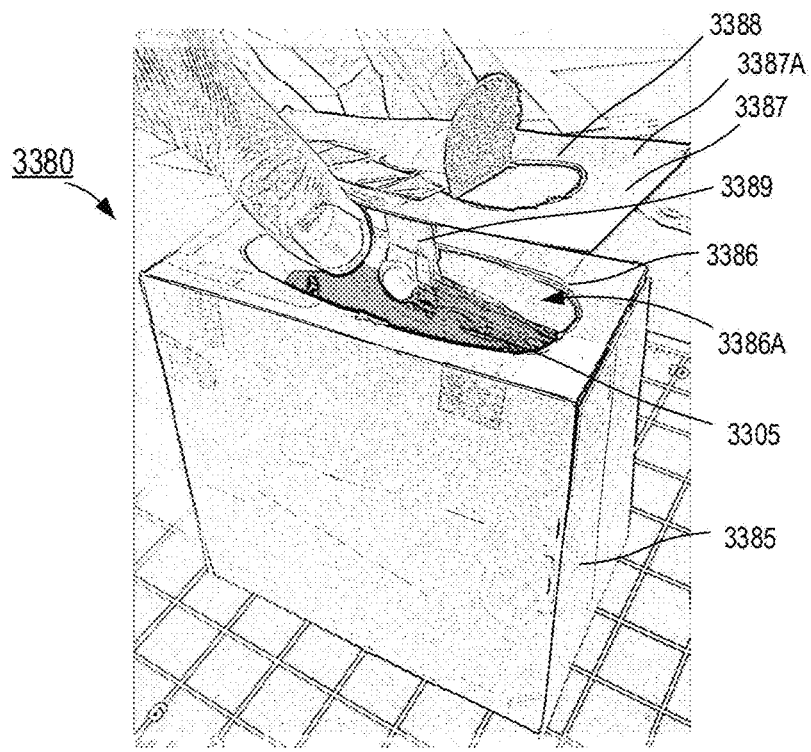
FIGS. 96-98 are perspective views of a heating device according to an embodiment.
Figure 97:
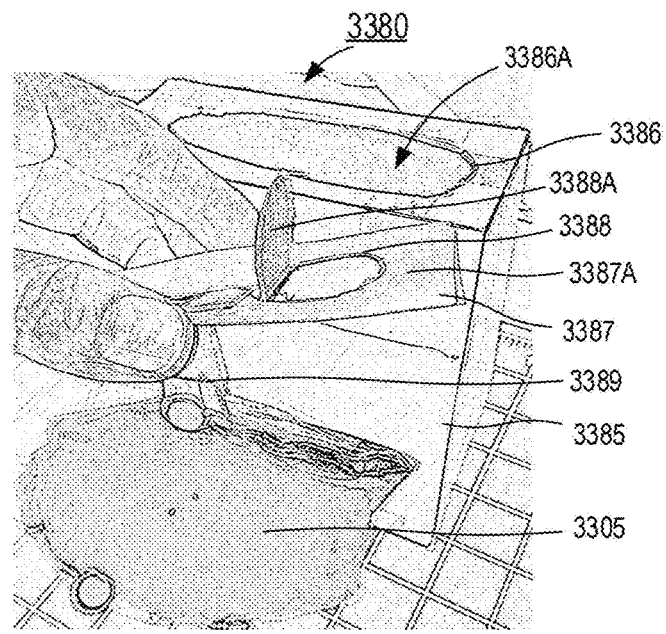
Figure 98:
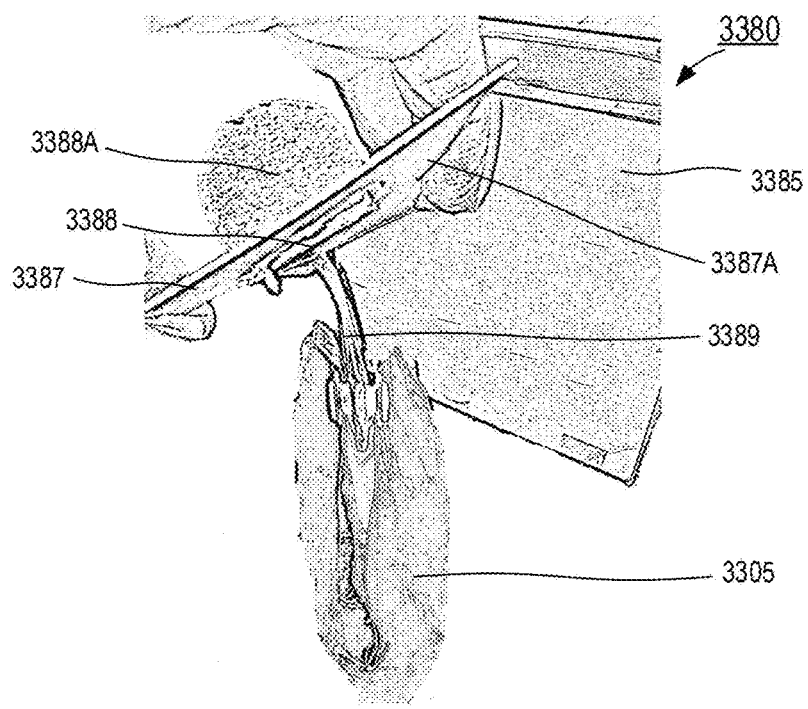

In still other embodiments, a therapeutic member can receive thermal energy by being at least partially disposed, for example, in a warm bath of a fluid (e.g., water). For example, FIGS. 96-98 illustrate a heating mechanism 3380 according to another embodiment. The heating mechanism 3380 includes a reservoir 3385 and a hanging mechanism 3387. The reservoir 3385 includes a top surface that defines an opening 3386 configured to allow access to an inner volume 3386A of the reservoir 3385, as shown in FIGS. 96 and 97. The reservoir 3385 can be any suitable shape, size, or configuration. For example, in some embodiments, the reservoir 3385 can be formed from and/or can include an insulating material or the like that can, for example, limit a transfer of thermal energy from the inner volume 3386A to a volume substantially outside of the reservoir 3385.

The hanging mechanism 3387 can be any suitable configuration and is configured to be at least partially disposed in the inner volume 3386A of the reservoir 3385, as described in further detail herein. The hanging mechanism 3387 includes a base 3387A and a hanger 3389. The base 3387A can be any suitable shape, size, or configuration. For example, in some embodiments, the base 3387A can have a size and a shape that substantially corresponds with and/or is otherwise associated with the top surface of the reservoir 3385. In this manner, the base 3387A can be disposed on and/or positioned adjacent to the top surface of the reservoir 3385 to insert the hanger 3389 through the opening 3386 such that a portion of the hanger 3389 is disposed in the inner volume 3386A of the reservoir 3385. As shown, the base 3387A defines an opening 3388 that can, for example, allow access to the inner volume 3386A of the reservoir 3385 when the base 3387A is disposed on and/or adjacent to the top surface of the reservoir 3385, as described in further detail herein.

As shown in FIGS. 96-98, the hanging mechanism 3387 is configured to be coupled to a therapeutic member 3305. The therapeutic member 3305 can be any suitable member such as any of those described herein (e.g., the therapeutic member 3305 can be substantially similar to or the same as the therapeutic member 305 described in detail above). More specifically, the hanger 3389 extends from a surface of the base 3387A and has an end portion configured to be coupled to the therapeutic member 3305. For example, in some embodiments, the end portion of the hanger 3389 can include a coupling mechanism such as, for example, a snap and/or the like that can be matingly coupled to a corresponding coupling mechanism (e.g., a corresponding snap) of the therapeutic member 3305. As such, the therapeutic member 3305 can be removably coupled to the hanger 3389. Moreover, with the hanger 3389 coupled to the therapeutic member 3305, the therapeutic member 3305 can be disposed in the inner volume 3386A of the reservoir 3385 when the base 3387A of the hanging mechanism 3387 is positioned on and/or adjacent to the top surface of the reservoir 3385.

For example, in use, a patient and/or user can couple the therapeutic member 3305 to the end portion of the hanger 3389, as shown in FIGS. 96-98. Once coupled, the user can move the hanging mechanism 3387 to a position that places the base 3387A on and/or otherwise adjacent to the top surface of the reservoir 3385. As such, the therapeutic member 3305 and the hanger 3389 can be inserted through the opening 3386 to be disposed in the inner volume 3386A of the reservoir 3385. With the base 3387A disposed on and/or adjacent to the top surface, the user can, for example, move a lid or the like to expose the opening 3388 of the base 3387A. In this manner, the opening 3388 can allow access to the inner volume 3386A of the reservoir 3385 (e.g., via the opening 3386).

With the opening 3388 exposed, the user can, for example, pour a fluid into the opening 3388 of the hanging mechanism 3387 and the opening 3386 of the reservoir 3385 and into the inner volume 3386A. In some instances, the fluid can be a predetermined volume of the fluid that is preheated to a desired temperature. For example, in some instances, the fluid can have a volume of about 16 fluid ounces (fl. oz.) and can be heated substantially to the boiling point of the fluid. In this manner, the therapeutic member 3305 can be immersed in the volume of the fluid, which in turn, can transfer a portion of thermal energy from the fluid to the therapeutic member 3305. In some embodiments, the therapeutic member 3305 can be immersed in the fluid for a predetermined time period. For example, in some instances, the therapeutic member 3305 can be immersed in about 16 fl. oz. of boiling-hot water for about 60 seconds, which can heat, for example, the contents of the therapeutic member 3305 (e.g., approximately 7 ounces of thermal gel, as described in detail above) to approximately 120 F. Thus, after the predetermined time period and/or after a desired amount of thermal energy has been transferred to the therapeutic member 3305, the hanging mechanism 3387 can be moved relative to the reservoir 3385 to remove the therapeutic member 3305 from the inner volume 3386A. In this manner, the therapeutic member 3305 can be decoupled from the hanger 3389 and coupled to a therapeutic device (not shown in FIGS. 96-98), such as those described herein.

Although described above as pouring a preheated volume of fluid into the inner volume 3386A of the reservoir 3385, in other embodiments, a volume of non-heated fluid can be poured into the inner volume 3386A and heated, for example, by a portion of the reservoir 3385. For example, in some embodiments, the reservoir 3385 can include a heating element and/or the like that can be heated (e.g., via a flow of electrical current and/or the like) to transfer thermal energy to the volume of fluid. Although the volume of fluid is specifically described, for example, as being about 16 fl. oz., in other embodiments, any suitable volume of fluid can be poured into the inner volume 3386A (e.g., a volume that is less than the inner volume to prevent overflowing and/or the like when the therapeutic member 3305 is disposed in the inner volume 3386A). In some instances, the reservoir 3385 can include indicia and/or the like that can be associated with a desired fill level (i.e., a desired volume of fluid). For example, the indicia can be a fill line and/or the like. Furthermore, while not shown in FIGS. 96-98, in some embodiments, a portion of the reservoir 3385 and/or a portion of the hanging mechanism 3387 can include a relatively small hole (e.g., a pin hole or the like) that can, for example, allow steam and/or the like the vent from the inner volume 3386A. As such, the inner volume 3386A can be maintained with a pressure that is below a predetermined threshold (e.g., a pressure threshold that could damage the reservoir 3385, the therapeutic member 3305, and/or the hanging mechanism 3387, and/or that could otherwise result in an uncontrolled release of pressure such as, for example, the base 3387A of the hanging mechanism 3387 being forcibly removed from the top surface of the reservoir 3385).

Although not shown in FIGS. 96-98, in some embodiments, the arrangement of the hanging mechanism 3387 can be such that when the hanger 3389 is coupled to the therapeutic member 3305 and the base 3397A is disposed on and/or adjacent to the top surface, the coupling mechanism of the hanger 3389 and thus, the coupling mechanism of the therapeutic member 3305 (as described above) are not substantially immersed in the volume of the fluid. For example, with a predetermined volume of fluid disposed in the inner volume 3386A of the reservoir 3385 and with the therapeutic member 3305 substantially immersed therein, the coupling mechanism of the hanger 3389 (e.g., one or more snaps) and the corresponding coupling mechanism of the therapeutic member 3305 (e.g., one or more corresponding snaps) are not substantially immersed in the volume of the fluid. As such, damage to the coupling mechanism as a result of immersion in the volume of fluid can be reduced and/or eliminated.

Figure 99:
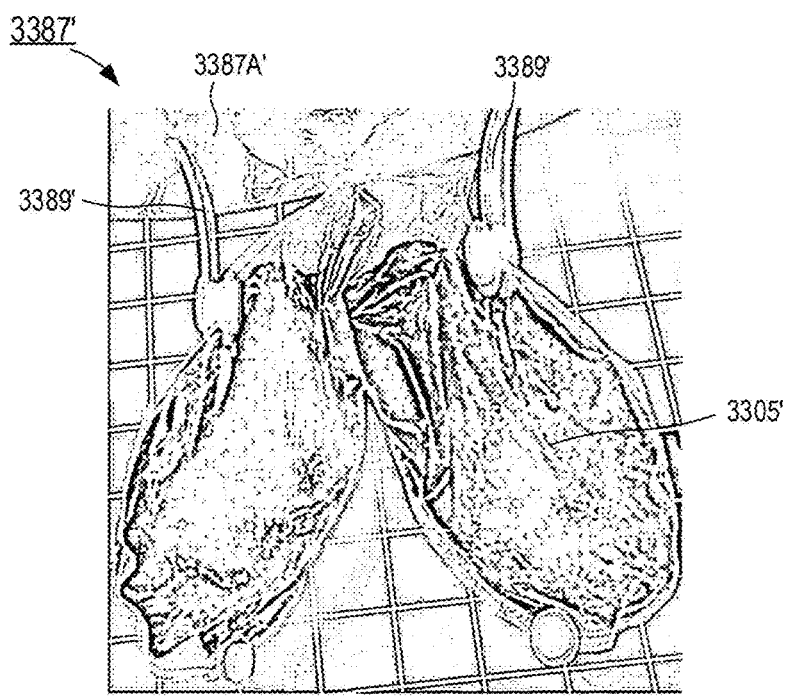
FIG. 99 is a perspective view of a hanger of a heating device according to an embodiment.

While the hanger 3389 is shown in FIG. 98 as being a single substantially elongate member that extends from the base 3387A, in other embodiments, a hanging mechanism can include one or more hangers having any suitable configuration. For example, FIG. 99 illustrates a hanging mechanism 3387' according to an embodiment. In some instances, the hanging mechanism 3387' can be used, for example, with the reservoir 3385 to transfer thermal energy to a therapeutic member 3305'. The hanging mechanism 3387' includes a base 3387A' and a hanger 3389'. The base 3387A' can be substantially similar in form and function to the base 3387A described above. As shown in FIG. 99, the hanger 3389' can include and/or can form two substantially elongate members that are each coupled to a different portion of the therapeutic member 3305'. In this manner, the hanging mechanism 3387' can function substantially similar to and/or the same as the hanging mechanism 3387 described above with reference to FIGS. 96-98.

Although the hanging mechanism 3387 of FIGS. 96-98 and the hanging mechanism 3387' of FIG. 99 include the hangers 3389 and 3389', respectively, in other embodiments, a hanging mechanism can be coupled to a therapeutic member in any suitable manner such that when the therapeutic member is coupled thereto and is disposed in a volume of fluid, the coupling mechanism of the therapeutic member is not substantially immersed in the fluid. In other embodiments, a therapeutic member can be coupled directly to an inner surface of a reservoir in such a manner that when the reservoir is filled with a volume of fluid and the therapeutic member is substantially immersed therein, a coupling mechanism of the therapeutic member is not substantially immersed in the fluid.

Figure 101:
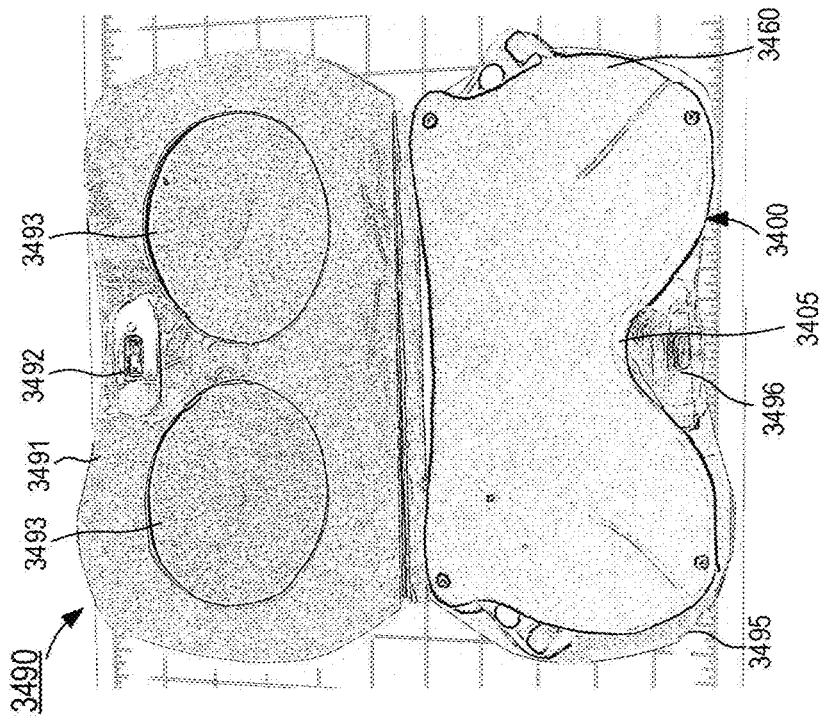
FIG. 101 is a top view of a therapeutic device disposed in the shipping package of FIG. 100.
Figure 100:
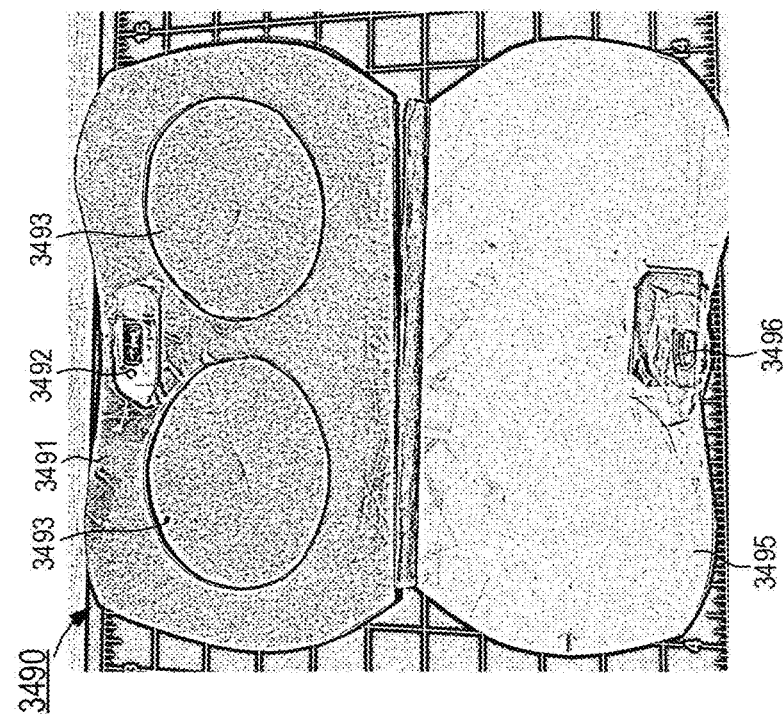
FIG. 100 is a top view of a shipping package configured to receive a therapeutic device in a first configuration, according to an embodiment.

Any of the therapeutic devices and/or components thereof described herein can be disposed in any suitable packaging or the like prior to use (e.g., during shipping or the like). For example, FIGS. 100-103 illustrate a packaging 3490 configured to receive a therapeutic device 3400, according to an embodiment. In some embodiments, the packaging 3490 can be used, for example, to support and/or prevent damage to the therapeutic device 3400 during shipping and/or storage. The packaging 3490 includes a first side 3491 and a second side 3495. In some embodiments, the packaging 3490 can be formed from relatively rigid material that can resist deformation (e.g., bending, buckling, flexing, and/or otherwise reconfiguring) when exposed to an external force. The first side 3491 includes a set of engagement portions 3493 and a closure member 3492. The engagement portions 3493 can be, for example, a substantially conical structure that can be aligned with a convex portion of an insulating member included in the therapeutic device 3400 (e.g., as described above with reference to the first insulating member 360 of the therapeutic device 300), as shown in FIG. 101. Moreover, the engagement portions 3493 can be configured to form a convex structure or surface relative to an outer surface of the first side 3491 and can form a concave structure or surface relative to an inner surface of the first side 3491.

Figure 102:
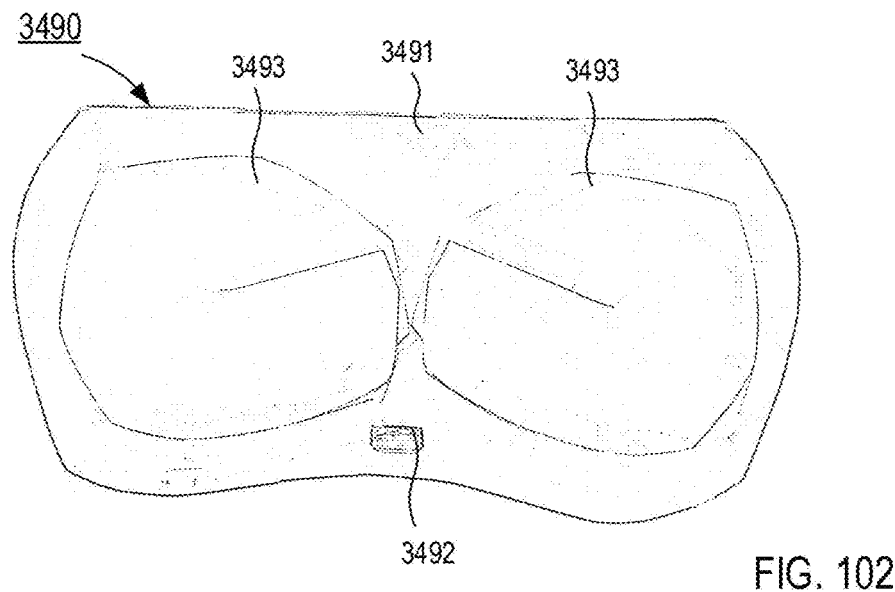
FIGS. 102 and 103 are a top view and a perspective view, respectively, of the shipping package of FIG. 100 in a second configuration.
Figure 103:
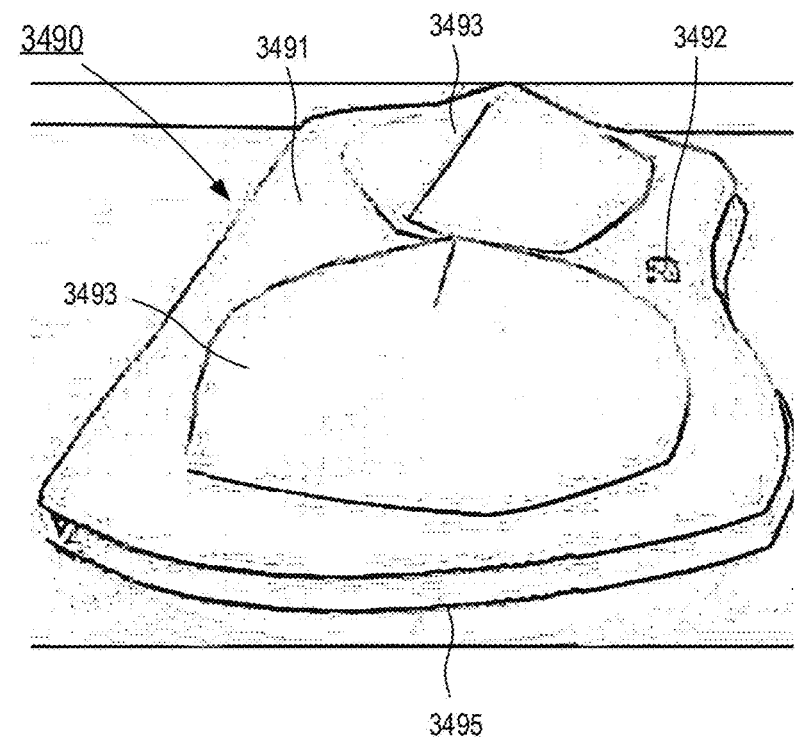

The second side 3495 of the packaging 3490 can be substantially flat and can include a closure member 3496 configured to engage the closure member 3492 of the first side 3491. In this manner, the therapeutic device 300 can be placed on the second side 3495 of the packaging 3495. As shown in FIGS. 102 and 103, the first side 3491 of the packaging 3490 can be moved relative to the second side 3491 to substantially enclose the therapeutic device 3400 therebetween. Moreover, the first side 3491 can be moved such that the engagement portions 3493 each receive a portion of the therapeutic device 3400. Expanding further, the substantially conical shape of the engagement portions 3493 conform and/or otherwise provide space for the convex portions of the therapeutic device 3400 (e.g., convex portions of a first lobe and second lobe of an insulating member, as described above with reference to the therapeutic device 300). In this manner, the engagement portions 3493 can substantially protect the convex portions of the therapeutic device 3400 from an external force (e.g., during shipping, storage, or the like) that can otherwise result in a deforming of the convex portions.

In some embodiments, the packaging 3490 can be configured so that when the first side 3491 and the second side 3492 of the packaging 3490 are moved toward one another so as to substantially enclose the therapeutic device 3400 therebetween, a compression force is exerted on a peripheral region of therapeutic device 3400 to sandwich the therapeutic device 3400 between the inner surfaces of sides 3491 and 3492. In contrast, the central regions of therapeutic device 3400 including the central lobes of an insulating member 3460 and a therapeutic member 3405 (e.g., similar to or the same as the insulating member 360 and the therapeutic member 305, described above) are substantially not exposed to the compression force, due, at least in part, to the convex engagement portions 3493 described above which can allow a vaulting above the convex portions of the insulating member 3460. Thus, as pressure is placed upon the peripheral regions of the therapeutic device 3400 by the packaging 3490, portions of the contents of the therapeutic member 3405 (e.g. gelatinous substances) can be displaced from the peripheral regions of therapeutic member 3405 and toward the central regions, including those regions underlying the convex portions of both the insulating member 3460 and the packaging 3493, as described above. The inflow of gel into these central regions can, for example, provide further structural support underneath the convex portions of the lobes of the first insulating member 3460, thus improving the stability and shaping of the convex portions of the insulating member 3460 during storage and/or the like. In some embodiments, the sides 3491 and 3492 of packaging 3490 can be left open. In other words, while the packaging 3490 is shown and described above as substantially fully protecting the contents (e.g., the therapeutic device 3400) prior to the opening of the packaging 3490, the packaging 3490 can be structured without such full protection. Such absence of peripherally closed side walls can, for example, reduce manufacturing costs, improve reusability, and reduce an overall space needed when the packaging 3490 is enclosed in other materials.

Figure 105:
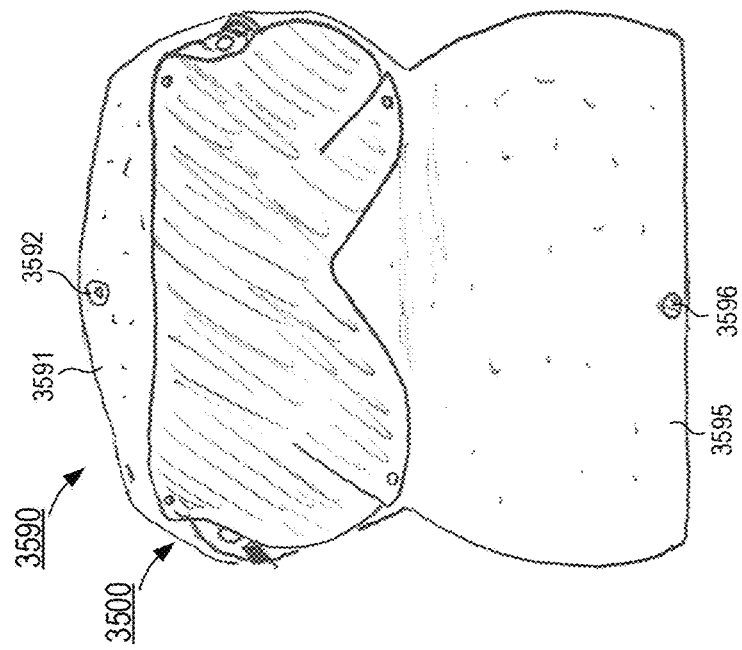
FIG. 105 is a top view of a therapeutic device disposed in the shipping package of FIG. 104.
Figure 104:
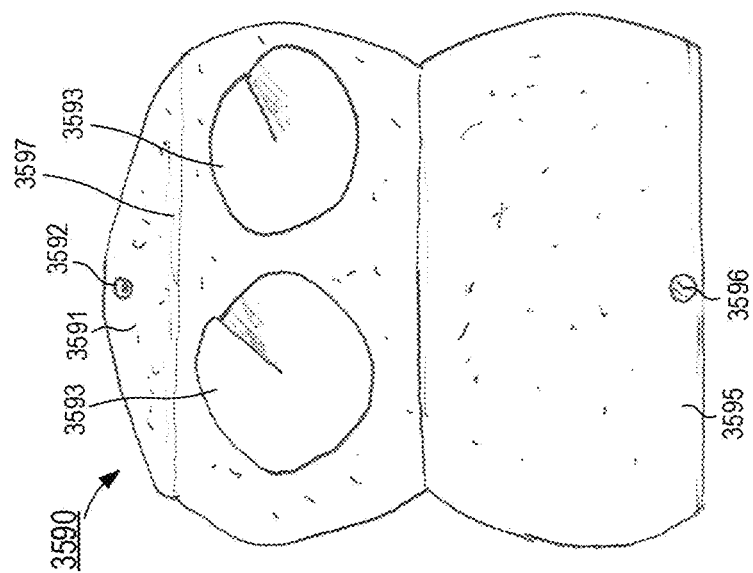
FIG. 104 is a top view of a shipping package configured to receive a therapeutic device in a first configuration, according to an embodiment.

While the packaging 3490 is shown in FIGS. 100-103 as including the engagement portions 3493 that are concave relative to an inner surface, in other embodiments, a packaging can include one or more engagement portions that can be convex relative to an inner surface. For example, FIGS. 104-106 illustrate a packaging 3590 according to another embodiment. The packaging 3590 includes a first side 3591 and a second side 3595. The first side includes a set of engagement portions 3593 and a closure member 3592. The engagement portions 3593 can be substantially conical structures that extend from an inner surface of the first side 3591. Similarly stated, the engagement portions 3593 can be convex structures relative to the inner surface of the first side 3591. The engagement portions 3593 can be arranged to support and/or protect a convex portion of a therapeutic device 3500, as shown in FIG. 105. The closure member 3592 can have a portion that extends from the inner surface of the first side, and can be separated from the remainder of the first side 3591 by a flexible hinge element 3597. The second side 3595 of the packaging 3595 can be substantially flat and can include a closure member 3596 having a portion extending from an exterior surface of the second side and configured to engage the portion of the closure member 3592 extending from the inner surface of the first side 3591 when the flexible hinge element 3597 is in a flexed or substantially closed position. In this manner, the therapeutic device 3500 can be placed on the first side 3591 such that the engagement portions 3593 are substantially aligned with the convex portions of the therapeutic device 3500. The second side 3595 can be moved relative to the first side 3591 to substantially enclose the therapeutic device 3500 therebetween. Once the second side 3595 is moved relative to the first side 3591, the closure members 3592 and 3596 can be placed into contact, as described above, to retain the packaging 3590 in a closed configuration, as shown in FIG. 106.

Figure 107:
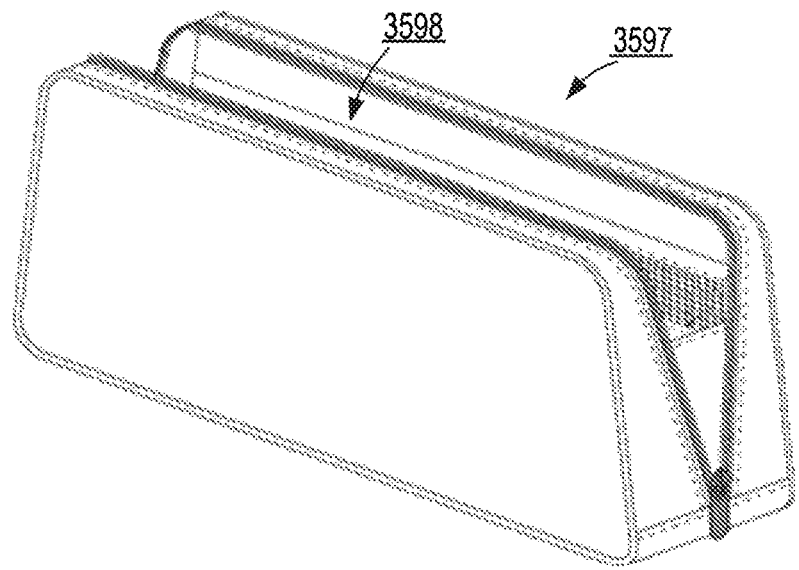
FIGS. 107 and 108 are perspective views of a case configured to receive a therapeutic device in an open configuration and a closed configuration, respectively, according to an embodiment.
Figure 108:
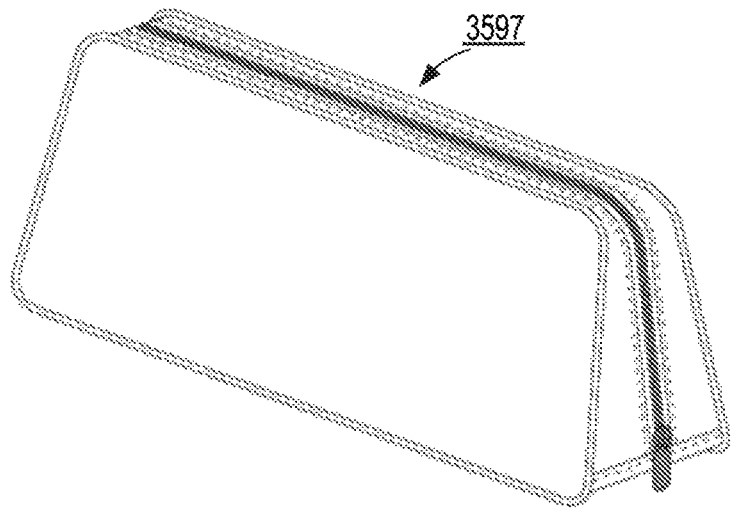
Figure 109:
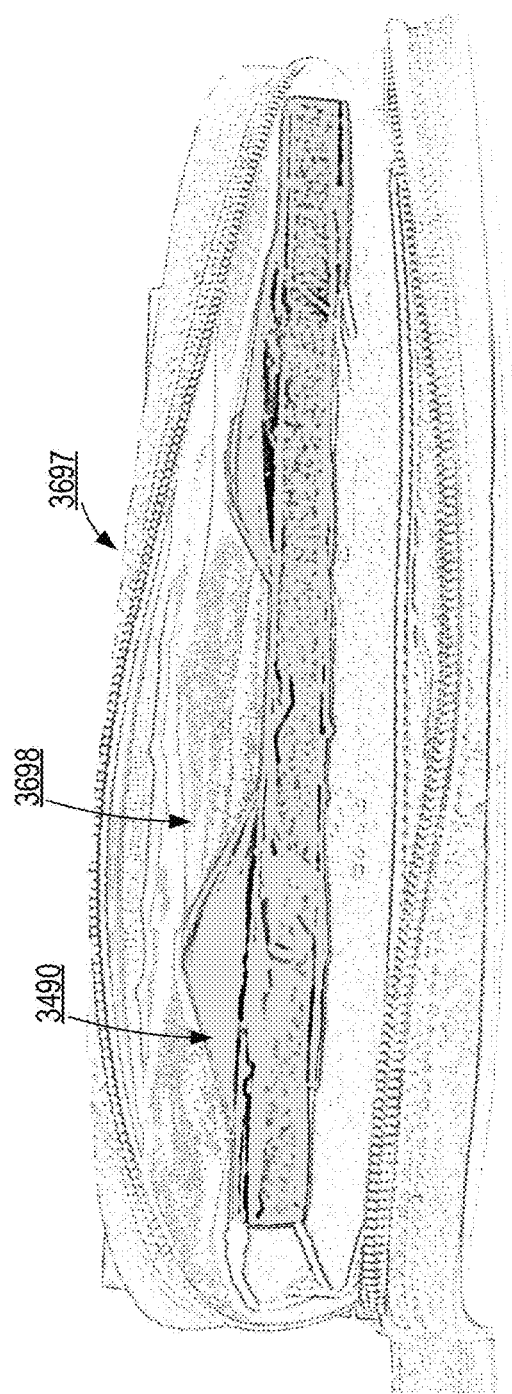
FIG. 109 is a top view of the shipping package of FIGS. 100-103 disposed in the case of FIGS. 107 and 108.

Referring now to FIGS. 107-109, any of the embodiments described herein can be stored in a case 3597 while not in use. The case 3597 can be any suitable shape, size, or configuration. For example, in some embodiments, the case 3597 can be a relatively soft pouch or the like that can define an inner volume 3598 configured to receive and store a therapeutic device. In some embodiments, the case 3597 can include a zipper closure system that can be manipulated to gain access to the inner volume 3598. In some embodiments, the case 3597 can have a base surface and a top surface, wherein a width of the base surface is greater than a width of the top surface. The wide base can allow stable upright storage of the case 3597, whether the case 3597 is stored with or without contents. As shown in FIG. 109, in some embodiments, the case 3597 can be sufficiently large such that the packaging 3490, with a therapeutic device (not shown) disposed therein, can be inserted into the inner volume 3598. Thus, the case 3597 can be configured to house and/or protect any of the therapeutic devices described herein while not in use.

Figure 110:
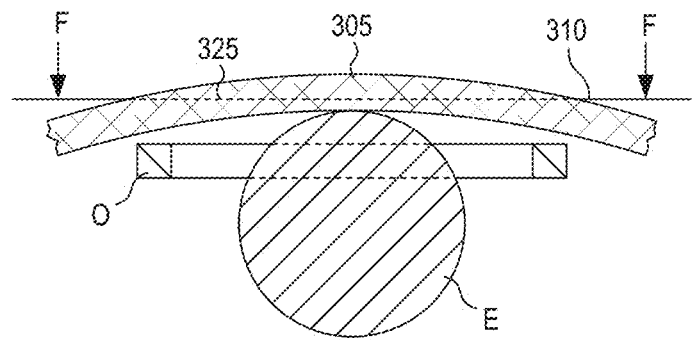
FIG. 110 is a cross-sectional schematic view of a portion of the therapeutic device of FIGS. 5 and 6 disposed adjacent to the face of a user.

Any of the therapeutic devices described herein can be configured to reduce and/or substantially diffuse a direct rearward force on the lobe of the eye. For example, the frame 310 defines the set of apertures 325 that can allow a portion of the therapeutic member 305 to extend therethrough, thereby reducing a rearward force exerted on the eye. More specifically, by selectively reducing the stiffness of the frame 310, and/or by providing apertures 325 (as described in detail above) which circumscribe a large perimeter (such as a perimeter substantially outside of an orbital rim O), a rearward force F effected by frame 310 can be distributed about a larger area of the ocular region (e.g., substantially outside of the orbital rim O), which, in turn, reduces direct rearward pressure on the eye E, as shown, for example, in FIG. 110. Thus, the frame 310 and the therapeutic member 305 can exert rearward force on the eye that is lower than a force that would otherwise be exerted by, for example, a frame and therapeutic member that did not distribute the force substantially beyond or outside of the orbital rim (e.g., a frame with greater stiffness, a frame lacking apertures, a smaller frame, or the like).

Figure 111:
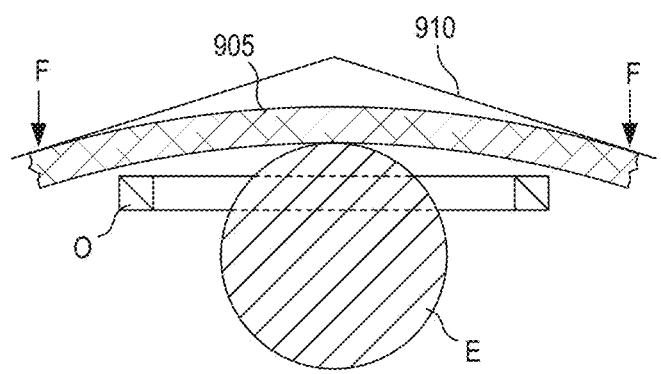
FIG. 111 is a cross-sectional schematic view of a portion of the therapeutic devices of FIG. 50 or FIG. 55 disposed adjacent to the face of a user.

The arrangement of the frame 910 when coupled to the head of a user can similarly diffuse and/or distribute a direct rearward pressure on the eye. More specifically, by arranging the frame 910 such that the lobes have and/or form a broad convex shape, the apex of the convex-shaped lobes can be displaced anteriorly away from the globe of the eye a sufficient distance such that the therapeutic member 905 disposed therebetween is substantially not in contact with the apex. Thus, as shown in FIG. 111, the rearward force F is diffused and/or otherwise distributed on an area of the face of the user that is beyond or outside of the orbital rim O. In this manner, the frame 910 can, for example, sandwich, clamp, pin, hold, or otherwise maintain a portion of the therapeutic member 905 between a peripheral portion of the frame 910 and a portion of the face outside of the orbital rim O.

Figure 112:
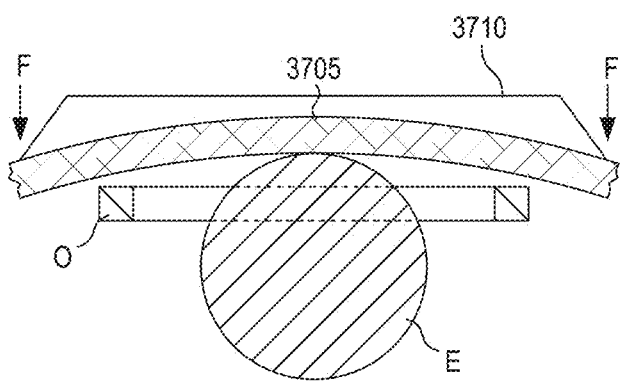
FIG. 112 is a cross-sectional schematic view of a portion of a therapeutic device disposed adjacent to the face of a user according to another embodiment.

Although the lobes of the frame 910 form a substantially convex shape that is operable in distributing the rearward force F on an area outside of the orbital rim O, in other embodiments, a frame can have a lobe (or two lobes, each associated with one eye of the user) forming any suitable shape while still distributing the rearward force exerted by frame on an area of the face outside of the orbital rim. For example, as shown in FIG. 112, a frame 3710 can have a lobe with a substantially planar anterior surface and sides that extend posteriorly therefrom (e.g., a lobe having a substantially trapezoidal cross-sectional shape). Moreover, the frame 3710 can be arranged such that the sides of the lobe are in contact with a portion of the face of the user that is outside of the orbital rim O, and the anterior surface is spaced apart from the globe of the eye E a sufficient distance such that a therapeutic member 305 is substantially not in contact with the anterior surface. Thus, the rearward force F is diffused and/or distributed on an area of the face that is beyond or outside of the orbital rim O.

Any of the therapeutic devices described herein can be used, for example, to provide a therapeutic treatment to the ocular region of a user to treat any suitable illness, condition, and/or the like. For example, in some instances, any of the embodiments described herein can be used to treat dry eye. In general, some therapeutic treatments of dry eye include applying heated or cooled thermal therapy to the eye regions, and specifically to the meibomian glands of the eyelids. In some instances, heated thermal therapy, as applied by a therapeutic device such as those described herein, is recommended for treatment of dry eye syndrome due, at least in part, to the application of heat being operable in melting solidified fats within clogged meibomian glands, thereby allowing meibomian gland oils to be more easily secreted onto the tear film. Heating regimens for eyelid oil glands typically include instructions based on temperature and time considerations, and include the use of electronic or chemically-controlled heat output devices that are configured to provide a predetermined amount and duration of heating, as well as more simplistic instructions for heated eye compress systems such as, for example, "heat with warm water or warm washcloths for 4 minutes," "apply for 10 to 15 minutes," etc.

The etiology of dry eye syndrome is multifactorial. One of the contributing factors in dry eye syndrome is ocular surface irritation. Such irritation can arise from exogenous sources (such as dry ambient air and contact lens wear) or endogenous sources (such as blepharitis, poor aqueous production, impaired lipid production, etc.). Ocular surface irritation exacerbates dry eye syndrome by triggering neurohumoral responses, resulting in the release of proinflammatory chemical mediators. Such chemicals cause further ocular irritation, and contribute to a self-sustaining negative cycle, resulting in a worsening of dry eye signs and symptoms.

In some methods for treating eye symptoms, which can include dry eye syndrome, evaporative dry eye, and/or the like, users can be instructed to apply heated or cooled eye compress therapy without specific limitations regarding temperature or duration. In other instances, users can be directed in ways to optimize the comfort of treatment by varying certain parameters to obtain temperatures and durations of treatment that are tailored to a user, based at least in part on subjective, feeling-sensation criteria that is selected by the user.

As described in further detail herein, users with symptoms of dry eye syndrome were tested using, for example, the therapeutic device 300 of FIGS. 5-44 with a treatment method optimized for patient comfort. For example, the method of use of the therapeutic device 300 included having the user adjust his or her therapeutic treatments to provide maximal comfort during use. In this manner, the dry eye treatment supplanted commonly known, objectively quantifiable, and highly standardized treatment targets such as duration, temperature, quantity, etc. with a subjective and highly variable measure of each individual user's subjective experience of immediate comfort. The immediate goal of therapy using, for example, the therapeutic device 300 was to provide user comfort during treatment. The results of treatment, however, included profound and unexpected advantages in the area of chronic reduction of dry eye symptoms.

Testing showed that treatment optimized for comfort using, for example, the therapeutic device 300, resulted in significant reductions in ocular discomfort acutely (e.g., within 20 seconds to 5 minutes), subacutely (e.g., over a 4-week period), and long-term (e.g., over at least an 8-month period). Thus, the results of the testing using, for example, the therapeutic device 300 showed that using treatment with therapeutic devices 300 with methods optimized for comfort can be at least as effective at reducing symptoms of moderate to severe dry eye as standardized therapy with artificial tears, cyclosporine preparations such as those found in certain prescription medications, and advanced-technology devices such as eyelid heating and eyelid gland evacuation mechanisms found, for example, in certain class II medical devices, and/or the like. It is possible that, in some instances, treatment of moderate to severe dry eye using, for example, the therapeutic device 300, can result in an interruption of irritative signals to neural synapses, thus downregulating the neurohumoral cascade that leads to ocular surface inflammation. As such, the provision of comfort with the therapeutic device 300 and a method of its use may result in an approach to anti-inflammatory treatment of, for example, dry eye syndrome, that is heretofore substantially unknown.

Figure 113:
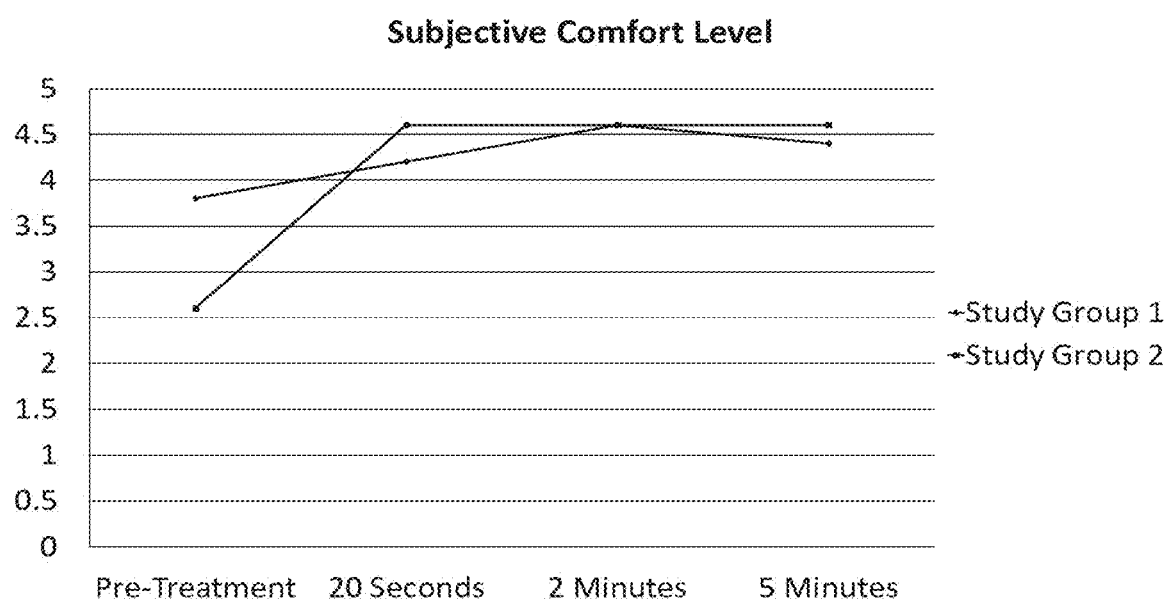
FIGS. 113-118 are graphs illustrating test data using a therapeutic device according to an embodiment.

By way of specific example, users with dry eye syndrome were randomly assigned to two study groups of 5 patients each. The first study group was directed to receive an artificial tear drop, while the second study group was directed to receive a hot compress treatment using, for example, the therapeutic device 300. Users were asked to provide an ocular comfort rating (on a scale of 1 to 5, with 1 being very uncomfortable and 5 being very comfortable) before treatment, at 20 seconds, at 2 minutes, and at 5 minutes. Compared to users in the first study group, users in the second study group sustained their positive response for a longer period as well as having a more rapid increase in ocular comfort, as shown in Table 4 and graphically in FIG. 113.

TABLE 4

| Study Group | Score Pre-Treatment | Score 20 seconds | Score 2 minutes | Score 5 minutes |
| --- | --- | --- | --- | --- |
| 1 | 3.8 | 4.2 | 4.6 | 4.4 |
| 2 | 2.6 | 4.6 | 4.6 | 4.6 |

Figure 114:
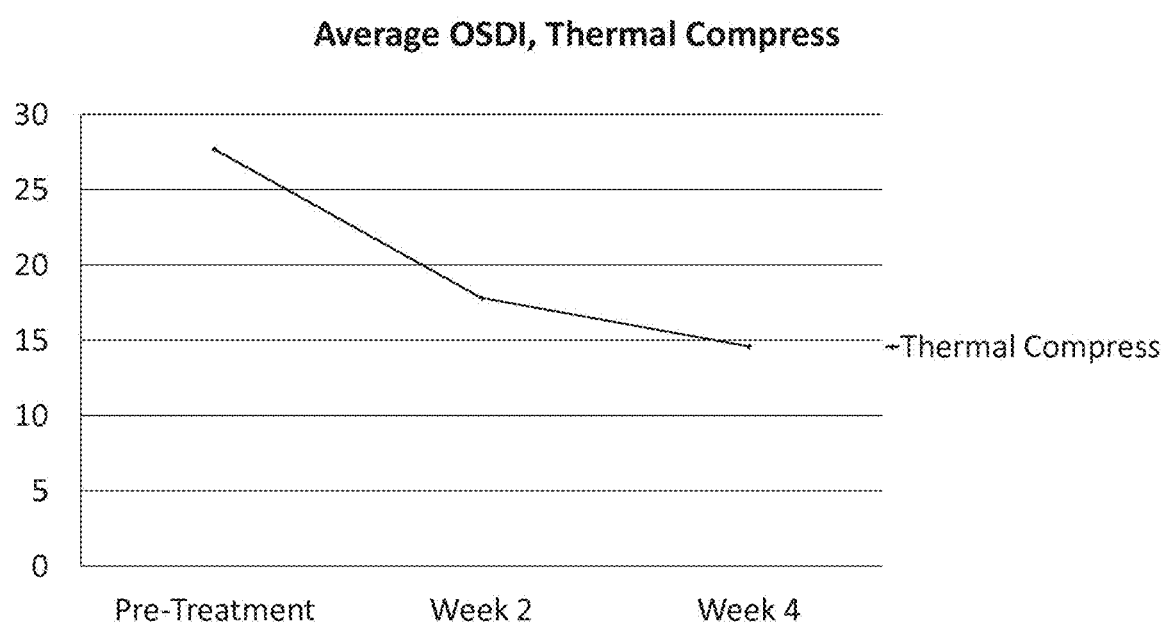

In another specific example, 15 users with dry eye symptoms were assigned to receive a 4-week intervention of home-use hot compress therapy using, for example, the therapeutic device 300. Users were instructed on methods of use of the therapeutic device aimed at optimizing personal comfort. Users recorded symptoms on a standardized Ocular Surface Disease Index (OSDI™) chart (Allergan, Irvine Calif.) at pre-testing, 2 weeks, and 4 weeks. OSDI scores were calculated, as shown in Table 5 and graphically in FIG. 114.

TABLE 5

| | Pre-Treatment | Week 2 | Week 4 |
| --- | --- | --- | --- |
| Average OSDI | 27.67 | 17.84 | 14.66 |

Figure 115:
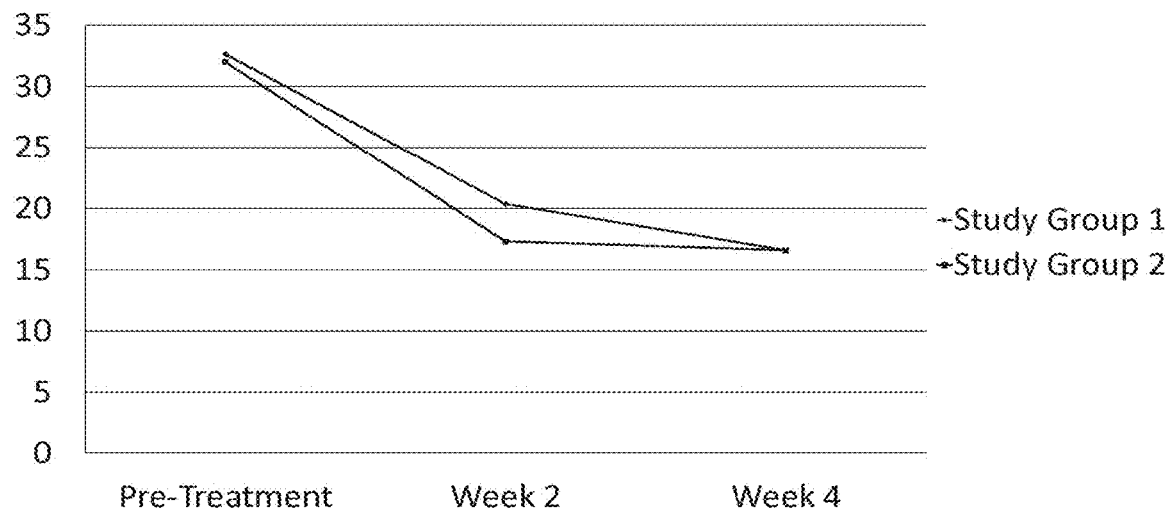

As shown, for the group of 15 users, average OSDI scores improved from a baseline of 27.7 to 17.8 after 2 weeks, and to 14.7 after 4 weeks. To compare results with those of other dry eye treatments, however, selected subgroups were chosen. For example, the most severely-affected 12 users of the therapeutic device 300 (study group 1), with a baseline OSDI score of 32.6, were compared to published results of a group of 70 patients tested on a LipiFlow® device (study group 2), with such patients having a baseline OSDI score of 32. The results are shown in Table 6 and graphically in FIG. 115.

TABLE 6

| Study Group | Score Pre-Treatment | Week 2 | Week 4 |
| --- | --- | --- | --- |
| 1 | 32.65 | 20.39 | 16.59 |
| 2 | 32 | 17.3 | 16.6 |

After 2 weeks of intervention, the OSDI scores of the study group 2 were reduced to 17.3, compared to 20.4 for the study group 1. At 4 weeks of intervention, however, both the study group 1 and the study group 2 had decreased to about 16.6.

Figure 116:
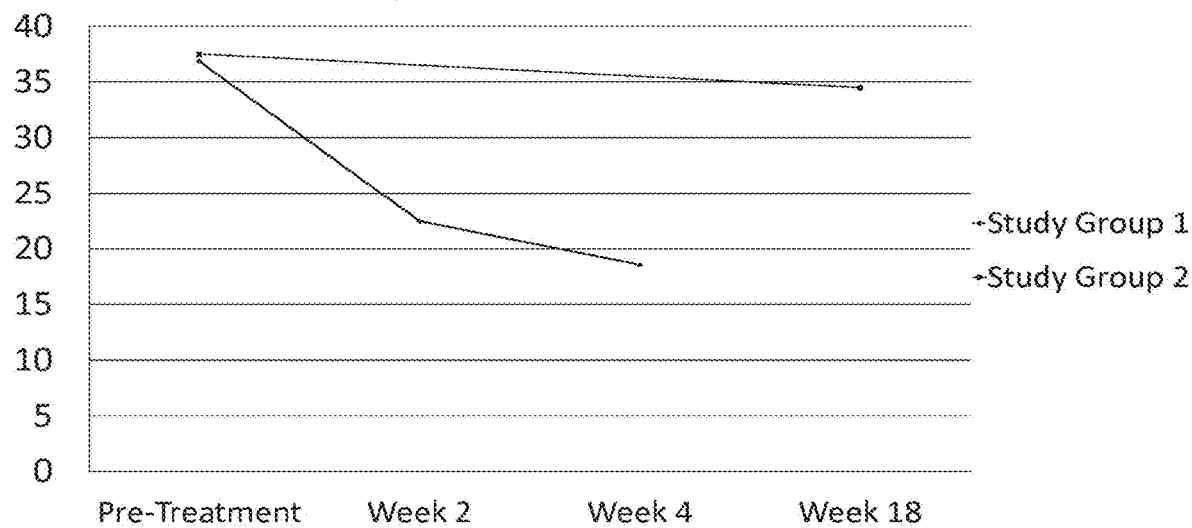

In addition, the most severely-affected 10 users of the therapeutic device 300 (study group 1), with a baseline OSDI score of 36.9, were compared to published results of a group of patients tested on cyclosporine 0.05%, similar to a drug referred to as Restasis® (study group 2). After 2 and 4 weeks, respectively, the OSDI scores of the study group 1 decreased to 22.5 and 18.5. In contrast, the OSDI scores of the study group 2 decreased from a pre-treatment score of 37.5 to 34.5 at the end of 12 weeks of therapy, as shown in Table 7 and graphically in FIG. 116.

TABLE 7

| Study Group | Score Pre-Treatment | Week 2 | Week 4 | Week 18 |
|---|---|---|---|---|
| 1 | 36.89 | 22.47 | 18.54 | |
| 2 | 37.5 | | | 34.5 |

Figure 117:
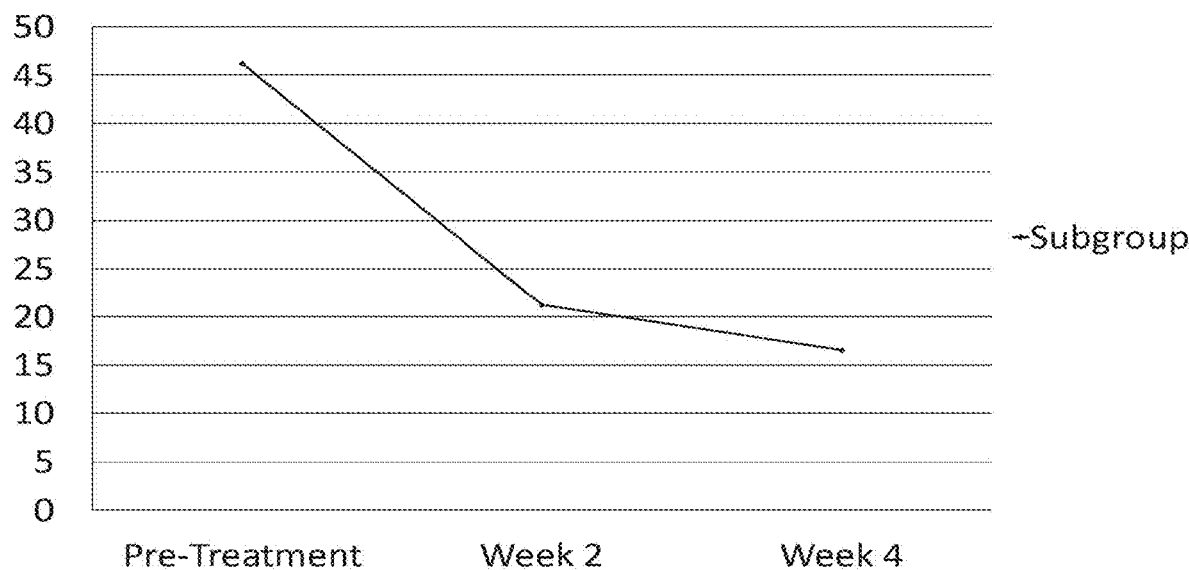

The improvement in OSDI scores among users of the therapeutic device 300 were most dramatic for users whose baseline OSDI scores were >20. This subgroup, which had an average baseline OSDI score of 46.2, decreased to 21.2 at 2 weeks and 16.6 at 4 weeks. In other words, despite beginning with much more severe OSDI scores than any other group tested, this subgroup with the most severe symptoms scored as well at the end of 4 weeks as users who had begun with much lower levels of discomfort. The results for the subgroup are shown in Table 8 and graphically in FIG. 117.

TABLE 8

| Subgroup | Score Pre-Treatment | Week 2 | Week 4 |
|---|---|---|---|
| 1 | 46.2 | 21.22 | 16.56 |

In another specific example, a test user with a long history of ocular discomfort began home treatment using, for example, the therapeutic device 300. The user was instructed to adjust the preparation and use of the therapeutic device 300 according to personal preference. Said another way, the subject's use of the therapeutic device 300 was guided by instruction in methods of use, wherein the methods of use encouraged the user to adjust parameters based on subjective feelings of immediate comfort.

The test user's prior history of eye problems spanned several years and included chronically "sore" and "tired" eyes, fluctuating vision, ocular hyperemia, and contact lens intolerance. The user was previously treated with punctal plugs, preservative-free artificial tears, preservative-free bedtime ointment, Restasis® brand cyclosporine drops, tobramycin-dexamethasone drops and ointments, and therapy with a heated eye chamber device. Despite the interventions, the test user found no sustained resolution of symptoms and had remained unable to tolerate contact lens wear for at least 18 months.

Figure 118:
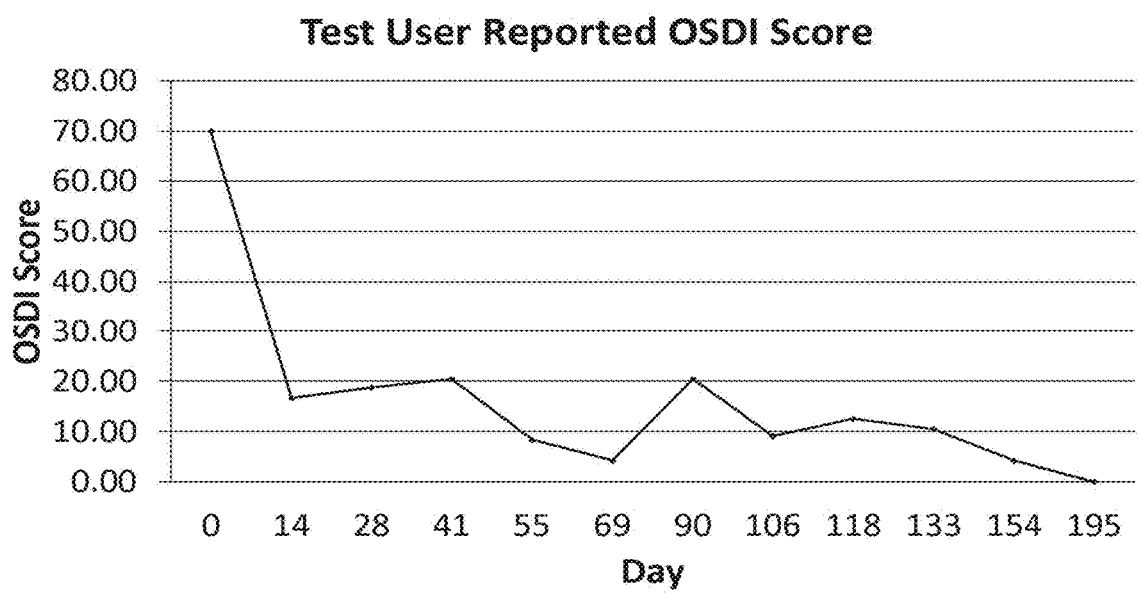

Within 2 weeks of beginning home use of the therapeutic device 300, the test user noted significant improvement in eye symptoms. Within 6 weeks the user had resumed contact lens wear. The user reported a decrease in redness, "tiredness" of the eyes, discharge, and discomfort. The user also reported others noting changes in the eyes' appearance (e.g., noticeable reduction in "redness"). The user maintained use of the therapeutic device 300 on a daily basis long after the duration of the study, for at least 8 months, reporting continued ocular comfort, ability to wear contact lenses, and decreased ocular redness. The user's reported OSDI score is graphically represented in FIG. 118.

Figure 119:
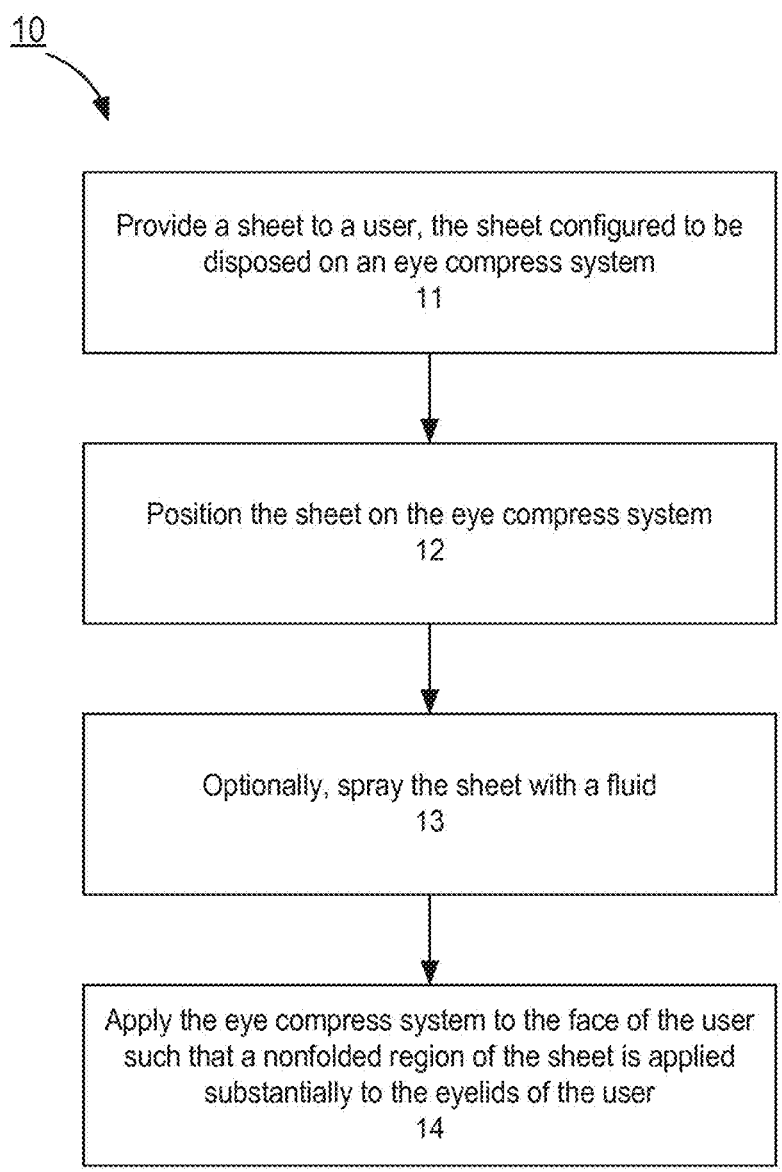
FIG. 119 is a flowchart illustrating a method of using a sheet on a therapeutic device according to an embodiment.

Referring now to FIG. 119, a flowchart is shown illustrating a method of using, for example, a therapeutic device, according to an embodiment. More specifically, a method 10 for using a sheet (e.g., a second insulating member) on an eye compress system (e.g., a therapeutic device) applied to an eye region of a user is shown. In some embodiments, the eye compress system can include and/or can otherwise be substantially similar to, for example, the therapeutic device 300. As such, the eye compress system can include at least a frame (e.g., such as the frame 310) coupled to a therapeutic member (e.g., such as the therapeutic member 305) configured to transfer thermal energy to the ocular region of the user.

The method 10 includes providing a sheet to a user, at 11. In some embodiments, the sheet can be, for example, any of the second insulating members described herein such as, for example, the second insulating members 370 (FIGS. 33-44), 2170 (FIG. 78), 2270 (FIG. 79), 2370 (FIGS. 80-83), 2470 (FIG. 84), 2570 (FIGS. 85 and 86), 2670 (FIG. 87), 2770 (FIGS. 88 and 89), 2870 (FIG. 90), and/or 2970 (FIG. 91). In one embodiment, the sheet can be substantially similar to or the same as the second insulating member 370 described in detail above. In this manner, the sheet can be provided and/or otherwise disposed within a packaging such as, for example, the package 375 of FIG. 37. In some embodiments, the sheet can be disposed in the package in a substantially folded configuration. In other embodiments, the sheet can be disposed in the package in a substantially nonfolded configuration.

The sheet is positioned on the eye compress system, at 12. In some embodiments, the sheet includes at least one folded region that can substantially correspond with, for example, a set of attachment portions of a therapeutic member and/or the like. For example, in some embodiments, a therapeutic member such as the therapeutic member 305 can include a set of couplers configured to couple the therapeutic member to a frame such as the frame 310. Thus, the sheet can be disposed on a surface of the therapeutic member and can be positioned such that the folded regions substantially cover the couplers. In this manner, the increased thickness of the folded region (as described, for example, with reference to FIG. 35) can increase a user's comfort by, for example, buffering (e.g., physically, thermally, etc.) the user from the couplers.

In some embodiments, the sheet can be optionally sprayed with a fluid, at 13. For example, in some embodiments, the sheet can be disposed in a package that can be configured to maintain a desired moisture content and/or level of the sheet. In some instances, a user can increase the moisture content of at least a portion of the sheet by spraying the sheet with a fluid that can be configured to, for example, enhance the transfer of thermal energy between the ocular region of the user and the eye compress system. For example, the user can spray a fluid on the sheet prior to coupling the eye compress system to his or her head. In some embodiments, the fluid can include and/or can otherwise be composed of, for example, an aqueous solvent, a facial botanical extract blend (e.g., Aloe Vera, cucumber extract, and/or the like), 1,3-Dimethylol-5,5-dimethylhydantoin (DMDM hydantoin), iodopropynyl butylcarbamate, propylene glycol, butylene glycol, and any suitable fragrance and/or aromatic agent. In this manner, the fluid can, for example, provide greater comfort to the user, by increasing the amount of moisture applied to the user's body and/or by providing an aromatic and/or other therapeutic agent, as described in detail above with reference to FIG. 36.

With the sheet having the desired moisture content, the eye compress system is applied to the face of the user such that a nonfolded region of the sheet is applied substantially to the eyelids of the user, at 14. In some embodiments, the user can couple the eye compress to his or her head in a similar manner as described above with reference to the therapeutic device 300. More particularly, in some instances, the user can manipulate the eye compress system to increase a potential thermal energy of, for example, a therapeutic member prior to applying the eye compress to his or her head. In other instances, the user can also manipulate the eye compress system to increase a potential thermal energy of, for example, a therapeutic member by manipulating the therapeutic member while the eye compress is applied to his or her head. By way of example, the user can place at least the therapeutic member in a microwave oven to add thermal energy to the therapeutic member in a similar manner as described above with reference to FIGS. 38 and 39. With the desired amount of thermal energy transferred to the therapeutic member, the user can place his or her face in contact with the sheet and can manipulate, for example, a coupling portion or the like to couple the eye compress system to his or her head such that the nonfolded region of the sheet is substantially aligned with the eyes. Thus, thermal energy can be transferred from the eye compress system to the ocular region of the user in a similar manner as described above with reference to the therapeutic device 300.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. Similarly, where methods and/or events described above indicate certain events and/or procedures occurring in certain order, the ordering of certain events and/or procedures may be modified. While the embodiments have been particularly shown and described, it will be understood that various changes in form and details may be made.

Although various embodiments have been described as having particular features and/or combinations of components, other embodiments are possible having a combination of any features and/or components from any of embodiments as discussed above.

What is claimed is:

1. An eye compress system, comprising:
a thermally adjustable pack, the thermally adjustable pack having a periphery and defining a single chamber containing a thermally activatable substance, the thermally adjustable pack having an external perimeter, a surface area, a rear surface, and a front surface, the external perimeter of the thermally adjustable pack configured to circumscribe a first eye and a second eye of a user when the thermally adjustable pack is applied to the eye region of the user's body; and
an external frame having an external perimeter and a surface area, the external frame being configured to be coupled to the thermally adjustable pack, the external perimeter of the external frame configured to circumscribe the first eye and the second eye of the user, the surface area of the thermally adjustable pack being greater than the surface area of the external frame,
the rear surface of the thermally adjustable pack configured to be in substantial conductive thermal contact with eyelid skin of the first eye and eyelid skin of the second eye of the user when the thermally adjustable pack is applied to the eye region of the user's body.

2. The eye compress system of claim 1, wherein from an anterior perspective, the external frame covers substantially less than the total surface area of the thermally adjustable pack.

3. The eye compress system of claim 1, wherein the external frame includes a first frame section having a first internal periphery defining a first relief opening and a second frame section having a second internal periphery defining a second relief opening, each relief opening circumscribing an eye of the user.

4. The eye compress system of claim 3, wherein the internal periphery of the first relief opening and the second relief opening circumscribe periorbital regions lying substantially peripheral to the first and second eyes of the user.

5. The eye compress system of claim 1, wherein the thermally activatable substance is a gelatinous thermally activatable substance.

6. The eye compress system of claim 1, wherein peripheral portions of the thermally adjustable pack containing the thermally activatable substance extend posterior to portions of the external frame positioned peripheral to the eyes of the user, such that, when the apparatus is applied to the eye region of the user, the peripheral portions of the thermally activatable substance is sandwiched between the peripheral portions of the external frame and peripheral periorbital regions of the user.

7. The eye compress system of claim 1, further including a pair of head straps, the head straps designed to be coupled to right and left sides of the external frame and to circumscribe a head of the user when the thermally adjustable pack is applied to the eye region of the user's body.

8. The eye compress system of claim 7, wherein, when the head straps are applied around the head of the user, the head straps transmit a rearward force upon the external frame which is transmitted therethrough onto peripheral areas of the thermally adjustable pack, such that portions of the thermally activatable substance are sandwiched between the external frame and periorbital regions of the user.

9. The eye compress system of claim 7, wherein each of the head straps includes a V-shaped element, each V-shaped element having a superior member and an inferior member, each of the superior and inferior members having an anterior portion and a posterior portion, the posterior portions of the superior and the inferior members forming an apex directed posteriorly from the eye region, the anterior portions of the superior and the inferior members coupled to lateral portions of the external frame.

10. The eye compress system of claim 9, wherein each of the superior members includes an anterior end positioned superior to the eyes of the user, and each of the inferior members includes an anterior end positioned inferior to the eyes of the user, when the apparatus is applied to the eye region of the user.

11. The eye compress system of claim 9, wherein the superior and inferior members of the V-shaped element each has a longitudinal elasticity, the longitudinal elasticity of the superior members being substantially less than the longitudinal elasticity of the inferior members.

12. The eye compress system of claim 1, wherein when a rearward force is applied to the external frame, the external frame compresses portions of thermally activatable substance underlying the external frame, and displaces the portions of thermally activatable substance from peripheral areas of the thermally adjustable pack into central areas of the thermally adjustable pack, when the eye compress system is applied to the eye region of the user.

13. The eye compress system of claim 1, wherein, when the apparatus is applied to the eye region of the user, the external frame has a convex configuration in a lateral direction and peripheral side portions of the external frame have a convex configuration in a superior-inferior direction.

14. The eye compress system of claim 1, wherein prior to the apparatus being applied to the user's head in a position of use, the external frame has a first undeformed configuration, and wherein, after being applied to the user's head in a position of use, the external frame attains a second deformed configuration, the first undeformed configuration being substantially flat or planar, and the second deformed configuration being substantially convex in both a superior-inferior direction and a lateral direction.

15. The eye compress system of claim 1, the external frame having a left superotemporal region and a right superotemporal region, each of the left and right superotemporal regions being narrower than regions immediately superior and inferior to the left and right superotemporal regions, the narrowing of the left and right superotemporal regions designed to partially weaken the frame so as to induce a convex bending of the frame at the left and right superotemporal regions when the eye compress system is applied to the eye region of the user.

16. The eye compress system of claim 1, the thermally adjustable pack being coupled to the external frame with an upper coupler and a lower coupler, wherein, when the eye compress system is applied to the eye region of the user, the external frame bends anteriorly, decreasing a distance between the upper coupler and the lower coupler.

17. The eye compress system of claim 1, further including an insulating member configured to reduce thermal transfer from or to the thermally adjustable pack, the insulating member coupled to the external frame.

18. The eye compress system of claim 17, wherein the insulating member includes right and left conical protuberances each having an apex positioned anterior to a right and a left periorbital region of the user respectively, when the apparatus is applied to the eye region of the user.

19. The eye compress system of claim 18, wherein the insulating member is configured to have a first substantially flat or planar configuration when in a resting state, and a second substantially convex configuration when coupled to the external frame.

20. The eye compress system of claim 1, further including a moist disposable fibrous nonwoven fabric sheet configured to be removably positioned upon a rear surface of the thermally adjustable pack, such that when the eye compress system is applied to the eye region of the user, the sheet is sandwiched between the thermally adjustable pack and eyelid skin of the user.

* * * * *